(12) United States Patent
Barrett et al.

(10) Patent No.: US 9,785,792 B2
(45) Date of Patent: Oct. 10, 2017

(54) SYSTEMS AND METHODS FOR PROCESSING REQUESTS FOR GENETIC DATA BASED ON CLIENT PERMISSION DATA

(71) Applicants: Ryan Barrett, San Francisco, CA (US); Othman Laraki, Atherton, CA (US); Wendy McKennon, San Francisco, CA (US); Katsuya Noguchi, San Francisco, CA (US); Huy Hong, Palo Alto, CA (US)

(72) Inventors: Ryan Barrett, San Francisco, CA (US); Othman Laraki, Atherton, CA (US); Wendy McKennon, San Francisco, CA (US); Katsuya Noguchi, San Francisco, CA (US); Huy Hong, Palo Alto, CA (US)

(73) Assignee: COLOR GENOMICS, INC., Burlingame, CA (US)

( * ) Notice: Subject to any disclaimer, the term of this patent is extended or adjusted under 35 U.S.C. 154(b) by 0 days.

(21) Appl. No.: 15/163,191

(22) Filed: May 24, 2016

(65) Prior Publication Data
US 2017/0255790 A1    Sep. 7, 2017

Related U.S. Application Data

(60) Provisional application No. 62/303,531, filed on Mar. 4, 2016.

(51) Int. Cl.
*G06F 21/62* (2013.01)
*G06F 17/30* (2006.01)

(52) U.S. Cl.
CPC .... *G06F 21/6218* (2013.01); *G06F 17/30867* (2013.01)

(58) Field of Classification Search
CPC ................ G06F 21/6218; G06F 17/30867
See application file for complete search history.

(56) References Cited

U.S. PATENT DOCUMENTS

2002/0187496 A1* 12/2002 Andersson .............. G06F 19/28
                                                            435/6.14
2003/0040002 A1*  2/2003 Ledley .................... G06F 19/24
                                                            435/6.11

(Continued)

OTHER PUBLICATIONS

Richards, et al., "Standards and guidelines for the interpretation of sequence variants: a joint consensus recommendation of the American College of medical Genetics and Genomics and the Association for Molecular Pathology" and Supplementary Information, Genetics in Medicine (2015), pp. 405-423 (22 pages).

(Continued)

*Primary Examiner* — Ellen Tran
(74) *Attorney, Agent, or Firm* — Kilpatrick Townsend & Stockton LLP

(57) ABSTRACT

Methods and systems disclosed herein relate generally to processing data requests from external assessment systems. More specifically, an interface is availed to external assessment systems that accepts an identification of one or more genes. Upon receiving a request identifying one or more genes, a type of access authorized for the requesting external assessment system is assessed. When it is determined that the type of data access indicates that the external assessment system is authorized to access data for the one or more genes, a data repository is queried to identify client data that corresponds to the one or more genes and that indicates or can be used to detect a presence of client-associated variants. A response data set that includes at least some of the client data is transmitted to the external assessment system.

21 Claims, 21 Drawing Sheets

(56) References Cited

U.S. PATENT DOCUMENTS

| | | | |
|---|---|---|---|
| 2004/0133358 A1* | 7/2004 | Bryant | G06F 19/18 |
| | | | 702/19 |
| 2005/0001520 A1 | 1/2005 | Cummings | |
| 2006/0010117 A1* | 1/2006 | Bonabeau | G06F 17/30864 |
| 2007/0288439 A1* | 12/2007 | Rappaport | G06F 17/30867 |
| 2009/0094059 A1* | 4/2009 | Coleman | G06F 19/3456 |
| | | | 705/3 |
| 2010/0115421 A1* | 5/2010 | Bejjani | G06F 15/16 |
| | | | 715/751 |
| 2010/0121872 A1* | 5/2010 | Subramaniam | G06F 19/28 |
| | | | 707/769 |
| 2012/0196571 A1 | 8/2012 | Grkov et al. | |
| 2014/0032125 A1* | 1/2014 | Hawkins | G06F 19/28 |
| | | | 702/19 |
| 2014/0325587 A1* | 10/2014 | Nilsson | H04L 63/20 |
| | | | 726/1 |
| 2014/0331084 A1* | 11/2014 | Sawazaki | G06F 3/061 |
| | | | 714/6.23 |
| 2015/0213389 A1* | 7/2015 | Modarresi | G06Q 10/06393 |
| | | | 705/7.39 |
| 2015/0370840 A1* | 12/2015 | Wilhelm | G06F 17/30324 |
| | | | 707/744 |
| 2016/0049071 A1 | 2/2016 | Beaver et al. | |
| 2016/0066189 A1 | 3/2016 | Mahaffey et al. | |

OTHER PUBLICATIONS

Loria, Kevin, "A new $100 million company could transform the way we interact with our own DNA," "Business Insider", Aug. 24, 2015, all pages, Retrieved from: http://www.businessinsider.com/what-helix-could-learn-from-genome-sequencing-for-you-2015-8.
U.S. Appl. No. 15/169,294, filed May 31, 2016, all pages.

* cited by examiner

SYSTEMS AND METHODS FOR PROCESSING REQUESTS FOR GENETIC DATA BASED ON CLIENT PERMISSION DATA

CROSS-REFERENCE TO RELATED APPLICATIONS

This application claims the benefit of and the priority to U.S. Provisional Application No. 62/303,531, filed on Mar. 4, 2016, which is hereby incorporated by reference in its entirety for all purposes.

FIELD

Methods and systems disclosed herein relate generally to processing data requests from external assessment systems. More specifically, a data repository is queried to identify client data that corresponds to specified units and that indicates or can be used to detect a presence of client-associated sparse indicators.

BACKGROUND

Data is being generated at an exponentially increasing rate. Frequently, data is generated for a particular purpose. The generation, transmissions, storage and/or processing of the data may then be performed in accordance with a given protocol. Very frequently, after the protocol has been completed, the data is not again used. The data may be deleted from a data store (if it was ever stored), or a data store (or portion of the data store) on which the data was stored may stop being used. Nonetheless, the data may have potential other uses. Data reuse may be particularly advantageous in instances in which a data set is unique or is associated with a high collection or generation cost. Thus, it may be advantageous to identify techniques for facilitating distributions of part or all of one or more data sets.

SUMMARY

In some embodiments, a platform is offered to enable developers to request select genetic data for one or more clients (e.g., particularly identified, identified via a client characteristic or generally identified as any client). The platform may be configured to include a genetic app store that is managed by a central system and facilitates controlled provision of clients' data to developers and facilitating subsequent interactions between developers and clients (e.g., to convey results of developers' analyses to clients). Requests can be processed to determine whether a given developer is authorized to receive the requested data. Upon provision of data, a developer can analyze the data and provide results to the clients directly or to the managing system (e.g., to provide to clients).

In some embodiments, systems and methods relate to controlled distribution of client data. Various pre-approval steps may be implemented to determine what types of data distributions are authorized by a given client. For example, a client may specify that distribution of data pertaining to particular genes, for particular types of analyses (e.g., particular types of disease-risk of medication-efficacy analyses) is to be permitted (or conditionally permitted or not permitted). Permissions for performing medication analyses may specify what types of medications can be assessed (e.g., those in trials, approved, with specific journal-publication support) and/or how many medications can be assessed.

Pre-approvals may also include indications regarding to whom results will be released. Permissions may also specify or constrain how or whether raw data is stored (e.g., all of genome, sequences from select genes and/or just variants). Potentially, a permission indicates whether a client's data is permitted to be provided for research analyses. In various instances, pre-approvals may be configured to operate in accordance with an opt-in or opt-out protocol, so as to identify whether a default distribution decision is to allow or to deny data distribution to external entities.

Due to various requirements as to a need to release particular risk results, pre-approval pertaining to whether various types of variant detection may be particularly important (because detecting a variant may require disclosure, so it may need to be avoided initially). Permissions may extend to other types of data and/or data combinations. For example, a configuration may enable a client to specify that distribution of data identifying variant detection (e.g., variant type and location) is to be permitted but distribution data identifying a sequence is to be refused. Other types of data may include heart rates, lipid profiles, sensor data, health record info, etc.

In some embodiments, a central system may collect clients' data (e.g., to be used for local analyses and/or provided, in a restricted manner, to developers) from a variety of sources. Such data collection may include integrating with different platforms. The sources may include one or more devices associated with the central system or another device (e.g., associated with a developer, physician or patient). The data collection may include crowd-sourcing pertinent data. In response to receipt of data pertaining to a client from a data source, the central system may coordinate to provide the data source with payment information, other data pertaining to the same client or data pertaining to a different client. In various instances, upon receiving the data from a source, a central system may have full or limited control on the data. For example, a communication rule may indicate that the central system may use the data for local analyses but cannot distribute the raw data to other entities. In various instances, received data may be "owned" by a data source, the central system or a client. Different sources may be assigned different credibility.

In some embodiments, risk assessments and/or biological analyses may use primary data (e.g., assessments of a sample or from a physician) pertaining to a relative of a client (e.g., in addition to or as an alternative to primary data pertaining to the client). In some instances, use of relatives' data may be subject to access control and/or an authorization (e.g., opt-in) by the client and/or relative of the client. The relative may include one as identified via input or automatically detected from genetic analysis. This type of data analysis may be, in some instances, more informative than the data provided via inputs as to whether (for example) a relative has or is at risk for having a disease. In some instances, a weight placed on primary data pertaining to a relative decreases as additional primary data is received from a client. For example, an initial biological analysis may be performed based on primary data from one or more relatives and a client's input. Subsequently, primary data for the client may be received, and the analysis may be repeated so as to decrease the weight applied to or use of the primary data of the relative(s).

Various types of biological analyses and/or risk assessments may (but need not) be associated with a fee charged to a client. Clients may be charged differently based on how many genes or panels were ordered. There may be a threshold where a client would "own" his/her full genome data.

For example, in one instance, upon ordering at least a predefined number of assessments (e.g., risk assessments for a predefined number of conditions), one or more assessments pertaining to an evaluation of at least a predefined portion of the genome (e.g., number of genes and/or total sequence lengths), additional analyses may be provided for a reduced fee or no fee. In some instances, it may be required that the threshold be met with a single request, while in some instances, a cumulative assessment of multiple requests may be used to determine if the threshold is exceeded. When the threshold is met or exceeded, an assessment sequence (in some instances) may proceed to sequence an entire genome (or all portions of a genome relevant to any potential assessment) A model or algorithm may be used to predict which assessments a client is willing to subsequently request and prices may be adjusted accordingly. If advertisers and/or researchers are allowed to up-sell, client charges may be reduced.

Fess may (but need not) also be charged to a developer requesting data access. In some embodiments, developers can be charged differently based on how many genes' data is being requested, a type of data being requested (e.g., a raw sequence, an aligned sequence, variant-detection results, client inputs and/or personal health information data), and/or whether to developer is providing any data (e.g., for a same or different client).

In some embodiments, developers can submit queries to a managing system of the genomic app store. The queries may specify particular parts of the genome. The queries may request different or other types of data (e.g., blood sugar, lipid levels, activity patterns, health history, and/or sensor data, such as heart rate) and/or other types of data may be automatically identified as relevant. Queries can be evaluated based on authentication analyses and/or permissions. Quality control measures may be provided that corresponds to responsive data.

In some embodiments, clients' data may be partially or fully anonymized or de-identified. Data that is associated with client's identities and their data may be stored and managed by an app-store managing system. In some instances, a client may be provided with a key to reveal data correspondence. A client may also be provided with an opportunity to delete corresponding data, which may result in total deletion of the data and/or de-identification of data.

In some embodiments, one or more developers may perform analyses to detect one or more diseases and/or to generate predicted affinities or medication efficacies. Clients with above-threshold results may then be identified. External assessment devices of developers may transmit alerts to client devices directly that identify the risk or risk and/or the transmission may be sent to an app-store managing system (which may then alert the client devices). Alerts may also be based on analyses performed for relatives. Identities of client may, or may not, be hidden from developers. Post-hoc alerts may also relate to "fun", recreational and/or non-clinical predictions, such as an eye color of child if a client had a child with a particular celebrity. Post-hoc analyses that are likely to be ordered or likely to be of interest to a given client may influence whether a sample is stored or whether the analysis is performed in the short-term.

In some embodiments, a computer-implemented method is provided for conditionally querying data repositories for data for specified units in response to receiving request communications over interfaces. One or more interfaces are availed to each of a plurality of external assessment system. The one or more interfaces that include a field that accepts an identification of one or more units. Each unit corresponds to a set of predefined positions within a data structure.

A request communication is received from an external assessment system of the plurality of external assessment systems and over an interface of the one or more interfaces. The request communication identifies one or more units and that corresponds to a request for data for the one or more units. The data requested is of a type that indicates or can be used to detect a presence of one or more sparse indicators. Each sparse indicator of the one or more sparse indicators identifies a distinction between a client data set represented in the data and corresponding to the one or more defined units and a reference data set corresponding to the one or more defined units.

A type of data access authorized for the external assessment system is determined. It is determined whether the type of data access indicates that the external assessment system is authorized to access data for the one or more units. When it is determined that the type of data access indicates that the external assessment system is authorized to access data for the one or more units, a data repository is queried for the data for the one or more units. In response to the query, a query response is received that includes, for each client of a plurality of clients, client data of a type that indicates or can be used to detect a presence of one or more sparse indicators. The query response or processed version of the query response is transmitted to the external assessment system.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures:

FIG. 1 shows a representation of a data processing network, in accordance with some embodiments of the invention;

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

Figure 1:
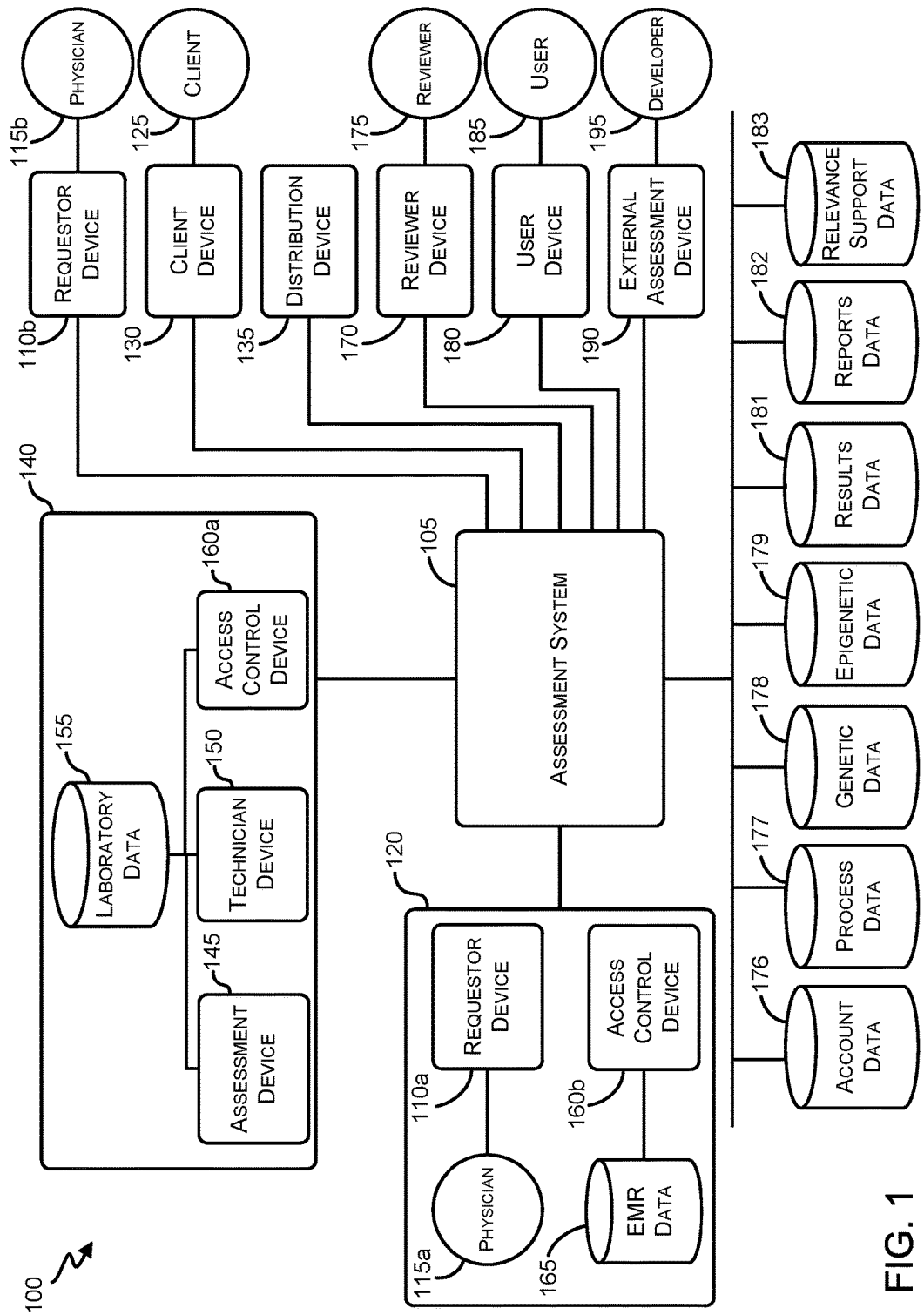
FIG. 1 shows a genetic assessment network in one embodiment.

Referring initially to FIG. 1, a genetic assessment network 100 is shown in one embodiment. Through the interaction of multiple devices and entities, an assessment system 105 can generate an output that includes a risk variable and/or risk assessment indicating an estimated risk of each of one or more particular conditions (e.g., breast cancer and ovarian cancer) for a particular individual (also referred to herein as a client or subject).

More specifically, assessment system 105 receives an electronic request from a requestor device 110. Assessment system 105 may include one or more electronic devices (e.g., servers and/or computers) and may, but not need, reside partly or entirely at a remote server. Requestor device 110 may be one configured and located to receive input from a physician 115. In one instance, requestor device 110a is located in an external physician-associated facility 120, such as a physician's office or hospital. In one instance, requestor device 110b includes an internally linked requestor device 110b, such as ones that itself receive invitations, from assessment system 105, to generate electronic requests.

The electronic request can include an order to conduct a genetic analysis and/or to conduct one or more types of risk assessments. The electronic request may identify, or otherwise indicate, one or more conditions to be evaluated during the genetic analysis and/or risk assessment. The electronic request may identify a patient and/or include additional data pertaining to the patient, such as identifying, health, and/or medication data of the patient.

The patient may be equated to, by assessment system 105, a client 125. In some instances, a client device—associated with client 125—initially transmits a preliminary electronic request for the genetic analysis and/or risk assessment to assessment system 105. For example, such a preliminary electronic request may be initiated via client interaction with a website associated with assessment system 105. The same or a subsequent preliminary request may identify a particular physician (e.g., by name, office location, phone number, and/or email address) and/or may request that a physician 115b associated with an internally linked requestor device 110b submit such a request.

When a particular physician (or other medical entity) is identified in a preliminary electronic request, assessment system 105 may identify a destination address (e.g., IP address or email address) associated with the physician and transmit a communication identifying information associated with the preliminary request (e.g., the client, a type of genetic analysis, and so on). The communication may include a partial order and/or an input field that would confirm that the order requested by client 125 is to be generated and transmitted back to assessment system 105. Such a communication may facilitate receipt of the electronic request from requestor device 110b.

When it is requested that a physician 115b associated with an internally linked requestor device 110b submit such a request, assessment system 105 may transmit a similar communication to a requestor device 110b that may have been selected from amongst multiple internally linked requestor devices. The selection may be based on a load balancing technique, physician office hours, physician expertise, locations of the multiple requestor devices, a pseudo-random selection technique, and/or an insurance affiliation.

Once the electronic request has been received from a requestor device 110 (e.g., in response to a preliminary electronic request from a client device 130), assessment system 105 may evaluate the electronic request to ensure that all required data (e.g., which may include a name, address, insurance, billing and/or payment information, such as credit card information) has been provided from physician 115a and that all required data pertaining to client 125 has been identified (e.g., via the electronic request, a preliminary request and/or stored data). If assessment system 105 determines that all required information has not been identified, a request for such information may be transmitted to requestor device 110 and/or client device 130. In various instances, a fee made due to a client depends on an analysis requested, whether (and what kind) of new sequencing is required for the analysis, a number of genes being assessed (e.g., and whether they have been previously assessed), a number (and/or type) of analyses being requested, a number (and/or type) of analyses previously requested, a number (and/or type) of analyses predicted to be requested subsequently, whether a client is granting other entities' access to the client's genetic data or results, whether a client is granting permission for additional analyses to be performed on the client's data, and/or whether a client is granting permission to send offers to request client access to results or reports other than those initially being requested.

When all required information has been provided, assessment system 105 can send an instruction communication to a distribution device 135. The instruction communication can include (for example) a name and address of client 125 and, in some instances, an indication as to what is to be sent to client 125. For example, an electronic request may indicate a type of analysis that is to be performed on a biological sample (e.g., a genetic analysis pertaining to a risk of getting one or more particular types of cancers) and/or a type of biological sample (e.g., a saliva sample) that is to be analyzed. The instruction communication may identify the type of analysis, type of biological sample and/or kit associated with collection thereof. The instruction communication may thus facilitate and/or trigger a physical distribution of a kit for collecting a biological sample to a client address. The kit may include, for example, instructions as to how to collect a sample, a container for storing the sample, an envelope or package for sending the container and sample to be analyzed, and/or information pertaining to an order or type of analysis to be conducted.

A sample from client 125 may then be received at a laboratory 140. Laboratory 140 may include one or more assessment devices 145 configured to sequence all or part of the genome and/or all or part of the epigenome using the sample. For example, an assessment device 145 may include a DNA sequencer and/or PCR machine. Laboratory 140 may further include one or more technician devices 150, such as a desktop or laptop computer. Data generated by or at one or more laboratory devices (e.g., assessment device 145 or technician device 150) may be stored at a laboratory data store 155, which may be remote from all laboratory devices or part of a laboratory device. The laboratory data may, for example, include identifying client information (e.g., a name and address), laboratory information (e.g., location and name), device specifications (e.g., manufacturer and model of assessment devise) and genetic data (e.g., genetic sequences).

In some instances, data is alternatively or additional collected from one or more other systems. For example, genetic data and/or results generated based on processing of genetic data may be received from one or more other systems that generated the data based on external laboratory processing and/or client inputs. As another example, data may include genetic data (or results based on genetic data) corresponding to another person (e.g., an entity related to a client and/or an entity sharing a characteristic with a client). The other person may be one, for example, that is identified based on input from the client and/or automatically identified (e.g., based on a query of a data store to identify clients associated with inputs or results indicating a shared characteristic or relationship). In some instances, a risk variable may be generated based on data from multiple other people, and the data for each other person may be weighted based on (for example) how closely related the person is with a client and/or how many or which characteristics the person shares with a client.

An access control device 160a may control which devices and/or entities may gain access to the laboratory data, which may apply to devices and/or entities internal to laboratory 140 and/or to devices and/or entities external to laboratory 140. Access control device 160a may implement one or more rules, such as restricting access to client data to one or more particular devices (e.g., associated with assessment system 105). Such access may further or alternatively be controlled via logins, passwords, device identifier verification, etc.

In various instances, access control device 160a controls access via control of pushed transmissions and/or via control of processing pull requests. For example, a rule may indicate that laboratory data pertaining to a sample is to automatically be transmitted to a particular assessment system 105 (and/or device associated therewith) upon completion of a laboratory-based assessment or detection of particular data (e.g., data matching a request). Access control device 160a may then monitor for such a condition to be met and may then generate and transmit appropriate data.

Laboratory data can include a plurality of sequencing reads. It may be advantageous to exclude one or more the plurality of sequencing reads. For example, the plurality of sequencing reads may include duplicate reads. As another example, a sequencing read may correspond to a sub-threshold quality metric. In various instances, a device at laboratory 140 or assessment system can evaluate sequencing reads for potential exclusion. It will be appreciated that two duplicate sequencing reads need not correspond to precisely a same sequence, as one sequencing read may include data at a beginning or end of the read not present in the other. Accordingly, the evaluation may include aligning each sequencing read with a reference sequence.

It will be appreciated that genetic assessment network 100 can, in some instances, include multiple laboratories 140, each of which can include an assessment device 145, technician device and/or access control device 160a. Further, a given laboratory 140 can, in some instances, include multiple assessment devices 145, multiple technician devices 150 and/or multiple access control devices 160a. Thus, data received at assessment system 105 can include data collected by and/or derived from data collected by different assessment devices, which may result in the data having different biases, units, and/or representation. Similarly, laboratory personnel operating different technician devices 150 may utilize different protocols and/or data interpretation techniques, which may again result in receipt of data at assessment system 105 that has different biases, units, variables, and so on. Further, even data originating from a same device may, in time, exhibit different biases, units, and so on, which may be a result of a manipulation of a control of the device and/or equipment wear.

Thus, in some instances, assessment system 105 performs a comparison across data received from a laboratory device (e.g., an access control device 160a or directly from an assessment device 145 or technician device 150). The comparison may be across, for example, data collected at different laboratories, data based on measurements collected at different devices, and/or data collected at different times. It will be appreciated that the comparison may include a direct comparison of collected data or comparing preprocessed versions of the collected data. For example, received data may first be preprocessed via a transformation and/or dimensionality-reduction technique, such as principal component analysis, independent component analysis, or canonical correspondence analysis.

The comparison can include, for example, performing a clustering technique so as to detect whether data corresponding to a given laboratory, device or time period predominately resides in a different cluster than data corresponding to one or more other laboratories, devices or time periods. The clustering technique may include, for example, a connectivity based clustering technique, a centroid-based clustering technique (e.g., such as one using k-means clustering), a distribution-based clustering technique, or a density-based clustering technique.

The comparison may additionally or alternatively include a statistical technique, such as one that employs a statistical test to determine whether two or more data sets (e.g., corresponding to different laboratories, devices or time periods) are statistically different. For example, a Chi-square, t-test or ANOVA may be used.

The comparison may additionally or alternatively include a time-series analysis. For example, a regression technique may be used to determine whether output from a given device is gradually changing in time.

When it is determined that particular data corresponding to a given laboratory, device or time period is different than data corresponding to one or more other laboratories, devices or time periods (e.g., is assigned to a different cluster than other data or is associated with a p-value below a threshold), a normalization and/or conversion factor may further be identified. For example, a normalization and/or conversion factor may be identified based on centroids of data clusters and/or inter-cluster distances. As another example, a linear or non-linear function may be derived to relate data from a given laboratory, device or time period to other data.

In some instances, a determination that particular data corresponding to a given laboratory, device or time period is different than data corresponding to one or more other laboratories, devices or time periods may indicate that data from the given laboratory, device or time period is not to be used. In such instances, an instruction communication may be sent to a laboratory to reprocess a sample.

In addition to receiving laboratory data, assessment system 105 may further collect one or more other types of data that may be used to assess, for example, a health risk. For example, one other type of data may include health-related inputs provided at a client device 130, such as inputs that indicate medical history, current conditions, familial health statuses or conditions, age, eating habits, exercise patterns, occupation, exposure to environments associated with toxic chemicals, and so on. Another type of data may include data automatically detected at a client device 130. For example, a wearable client device may track activity patterns so as to estimate calories burned per day, or the wearable client device may estimate a pulse distribution, user temperature, sleep patterns and/or indoor/outdoor time. This data may be directly transmitted (e.g., after a request and/or authorization handshake) to assessment system 105 and/or via another client device (e.g., via accessing health data on a phone or computer client device). Yet another type of data may include electronic medical record (EMR) data, which may be stored, for example, at a EMR data store 165 at and/or associated with an external physician-associated facility, such as one having provided an electronic request to perform an analysis or assessment pertaining to a client and/or one as identified via input at a client device 130. To illustrate, the other data may identify one or more symptoms and/or physician evaluation results for a client or may include a result of one or more medical tests (e.g., mammogram, MM, pulmonary function, EKG, etc.).

In some instances, other data may include data pertaining to a different client. For example, it can be determined or estimated that a given client is related to another client. Such determination or estimation may be based on inputs detected at a client device identifying one or more family members (e.g., by name), and a data store can be queried to determine whether any clients match any of the family member identifications. Such determination or estimation may alternatively or additionally be based on a genetic analysis, such that DNA from the given client is compared to DNA from some or all other clients to identify (for example) whether any other clients share a threshold portion of DNA with the client. Upon detecting an above-threshold match, a percentage of shared DNA may be used to estimate a type of relationship between the clients.

Upon identifying a related client, other data may include (for example) genetic data, epigenetic data, inputs, medical-record data, data indicative of activity or status, or data derived thereupon that corresponds to the related client. Such data may be informative in assessing a client's risk for a condition, as it may be analogous to evaluating a family history of conditions. To illustrate, if a client's sister has a pathogenic variant that indicates that the sister is highly likely to develop a given cancer, this risk may influence the client's risk assessment in a manner similar to that which an indication that the sister had developed a given cancer would have (though a magnitude of influence may differ).

In some instances, other data may include (for example) genetic data, epigenetic data, inputs, medical-record data, data indicative of activity or status, or data derived thereupon that corresponds to one or more different clients with a shared characteristic. For example, a set of clients that share a given client's birth city or childhood city may be identified. Risk analyses from the set of clients may be informative in a risk analysis for the client, as an environmental factor may have influenced a probability of developing a given condition. For example, exposure to a toxin or polluted water may increase disease propensity, while cultures of eating particular foods, exercising and/or moderate sun exposure may decrease disease propensity.

In various instances, the other data may be transmitted to assessment system 105 prior to any, or in response to a, request from assessment system 105 for such. For example, client input other data may be provided as part of a preliminary request from client device 130 and EMR data may be provided as part of an electronic request from requestor device 110a. As another example, upon receiving a preliminary request from a client device, assessment system 105 may request that a client authorize access to health data stored on the client device, such that it may be (e.g., via an app) retrieved and transmitted to assessment system 105.

Thus, assessment system 105 may have access to—for a given subject—one or more genetic sequences, epigenetic modification data, client-reported data, medical record data, medical test data, activity (e.g., exercise) data, and/or other types of data. Genetic sequences can be evaluated to detect and assess genetic variants. The detection and/or assessment may be performed, for example, partly or fully at assessment system 105. In some instances, the detection and/or assessment is performed in a fully automated manner. In some instances, the detection and/or assessment involves processing of inputs provided by a reviewer.

Detecting genetic variants can include aligning each sequencing read with a reference sequence. The reference sequence can include part of a human reference genome and/or can include a sequence identified based on identifying median or mode bases across a plurality of sequences derived from samples from a population of humans.

An aligned sequence can then be compared to the reference sequence to detect variants. A variant may include, for example, a single nucleotide polymorphism (SNP), multi-nucleotide polymorphism (MNP), insertion, deletion, copy number variation, duplication, inversion and/or translocation. Variants may be detected using a variety of techniques. For example, in one instance, for each sequencing read that differs from a reference sequence, one or more possible variant identifications may be generated, and each may be assigned a score. The score may penalize, for example, for increased numbers of variants or indications that a smaller portion of a sequence corresponds to a reference sequence. For example, scores may be assigned using a rank sum test (e.g., ReadPosRankSumTest, ClippingRankSumTest or MappingQualityRankSumTest), a Hardy-Weinberg test for transmission disequilibrium (e.g., HardyWeinberg), a root mean square technique (e.g., RMSMappingQuality), or a technique assessing consistency of a site with strictly two segregating haplotypes (e.g., HaplotypeScore). A given variant identification (which may include multiple variants, but pertains to a single sequence) may be selected based on the identification corresponding to a low, below-threshold or lowest score (e.g., assuming that high scores reflect high penalties). In some instances, a given base difference may be a part of multiple variants. For example, the base difference may itself be represented as an SNP, but if one or more neighboring bases also differ from a reference sequence, it can also be part of an MNP.

Some variants (e.g., indel variants) can disrupt alignment of a sequencing read. CIGAR strings can be generated to summarize how bases of a given sequencing read correspond to (e.g., match, mismatch, are added to, or are deleted from) a reference sequence. One or more features in CIGAR strings may indicate that the sequencing read should be excluded from further analysis, as it likely reflects an erroneous corresponding sequence. Such features may include, for example, Hard/Soft clips in the middle of a CIGAR string, a deletion (with or without a preceding clip) that starts the read, a deletion (with or without a preceding clip) that ends the read, a fully hard or soft clipped read, or consecutive indels in the CIGAR string.

Variant characteristics can be assessed to determine whether to reject a given variant. The assessment can include, for example, determining a read coverage, allelic faction, position relative to a reportable range and/or proximity to a problematic homopolymer. For example, variants with a read coverage less than a threshold, such as 10, 20 or 50, can be excluded. As another example, variants with an allelic fraction less than a threshold (e.g., 5%, 10% or 20%) can be excluded. As yet another example, a variant outside of a reportable range can be excluded.

Once a variant is detected, it can be assigned a category, which can reflect a potential biological impact. For example, potential categories can include a Benign category and a Pathogenic category. Categories may differ in terms of confidence of an impact (or lack thereof). For example, potential categories can include a Benign category, Likely Benign category, Likely Pathogenic category and Pathogenic category. A categorization may be determined based on, for example, a stored association between a variant identifier and category identifier, a prediction as to whether or how a variant would change a function of a corresponding protein and/or other factors. In some instances, a particular variant has been previously associated with a definitive category (e.g., Pathogenic or Benign), and this category can be used for subsequent detections of the variant. In some instances, a particular variant has been previously associated with a non-definitive category (e.g., Likely Pathogenic, Likely Benign or Unknown), and this category can be used for subsequent detections of the variant or the category or the category can be reassessed.

If a variant has not been previously associated with a category or if a category is to be reassessed, an automated or semi-automated process may be used to identify a category for the variant. The automated or semi-automated process may use machine learning and/or a crawler of one or more data stores (e.g., a journal-article data store or particular journal data stores). For example, a crawler may detect addition of new research content objects at a data store and determine whether any of the research content objects correspond to a variant of one or more genes of interest. If so, an identifier of a given research content object (e.g., a link) can be tagged with an identifier of a gene of interest and an identifier of a variant. The research content object can be semantically assessed to automatically generate a category for the variant, or an identifier of the research content object may be presented as being potentially relevant at a reviewer device when a reviewer is involved in a categorization.

A given sample may correspond to a set of detected variants, and a category may be assigned to each of the set of detected variants. Reports to a client can be generated based on the variant categories. In one instance, a template is selected based on an extremum category along a pathogenic scale. For example, all available categories may be ordered along a scale, and a category at a highest position along the scale can be identified for a given sample. To illustrate, an extremum category may be identified as being "Pathogenic" if a sample includes any variants assigned to a Pathogenic category, while an extremum category may be identified as being "Likely pathogenic" if a sample includes at least one variant assigned to the Likely Pathogenic category but none to the Pathogenic category. In some instances, one available category is an "Unknown" category. An unknown category may, but need not, be positioned along the scale. For example, it may be positioned such that it is to be an extremum category if no Likely Pathogenic or Pathogenic categories are detected but an Unknown category is.

As an example, a report template for an instance where a set of variants included a Pathogenic variant may include a communication form or text for informing others of the risk factor. As another example, a report template an instance where a set of variants included an Unknown variant may include a communication form or text encouraging family members to participate in genetic screening to potentially further assess the unknown variant.

A report can be generated based on a report template and genetic data (and, in some instances, other data). The report may identify one, more or all variants detected and their corresponding categories. The report may include identifications of one or more research content objects that support a categorization of a variant and/or provided further information about a variant. In some instances, such content-object identifications are not presented in an initial view of a report but may be presented in response to, for example, detection of an interaction with the report that corresponds to a request for such information.

In some instances, a report includes a result or is based on a result of an analysis not previously requested by or on behalf of a client. For example, an external assessment system or assessment system may have performed an analysis on each of a set of genetic data so as to identify data sets corresponding to a particular profile. The particular profile may correspond to a risk variable indicating a likelihood, for example, of developing a given condition. As another example, an analysis may identify a predicted result of a potential action (e.g., taking a particular medication or having a child with another client or famous person). In some instances, rather than including the result the report identifies a type of result that may be provided (and/or generated) upon request.

In some instances, assessment system 105 evaluates genetic data in combination with other types of data in order to generate a risk analysis result. In one instance, an initial evaluation involves detecting whether, for each data type, the data includes an abnormal data element (e.g., as evaluated with respect to the human species or a particular population). For example, assessment system 105 may identify whether genetic data includes any variants with respect to genes of interest, or assessment system 105 further evaluate a medical history (e.g., as provided by a physician) to determine whether the client had a prior cancer diagnosis. As another example, a family history may be evaluated to determine whether an above threshold number of relatives were diagnosed with cancer or whether a close relative was diagnosed with cancer prior to a threshold age. As yet another example, data from a wearable device may be assessed to determine whether a client is not meeting a threshold for exercise and/or for sleep or to determine whether a client is outside more than a threshold percentage of time.

Each one of these abnormalities may be individually associated with some increased risk for being diagnosed with a condition, such as cancer. These associations may be identified via a local or remote look-up table. Assessment system 105 may aggregate the data in any of a variety of manners. For example, assessment system 105 may identify a maximum (quantitative or categorical) risk variable associated with each of two, more or all data types, or assessment system 105 may generate a weighted sum of risk variable. As another example, a protocol for how to generate an overall risk variable based on a combination of abnormality data based on a machine-learning or cluster protocol.

In some instances, a risk associated with a particular abnormality (e.g., variant) and/or with a combination of abnormalities is unknown or is associated with a below-threshold confidence. Upon detecting such an abnormality or combination (or a threshold quantity thereof), the particular abnormality and/or combination can be identified in a review-request communication and sent to a reviewer device 170. Reviewer device 170 may then present the identification to a reviewer 175 and detect input that is indicative of an estimated risk to associate with the abnormality and/or combination.

One or more review-request communications can include representations of pertinent genetic data, results from application of one or more machine-learning techniques, identifications of one or more potentially relevant research content objects, and/or one or more questions. For example, a review-request communication can identify a variant and information about the variant, such as a corresponding gene, type of variant and position within the gene. The communication may further include predictions generated based on one or more machine-learning techniques, such as a prediction as to whether the variant will affect a function or structure of a corresponding protein. A machine-learning technique can include a semantic-analysis technique that, for example, searches for words and/or phrases pertaining to potential variant impacts and assigns weights to associated potential predictions based on a distance between any identified word and an identifier of a variant and/or whether the word or phrase is separated from an identifier of the variant with a negative word. A machine-learning technique can also or alternatively include a modeling technique that models how a variant will impact a corresponding protein.

As another example, a review-request communication may include an identifier of each of one or more research content objects that pertain to a variant. The identifier may include, for example, a citation (e.g., identifying an author, journal, title and/or year) and/or a link to the content object. Each of the one or more research content objects may relate to (or potentially relate to) a study of a prevalence of a variant, an impact of a variant on a gene function, an impact of a variant on a protein function or structure, etc.

In some instances, a review-request communication organizes data (e.g., genetic data, machine-learning results, research content object identifications and/or objects) into one or more presentations. For example, in one instance, each of one or more review-request communications corresponds to a webpage. In some instances, reviewer device 170 organizes data for local presentation.

A presentation may, for example, include a simultaneous identification of genetic data (e.g., identifying a gene and variant) and/or one or more questions (e.g., identified via a categorization workflow). A same or different presentation may include identifications of one or more research content objects, which may potentially relate (for example) to a question in the one or more questions (e.g., as determined based on a semantic analysis).

A presentation may be dynamic and/or interactive. For example, a display may be updated based on what input was received from a reviewer device. The update may include, for example, presenting new questions or identifications of research content objects.

Input provided by a reviewer 175 at reviewer device 170 can include an answer to one or more questions. An answer may include, for example, a yes/no answer, selection amongst a set of options or a number. In some instances, at least one (or all) question or answer may require or may permit indication as to why a given answer was provided. The indication may include, for example, text, selection of one or more (previously identified) research content objects, identification of another research content object (e.g., via provision of a citation or html link) or selection amongst one or more support options (e.g., research article, data analysis, etc.).

In some instances, input provided at reviewer device 170 includes identification of a category. In some instances, input provides information that may be used to identify a category. For example, answers to one or more questions in a categorization workflow may indicate to which category a variant is to be assigned without explicitly identifying the category.

In some instances, multiple reviewers 175 are involved in categorizing a variant. For example, a first reviewer may provide an initial assessment of a variant (e.g., identifying answers to one or more questions, identifying one or more research content objects as being pertinent to a question or categorization, and/or characterizing one or more research content objects). A second reviewer may then repeat the assessment or review the first reviewer's initial assessment to determine whether the second reviewer agrees with the provided inputs.

When multiple reviewers are involved, it may be that it is required (for example) that the two reviewers agree in the entirety of the assessment (e.g., all answers and/or support identifications), agree with respect to at least some of the assessment (e.g., pertaining to particular questions), or provide assessments that result in a same categorization. In one instance, one of the review assessments can be performed based on machine learning. For example, answers to one or more questions may be provided based on a semantic analysis of one or more research content objects.

A result generated by assessment system 105 can include a quantitative or qualitative (e.g., categorical) risk variable. For example, the risk variable may include a percentage probability or range of getting a particular condition. As another example, the risk variable may include three risk categories (low risk, moderate risk, and high risk).

Assessment system 105 may generate an electronic report that includes the result and/or that is selected based on the result. For example, different preventative-measure content may be included in reports depending on a risk category. As another example, a report may identify one or more abnormalities (e.g., one or more variants) and/or corresponding normal bases, ranges, data and so on. A report may identify a condition (e.g., disease) pertaining to an analysis (e.g., "Breast Cancer Risk Analysis"). A report may identify types of data (e.g., particular genes and/or other type of data) used in the analysis. A report may identify a confidence in a result (e.g., a risk variable). A report may identify a recommendation (e.g., to consult with a physician or to receive a particular medical test).

A report may include identifications of one or more research content objects or databases relied upon to arrive at a category (e.g., a pathogenic or likely pathogenic category) of a particular variant. Such content-object identifications may be provided, for example, upon detecting client input requesting identification of the support or automatically.

In some instances, a report must be approved (e.g., by a physician 115b or pathologist) before it is transmitted to a client device 130. A report-reviewing interface may, but need not, include a configuration to allow a reviewing entity to change or add to the report. A report-reviewing interface may further allow (or require) a reviewing entity to identify a time at which to send the report to a client.

Assessment system 105 may update and may have access to a variety of data stores, part or all of which may be remote from, co-localized with assessment system 105, and/or included in assessment system 105. One or more of the data stores may include a relational data store, such that data from one data store or structure within a data store may be used to retrieve corresponding data from another data store or structure.

Each of one or more of the data stores may be associated with one or more access constraints. Access constraints applicable to a given data store may be stored as part of the data store or separately (e.g., in an access control data store). Access constraints that apply to one type of data may differ from access constraints that apply to another type of data. For example, account and user data may be associated with stricter access constraints than results data, to make it more difficult for a user, developer or hacker to be able to link genetically tied data to a particular individual. An access constraint may identify one or more individuals, devices, systems, and/or occupations permitted to access some or all data in a data store. An access constraint may include a rule, such as one that indicates that a user is permitted to access data pertaining to any of a group of clients that the entity was involved in with respect to a sale of a kit or the any low-level authorized user is permitted to access deidentified data but not identifiable data and a high-level authorized user is permitted to access all data. As another example, access constraints may indicate that process data is to be hidden from external developers and available to internal users; that genetic and epigenetic data is to be made available to all authorized external developers and internal users; and that client data is to be availed to authorized internal users and only availed to external developers to the extent to which each corresponding clients represented in the data is a client of the developer (e.g., and that the client authorized such data access).

When different access rights apply to different types of data, a query protocol can be established to address instances where a query relates to each type of data. For example, a query may request Variable X for each client corresponding to Data Y, and Variable X and Data Y may correspond to different access constraints. As another example, a query may request a count of clients for which both Data Y and Data Z was detected, and Data Y and Z may correspond to different access constraints. One example of a query protocol is to use a most restrictive overlap of data constraints applying to the query. Another example of a query protocol is to permit use of an at least partly more relaxed access constraint so long as it relates to defining a client set or condition and not to results to be returned or processed.

In some instances, an access constraint is configured to inhibit an identification of particular data (e.g., client identity). Such a constraint may relate to a precision of requested data. To illustrate, a constraint may be configured to permit a user to request and receive data identifying client locations, so long as the request is configured to not request too specific of a location and/or so long as the request corresponds to a number of client data elements sufficiently large to obscure (e.g., in a statistical result) a precise location. Compound queries may be more sensitive to potential identification concerns, such that one or more access constraints are configured to permit access to less precise data when multiple data elements are being requested.

The data stores may include, for example, an account data store 176, which may include login credentials for one or more users and/or types of data access to be granted to each user; process data store 177, which may identify laboratory analysis characteristics pertaining to particular data elements (e.g., identifying a laboratory, piece of equipment and/or processing time); genetic data 178, which may identify one or more genetic sequences associated with a given sample or client; and/or epigenetic data store 179, which may identify one or more epigenetic sequences or signatures associated with a given sample or client. The data stores may further or alternatively include a results data store 181, which may identify one or more abnormalities identified by and/or one or more results generated by assessment system 105 that are associated with a given sample or client.

The data stores may further or alternatively include a reports data store 182, which may include one or more report templates (e.g., each associated with one or more result types) and/or one or more reports to be transmitted or having been transmitted to a client device; and/or a relevance support data store 183, which may identify which types of data (e.g., genes, genome portions, activity patterns, inputs, medical records, medical tests, etc.) are established to be, potentially, established not to be, or unknown whether to be relevant for evaluating a particular type of risk (e.g., a risk of developing a particular condition).

Relevance support data store 183 may include identifications of one or more research content objects. The identifications may include, for example, web addresses, journal citations or article identifiers. In some instances, an identification identifies one or more sources associated with the research content object (e.g., scientist, author, journal or data store). Research content objects may be tagged with one or more tags, which may identify (for example) a variant, a gene, and/or a type of assessment. In some instances, each of one or more research content objects are associated with a score which may reflect a credibility of the content object. The score may be based, for example, on a publication frequency of a source, an impact factor of a source, a date of publication of the content object, and/or a number of citations to the content object.

Genetic assessment network 100 can also include a user device 180 configured to detect input from a user 185. User 185 may be associated with an account or other authentication data indicating that access to some or all of the data is to be granted. Accordingly, user 185 may be able to interact with various interfaces (presented at user device 180) to view data pertaining to one or more particular clients (e.g., in an identified or deidentified manner), to view summary data that relates to data from multiple clients, to explore relationships between data types, and so on. In some instances, an interface may be configured to accept inputs from a user 185 so as to enable the user to request data pertaining to samples with variants in particular genes; particular variants; particular phenotypes or condition risks; ethnicity information; trait information; symptom presence; and/or family-history patterns.

In some instances, data transmitted from assessment system 105 to user device 180 can relate to workflow processing time periods. Specifically, as can be appreciated by disclosures included herein, generating outputs for clients and/or physicians can involve multiple steps, each of which can include a task of an entity and/or device. Completion times of individual tasks can then be tracked and assessed. A workflow can include a structure and definition for these tasks. For example, one workflow can include some or all of the following tasks:

Inputs collected at client device 130 and conveyed to assessment system 105 that correspond to a preliminary request to conduct assessment based on sample and ensure that all required inputs (e.g., which can include identifying and contact information, medical history, family medical history, payment information and/or identification of conditions for which risk variables are requested) have been received;

A same or different client device 130 (e.g., a wearable device) collects and transmits other data indicative of the client's activity or status;

Inputs collected at requestor device 110a, 110b and conveyed to assessment system 105 that corresponds to request for assessment for client;

Access control device 160b at physician-associated facility 120 collects and transmits medical record data of client;

Distribution device 135 alerted of new request and coordinates and confirms shipping of kit for sample collection to client;

Client 125 receives kit, collects sample and sends to laboratory 140;

Laboratory assessment device(s) 145 collect genetic and/or epigenetic data, and access control device 160a sends laboratory data to assessment system 105;

Assessment system 105 detects any variants in gene sequence(s) and/or any modifications in epigenetic sequence(s);

Assessment system 105 categorizes any variants and/or epigenetic modifications (e.g., as pathogenic, benign or unknown);

Reviewer device 170 collects inputs identifying a categorization of any variants and/or epigenetic modifications with an unknown category;

Confirmatory laboratory testing of any sample associated with a variant and/or epigenetic modification categorized as being pathogenic at same or different laboratory;

Assessment system 105 aggregates variant categorization data, medical-record data, client inputs and/or activity or status data and generates one or more risk variables;

Assessment system 105 generates electronic report with the one or more risk variables;

Reviewer device 170 and/or requestor device 110a collect inputs indicating that the electronic report is approved for transmission to client device 130; and Assessment system 105 transmits the electronic report to client device 130.

A workflow may include a task order that indicates that, for example, a first task is to be completed prior to performance of a second task, though a workflow may alternatively be configured such that at least some tasks may be performed in parallel. In some instances, one or more tasks in a workflow are conditional tasks that need not be performed during each iteration of the workflow. Rather, whether a conditional task is to be performed can depend on a circumstance, such as whether a result from a prior task is of a particular type or exceeds a threshold (e.g., such that confirmatory laboratory testing is only performed if a variant is detected and categorized as pathogenic and/or if a laboratory quality metric included in the laboratory data is below a threshold).

Using a workflow, assessment system 105 may track start and completion times of individual tasks during individual iterations of a workflow. Each iteration can correspond to generating a risk variable for a given client and may involve various other entities (e.g., physicians, reviewers, laboratories, etc.), which may be selected based on (for example) client preference, a geographical location of a client device and/or availability. For tasks performed at assessment system 105, start and completion times can be directly determined. For tasks performed by, at and/or via another device, assessment system 105 may track start and completion times via communications. For example, a start time may be identified as a time at which an instruction communication was sent from assessment system 105 and/or a time at which a communication was received indicating that the corresponding task was beginning. As another example, a completion time may be identified as a time at which a communication including a result of the corresponding task was received at assessment system 105 and/or a time at which a communication was received indicating that the corresponding task was complete.

Assessment system 105 may store task start and completion times (and/or task completion time periods, that being a difference between corresponding task completion and task start times) in process data store 177 in association with an identifier of the corresponding task and an identifier of a corresponding workflow iteration (e.g., an identifier of a client or sample). Assessment system 105 can collect task start and completion times that correspond (for example) to a given time period, laboratory, client group, analysis type, etc. and analyze the data at a population level. Through such analysis, assessment system 105 may identify average (or median or mode) completion time periods for individual tasks so as to identify tasks (or labs or entities) associated with workflow processing delay. Further or alternatively, assessment system 105 may identify backlog for individual tasks by identifying a number of "open" tasks for which a start time has been identified but no completion time is identified. Tasks (and/or labs or entities) associated with high backlog can then be identified.

Such task completion time monitoring can be performed automatically and/or in response to a query communication from user device 180. For example, assessment system 105 may determine, for each handling entity (e.g., laboratory, distribution device, reviewer, or physician) a portion of tasks completed by a first threshold time identified for a given task. Upon detecting that the portion exceeds a second threshold, an alert communication can be transmitted to user device 180 and/or a device of an associated entity. As another example, assessment system 105 may present a statistic (e.g., mean) corresponding to a processing time of each task in a workflow. The presentation may be interactive, such that more details about a statistic may be presented in response to a user selection of the statistic. For example, the statistic may be broken down by entity and/or task start time period, or more detailed information (e.g., a distribution or list of start and completion times) can be presented.

In some instances, data transmitted from assessment system 105 to user device 180 can relate to data queries received from user device 180. The query can, in some instances, include one that specifically or implicitly identifies one or more genes. For example, identification of a given kit or assessment may be associated with one or more genes. Assessment system 105 can identify genetic data that any access constraints indicate are accessible to the user, and present high-level population data. For example, assessment system 105 may identify a portion of clients for which any variant or a pathogenic variant was detected at each of the one or more genes. Such data can be presented in an interactive manner, such that a user can select a represented portion of the data to drill down into that data. For example, the interface may accept a selection of a representation of each gene, and the interface may be updated to identify a distribution of particular variants detected at the gene.

A drill-down may be configured to—at some level—begin representing non-genetic data. For example, a selection of a particular variant or gene may result in a display identifying a distribution of medical history data or demographic data from amongst clients associated with the particular variant or a variant at the gene. Thus, the drill-down can include retrieving data from different data stores depending on a level of precision. Further, each step in the drill-down may involve evaluating one or more applicable access constraints.

In some instances, a query may pertain to one or more genes, and query processing can include retrieving genetic data (or results derived therefrom) and retrieving epigenetic data (or results derived therefrom). For example, query processing may include identifying, for each subject and for each of the one or more genes, whether a genetic variant or an epigenetic modification was detected. A query result presentation may identify, for example, a portion of subjects for which a variant or modification was detected for each of the genes and/or a query result presentation may identify, for each of the one or more genes, a portion of subjects for which a particular type of variant or modification was detected. The presentation may again be configured to accept drill-down inputs so as to enable a user to further explore the pertinent data.

As another example, query processing may include identifying instances in which, in a given sample, both a genetic variant (e.g., generally or of a particular type) and an epigenetic modification (e.g., generally or of a particular type) was detected (e.g., generally, at a particular gene and/or at a particular position at a gene).

Genetic assessment network 100 can also include an external assessment device 190 configured to detect input from a developer 195. Via such inputs, external assessment device 190 may send electronic requests for genetic and/or other data (e.g., relating to particular genes, a particular client and/or particular client inputs) to assessment system 105. The inputs may be received, for example, via a webpage or app page, which may identify general types of data that is available for restricted access. Assessment system 105 may evaluate the request to determine, for example, whether a corresponding client 125 authorized such access (which may be verified via a communication exchange between assessment system 105 and client device 130) and/or whether such access is relevant to a purported type of analysis.

The evaluation can include assessing one or more permissions associated with a given client. In various instances, a permission may be set to be conditioned upon an entity or system transmitting a request, a type of data being requested, a size of data being requested or a potential type of processing identified as being a use for the data. For example, a client may specify that an external assessment device can be granted access to genetic data that includes sequences (or variant detections) if the requested data pertains to fewer than a first threshold number of genes; that access to genetic data that includes variant detection can be granted if the requested data pertains to fewer than a second threshold number of genes, and that access to genetic data is to be otherwise denied.

Whether an evaluation is to be granted may depend, in part, on whether a system or entity associated with a request has provided any data previously or presently and/or what type of data is being provided. For example, external assessment devices and/or associated systems may provide genetic data (e.g., generated from an external laboratory and/or client sample), results data, epigenetic data, input data and/or medical test or history data.

Whether an evaluation is to be granted may depend on one or more permissions associated with a request. The permissions may be set, for example, based on client input (or lack thereof) and/or based on which type of analysis and/or data storage was initially agreed to by a client. For example, an interface may be configured so as to enable a client to permit or refuse storage of particular types of data (e.g., sequences and/or variant detection beyond what is needed to perform a requested analysis); permit or refuse sharing data to one or more other entities (e.g., generally, of a given type or specific entities); and/or permit or refuse using data to perform one or more other types of analyses. Permissions pertaining to whether various analyses may be particularly important given that rules or regulations may require particular results of analyses to be transmitted to a client. Thus, if such information is not desired, analyses must be restricted.

In some instances, an interface may be configured to enable a client to specify a degree of identification to be associated with data of the client with regard to storage and/or distribution. For example, a client may be able to indicate that genetic data and/or results are to be associated with a pseudo-randomly generated unique identifier of the client rather than client identifying information. As another example, a client may be able to indicate that data is to be stored so as to require a key for access, which may be held by the client. As another example, a client may authorize transmission of the client's data to external assessment devices so long as identifying information of the client (e.g., name, email, address, social security number, phone number, and so on) is not provided without subsequent explicit permission.

In some instances, a same or different permission may be established to apply to other type of data (e.g., with regard to storage and/or distribution), such as data from health records (e.g., identifying a lipid profile), client inputs and/or sensor data (e.g., identifying a heart rate or average number of steps walked per day). In some instances, a same or different permission may be established so as to relate to data collected from external systems. For example, a permission may indicate whether an assessment system is authorized to request data (and/or what type of data) from a physician system, an external assessment device, etc. and/or how an assessment is to handle results provided by an external system.

If the evaluation indicates that access is to be granted, assessment system 105 may (for example) send an instruction communication to laboratory 140 to conduct a new analysis of an existing sample, send a data request to a device (e.g., access control device 160b, client device 130) and/or retrieve data from a data store (e.g., and extract pertinent information from any larger data structure, such as extracting gene-specific data from a genome). When part or all of the data is accessible, one or more communications may be transmitted to the developer. The one or more meetings may include the data and/or may include information (e.g., login information or ftp information) to enable the developer to access the data. In some instances, other data different from that which was requested may be provided. The other data may include, for example, quality control metrics of the provided data, other data determined to be relevant to an analysis, and/or other data that is being provided in lieu part or all of data that had been requested.

Provision of such data may be conditioned upon or may require payment (e.g., by a client or developer) of a fee. A fee may depend on one or more characteristics pertaining to the request or request handling, such as (for example) a type and/or size of data being requested (e.g., such as which genes, whether a sequence or variant detection is requested, whether identifiable or de-identified data is being requested, etc.), a type and/or size of data being provided in response to the request, whether all of the data being provided was already stored in a data store managed by assessment system 105 (or whether a new lab request or data request was sent to secure the data). A fee may depend on one or more characteristics pertaining to a developer (and/or associated system or entity) having submitted the request, such as (for example), how many requests the developer previously submitted, whether the developer has provided any data pertaining to one or more new or existing clients, whether the developer has indicated that results of an analysis will be returned, and/or an estimated credibility of the developer (e.g., in terms of a confidence that data provided to the developer will not be transmitted to other systems and/or that data provided by the developer is accurate). A fee may depend on any previous or potential fee to be charged to a client (by assessment system 105 or via a device associated with the developer) in association with an analysis. For example, a fee to a developer may be higher if the developer is being paid to perform an analysis and/or a fee to a developer may be lower if an analysis has a potential to lead to subsequent client payment.

Various devices in genetic assessment network 100 may communicate with one or more other devices in genetic assessment network 100 via a network, such as the Internet, a local-area network or a short-range network. Communications may be sent in a secure manner to, e.g., inhibit unauthorized access to health data. Techniques such as token authentication and/or encryption may be used.

It will be appreciated that the representations of devices and configurations depicted in FIG. 1 are illustrative. For example, while a single laboratory 140, client device 130, and genetic data store 178, etc. are shown, a system may include multiple laboratories 140, client devices 130, genet data stores 178, etc. As another example, while access control devices 160a, 160b are shown as being connected to laboratory data store 155 and EMR data store 165, additional access control devices may be present in system 100. For example, an access control device may be included within or connected to assessment system 105 so as to control access that requestor device 110b, client device 130, distribution device 135, reviewer device 170, user device 180 and/or external assessment device 190 may achieve.

Figure 2:
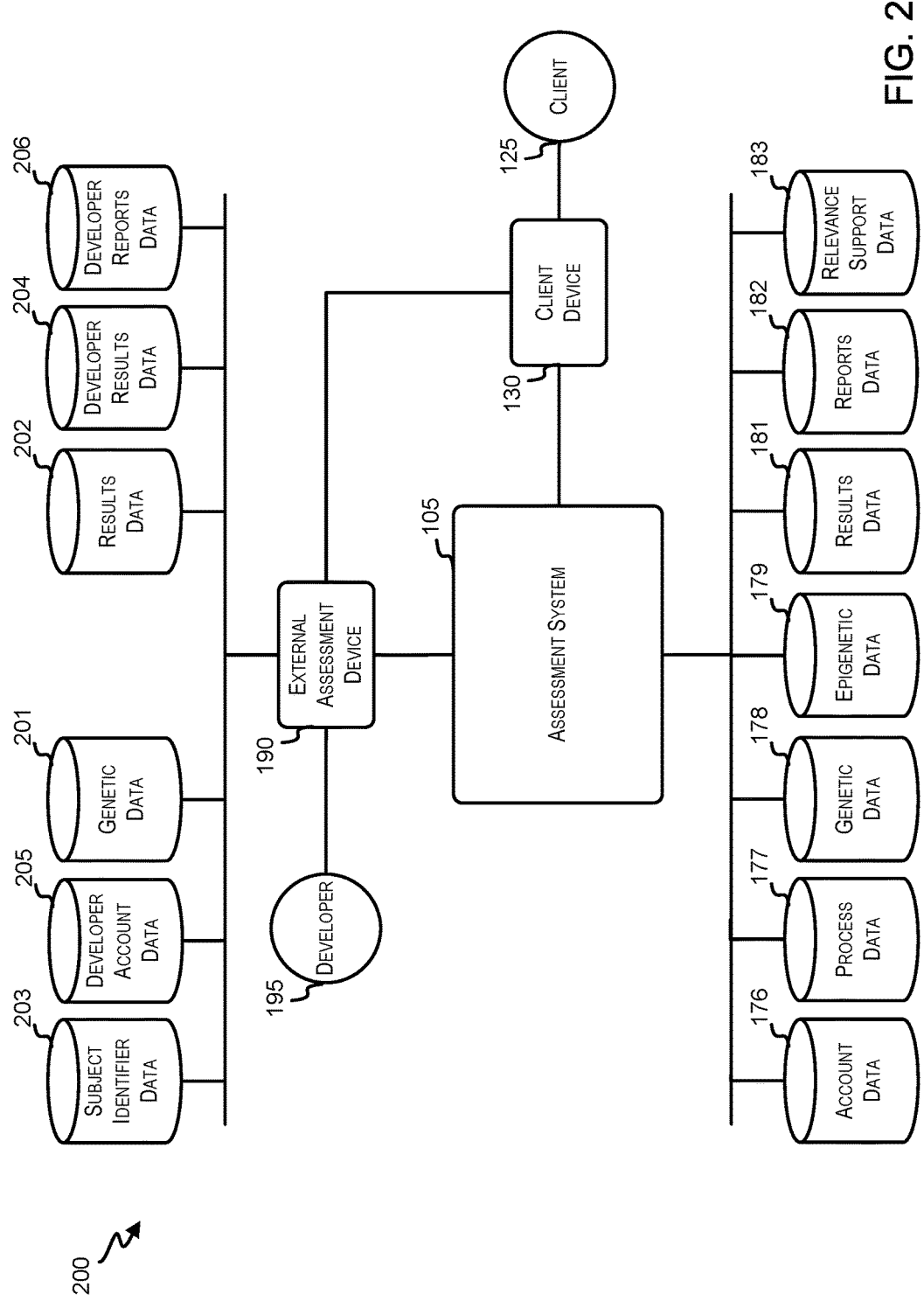
FIG. 2 shows another genetic assessment network in one embodiment.

Referring next to FIG. 2, another genetic assessment network 200 is shown in one embodiment. It will be appreciated that various disclosures herein relating to genetic assessment network 100 and/or genetic assessment network 200 may be combined. For example, while FIG. 2 does not depict a laboratory 140, one embodiment of a genetic assessment network may include some or all of the components depicted in FIG. 2 along with a laboratory.

As depicted in FIG. 1, genetic assessment network 200 includes assessment system 105, client device 130, external assessment device 190 and various data stores 176-183. However, the depicted instance also shows external assessment device 190 have access to various third-party data stores. One or more of these data stores may, at least in part, mirror parts of data stores managed by and/or accessible to assessment system 105. One or more of these data stores may be based on data-collections or analyses performed by the external system.

For example, external assessment device 190 may be configured to access, update and/or manage one or more of a genetic data store 201, results data store 202, subject identifier data store 203, developer results data store 204, developer account data store 205, and/or developer reports data store 205.

Genetic data store 201 may include, at least in part, genetic data that corresponds to that in genetic data store 178. For example, external assessment device 190 may submit a request for genetic data to assessment system 105, and assessment system 105 may retrieve and transmit genetic data from genetic data store 178, such that external assessment device 190 may initiate storing the data in genetic data store 201. Thus, for example, genetic data store 201 may include one or more sequences for each of one or more clients. In some instances, genetic data store 201 may include one or more additional sequences for one or more clients and/or may include one or more sequences for one or more additional clients. This additional data may be shared, for example, with assessment system 105 upon request from assessment system 105, in a data exchange or locally maintained.

Results data store 202 may similarly include, at least in part, results data that corresponds to that in results data store 181. For example, assessment system 105 may transmit results that identify variants detected in a sequence of a client and/or a risk variable of a client.

Subject identifier data store 203 may include data provided by assessment system 105 that can be used for partial or full identification of a client associated with a client. The data may include, for example, some data that mirrors that from account data store 176 and/or a name or contact information of a client and/or one or more characteristics of a client. In some instances, the data includes an identifier that can be used to (e.g., at assessment system 105) to particularly identify a client but that does not include, for example, personal or identifying information. For example, data may associate an array index corresponding to particular genetic data and/or results data with a pseudorandomly generated identifier of a client. The identifier may then be used in any subsequent communication with assessment system 105 so as to convey what client and/or data set is being referenced. For example, external assessment device 190 may transmit a communication to assessment system 105 that indicates that an analysis of genetic data of a client corresponding to a given identifier is at risk for a particular condition and/or is predicted to respond well to a therapy or medication. Assessment system 105 may use the identifier, for example, to query account data store 176 to identify contact information for the client to alert them of the result.

One or more data stores may include data generated at the external system. For example, developer account data store 205 may include other information pertaining to a particular client. For example, prior to or after receiving information pertaining to a client, an external system may communicate with a device of the client or another system with access to client information. Developer results data store 204 can include one or more results generated by the external system using, for example, genetic data provided by assessment system 105 or otherwise collected. The results may include, for example, a variant detection, risk variable or prediction variable (e.g., predicted medication efficacy). In some instances, a developer result may be transmitted from external assessment device 190 to another device, such as assessment system 105 and/or client device 130. Whether the result is transmitted to client device 130 may depend, for example, on whether identifying information for a client is available to the external system. In some instances, a result is communicated as part of a report. A report may be generated using, for example, developer report data from developer report data store 206, which may include (for example) one or more report templates.

Figure 3:
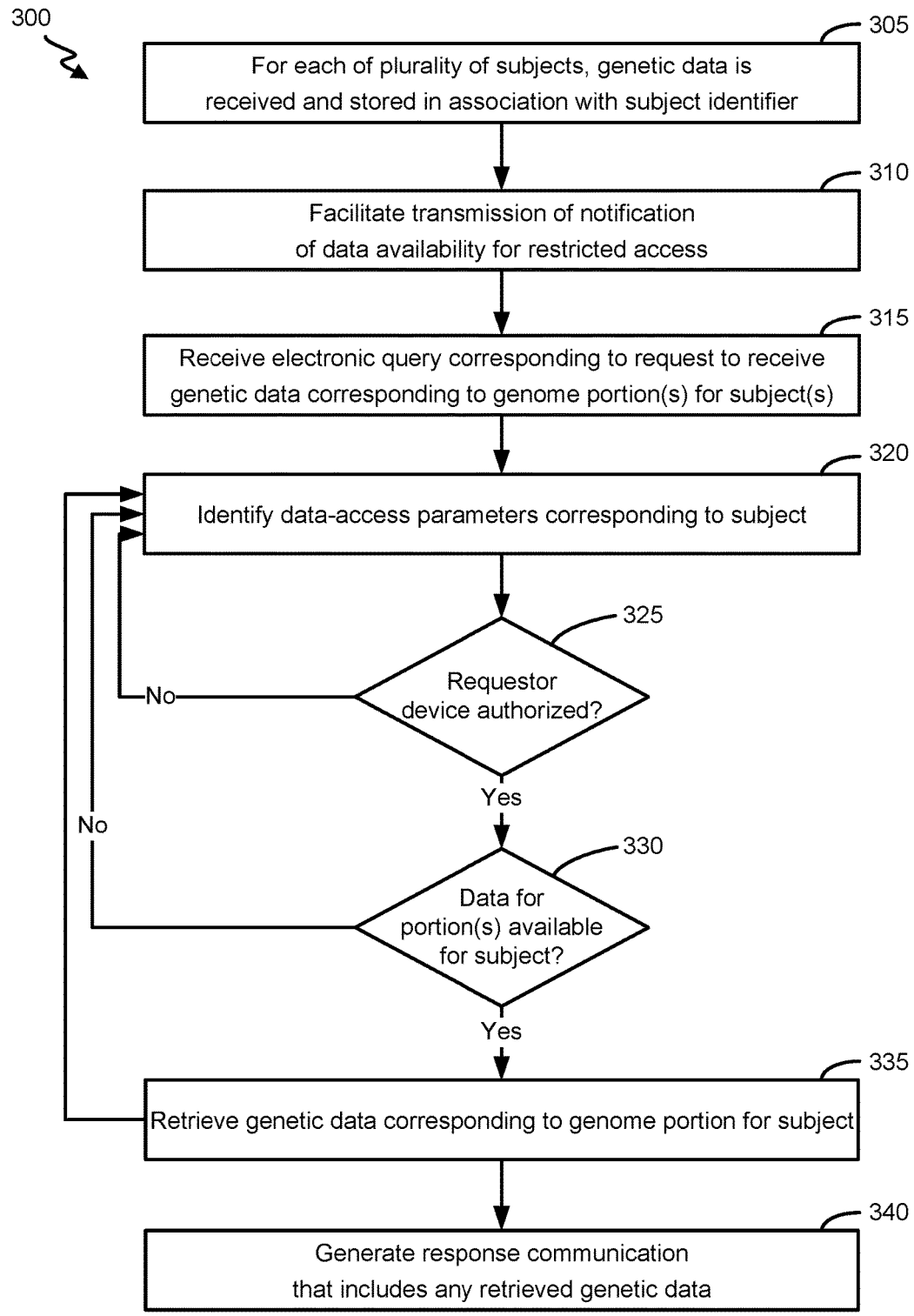
FIG. 3 shows an embodiment of a process for processing requests from requestor devices for data access.

Referring next to FIG. 3, an embodiment of a process 300 for processing requests from requestor devices for data access is shown. Process 300 may be performed in part or in its entirety by, for example, assessment system 105. At block 305, for each subject of a plurality of subjects, genetic data is received and stored in association with an identifier of the subject. The genetic data may be collected from (for example) one or more laboratory devices and/or other sources (e.g., external systems, such as ones participating in a data-share interaction). The genetic data may include, for example, an aligned or unaligned sequence or other data, such as variants that are detected.

At block 310, a transmission of a notification is facilitated. The transmission can be to each of a plurality of potential requestor devices. The notification can indicate that subjects' genetic data is available for restricted access. The notification can identify, in some instances, one or more specified types of genetic data that are available (e.g., corresponding to a specification of each of one or more genes, chromosomes or variants). The notification may be transmitted via, for example, part of a webpage or app page or as a communication such as an email or message.

At block 315, an electronic query from a requestor device is received. The electronic query can correspond to a request to receive requested genetic data corresponding to one or more portions of the human genome for each of one or more subjects of the plurality of subjects. The electronic query can identify the one or more portions specifically (e.g., by identifying one or more particular genes) and/or implicitly (e.g., by identifying a type of analysis, such as an analysis pertaining to a risk of developing of a particular condition pertaining to the one or more portions) The electronic query may be received from, for example, an external assessment device and/or a device to which the notification was transmitted. Blocks 320 through 335 can then be iteratively or concurrently performed with respect to each subject in the one or more subjects.

At block 320, for a subject in the one or more subjects, one or more data-access parameters are identified. The data-access parameters can correspond to those identified, for example, via rules (e.g., indicating that access is to be granted to a requesting entity) or inputs by a subject (e.g., identifying one or more entities or types of entities to be granted or denied access). The data-access parameters may relate, for example, to whether the client has authorized sharing its genetic data with any entity or system, which types or which entities or systems the client's data is authorized to be shared with, in which circumstances (e.g., time periods and/or for particular types of analyses) a client's genetic is authorized for sharing, and so on. A data-access parameter may relate to which genetic data (e.g., pertaining to which genes and/or sequences versus detected variants) and/or a quantity of genetic data is authorized for sharing. A data-access parameter may include a condition for sharing, such as authorizing sharing if a result of an analysis is returned to the client. A data-access parameter may include a use constraint, such as authorizing or prohibiting data sharing for analyzing a risk of developing cancer but not dementia. A data-access parameter may include a privacy constraint, such as authorizing data sharing so long as it is shared in an anonymized, partly de-identified or completely de-identified manner.

At decision block 325, a determination is made as to whether the requestor device is authorized to receive the requested genetic data corresponding to the one or more portions of the human genome for the subject. The decision may be based, for example, on an identity of the requestor, a characteristic of the requestor, a type of analysis identified as one to be performed by the requestor, a degree of data security provided by the requestor, an agreement of returning results by the requestor, and so on.

When it is determined that the requestor device is authorized to receive the requested genetic data corresponding to the one or more portions of the human genomic for the subject, process 300 continues to block 330 where it is determined whether the requested genetic data corresponding to the one or more portions of the human genome for the subject has been stored in the data store.

When it is determined that the requested genetic data corresponding to the one or more portions of the human genome for the subject has been stored in the data store, process 300 continues to block 335 where the genetic data corresponding to the one or more portions of the human genome for the subject from the data store is retrieved.

At block 340, a response communication is generated. The response communication can include any retrieved data corresponding to the one or more portions of the genome for any of the one or more subjects for which the affirmative determinations were reached at blocks 325 and 330. In some instances, the response communication does not itself include the retrieved data but otherwise facilitates access to the data. The response communication may, but need not, include a client identifier and/or client information pertaining to each provided genetic set. Thus, for example, in various instances, a requestor may then be able to identify clients with data matching a given profile to assessment system 105 and/or in a manner so as to be able to communicate with them directly. Whether and/or how a client is identified in the response communication may also depend on a data-access parameter.

Figure 4:
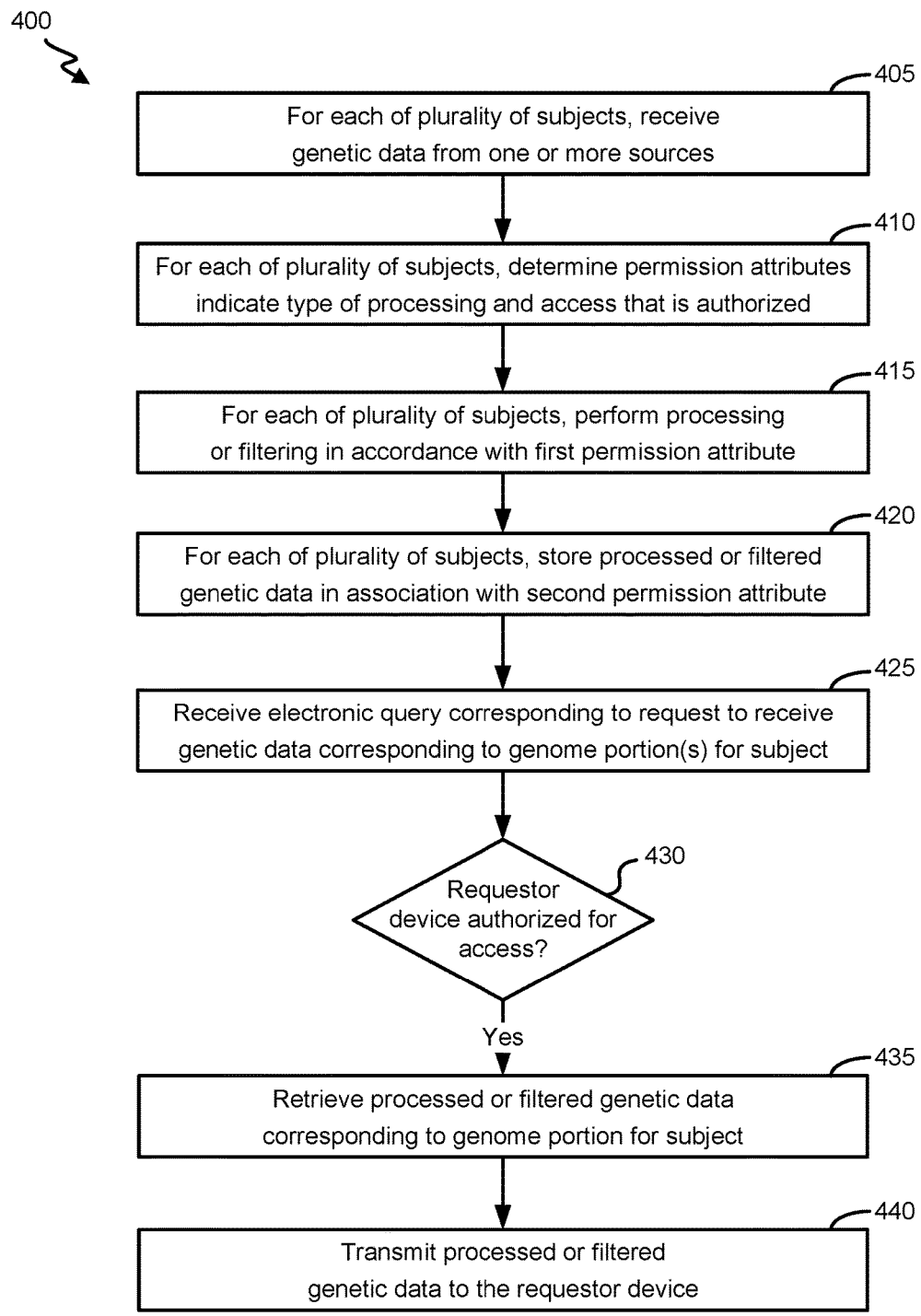
FIG. 4 shows an embodiment of a process for processing requests from requestor devices for data access.

Referring next to FIG. 4, an embodiment of a process 400 for processing requests from requestor devices for data access is shown. Process 400 may be performed in part or in its entirety by, for example, assessment system 105. At block 405, for each subject of a plurality of subjects, genetic data is received from one or more sources. The genetic data may include, for example, a sequence and/or variant data that indicates whether any variants were detected and, if so, which variants were detected and/or their classification. The one or more sources may include, for example, a laboratory and/or external system.

At block 410, a first permission attribute and a second permission attribute corresponding to the genetic data are determined. The first permission attribute can indicate a type of processing that is authorized. The second permission attribute can indicate a type of access of the genetic data that is authorized. For example, the second permission attribute can indicate with entities or systems can access the data and/or what types of the genetic data can be accessed (e.g., generally or by particularly entities or systems or types of entities or systems). For example, the second permission attribute may indicate whether full sequences can be accessed, particular variants can be accessed and/or an indication of whether a variant was detected (e.g., and a corresponding location) can be accessed.

At block 415, a processing or filtering of the genetic data is performed in accordance with the first permission attribute. The processing may include, for example, extracting particular portions of the data (e.g., corresponding to particular genes) and/or detecting variants on the genome. Thus, for example, block 415 may include identifying which genes are authorized to be analyzed (e.g., via specific gene-identifying inputs from a client and/or or via implicit identification subsequent to client identification of a type of analysis to be performed). Variants may then be detected and classified for those genes.

At block 420, in one or more data stores, the processed or filtered genetic data is stored in association with an identifier of the subject and the second permission attribute. The identifier may include, for example, a name, email address, IP address, and/or phone number of a client and/or an identifier generated by assessment system (e.g., using a pseudo-random or counting technique).

At block 425, an electronic query is received from a requestor device. The electronic query can correspond to a request to receive requested genetic data corresponding to one or more portions of the human genome for a subject of the plurality of subjects. The electronic query may, but need not, particularly identify the subject. For example, the electronic query may include a name, social security number of other identifier of a subject; the electronic query may identify a characteristic of a subject (e.g., so as to indicate that data is requested for each subject associated with the characteristic); or the electronic query may not include any subject-identifying aspect (e.g., so as to indicate that data is requested for each subject with available data).

At block 430, it is determined, based at least in part on the second permission attribute associated with the subject and an entity or characteristic associated with the requestor device, whether the requestor device is authorized to access the requested genetic data associated with the subject and corresponding to the one or more portions of the human genome.

When it is determined that the requestor device is authorized to access the requested genetic data, process 400 proceeds to block 435 where the processed or filtered genetic data is retrieved from the one or more data stores that corresponds to the requested genetic data. At block 440, the processed or filtered genetic data is transmitted to the requestor device. The genetic data may be transmitted in an identifiable, de-identified, and/or anonymous manner. The genetic data may be transmitted in an encrypted manner. In some instances, the genetic data may be made accessible and may require a requestor to use, e.g., a key, token or access code for access. One or more use constraints may also be sent to the requestor device.

Figure 5:
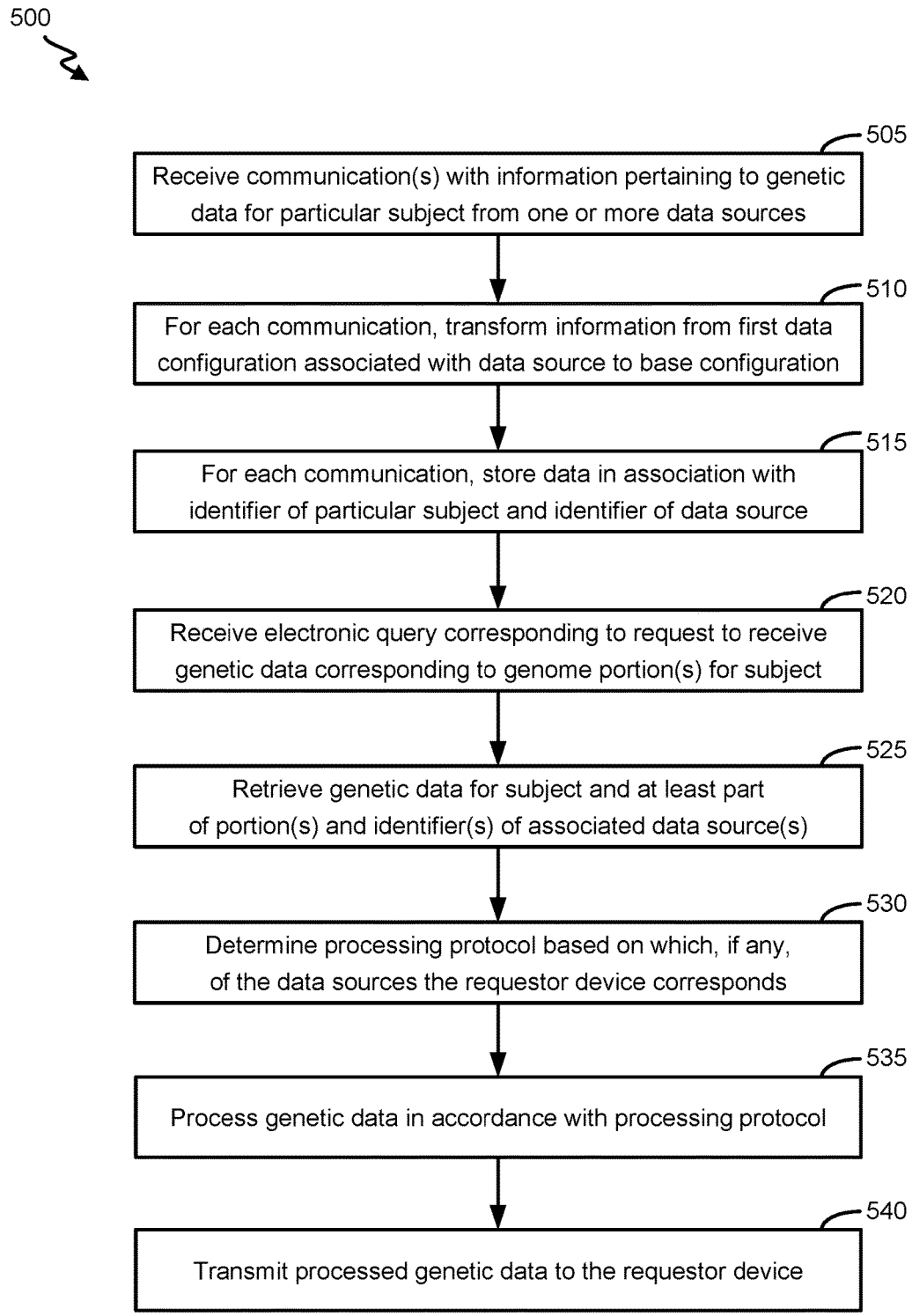
FIG. 5 shows an embodiment of a process for processing requests from requestor devices for data access.

Referring next to FIG. 5, an embodiment of a process 500 for processing requests from requestor devices for data access is shown. Process 500 may be performed in part or in its entirety by, for example, assessment system 105. Process 500 begins at block 505 where, for each of one or more data sources, one or more communications are received that include information pertaining to genetic data for a particular subject. The one or more data sources can include one or more data sources determined to be credible. For example, a determination can be made, with respect to each data source of a plurality of data sources, as to whether the data source is credible. If so, a communication channel may be established to as to receive information from the source. The received data may include, for example, one or more sequences and/or variant data (e.g., a type, position and/or classification of one or more variants).

At block 510, for each received communication, the information is transformed from a first data configuration associated with the data source to a base data configuration. For example, the first data configuration and the base data configuration may differ with respect to an alignment technique, variant-detection protocol, variant-classification protocol and/or degree of precision. At block 515, for each received communication, the transformed information is stored in one or more data stores in association with an identifier of the particular subject and another identifier of the data source.

At block 520, an electronic query is received from a requestor device that corresponds to a request to receive genetic data corresponding to one or more portions of the human genome for the particular subject. The requestor device may be associated with, or not associated with, one or more of the data sources. In various instances, the requestor device may be one that provided data pertaining to one or more other particular subjects. The electronic query may include a specification of the one or more portions (e.g., one or more genes) explicitly or implicitly. In some instances, the request is for all genetic data available for the subject. The electronic query may include one that is for genetic data pertaining to multiple subjects and/or that does not specifically identify the subject (e.g., but may instead identify a subject characteristic).

At block 525, genetic data is retrieved from the one or more data stores. The genetic data can be retrieved in response to a query of the one or more data stores with the identifier of the particular subject (and/or characteristic thereof) and with one or more specifications of the one or more portions of the human genome. The retrieved genetic data can include data associated with the particular subject and with at least part of the one or more portions of the human genome. An identifier of each of one or more data sources of the plurality of data sources that provided information for the genetic data associated with the particular subject and with at least part of the one or more portions of the human genome is also retrieved at block 525.

At block 530, a processing protocol for processing the genetic data is determined. The processing protocol can be determined based on, for example, a determination as to which, if any, of the one or more data sources the requestor device corresponds. For example, if the requestor device corresponds to one or more of the data sources having provided at least some genetic data for the subject, identifying information of the subject may be preserved, whereas the data may otherwise be de-identified. As another example, any part of the retrieved data provided by a source associated with the requestor device may be provided in full while other data parts may be processed (e.g., so as to provide only variant detections and/or variant classifications). As yet another example, any part of the retrieved data provided by a source not associated with the requestor device may be processed and/or released in accordance with any data restrictions specified by the other source.

At block 535, the genetic data is processed in accordance with the processing protocol. At block 540, the processed genetic data is transmitted to the requestor device. The genetic data may be transmitted, for example, as part of a webpage or app page and/or via an email, message or secure transfer.

Figure 6:
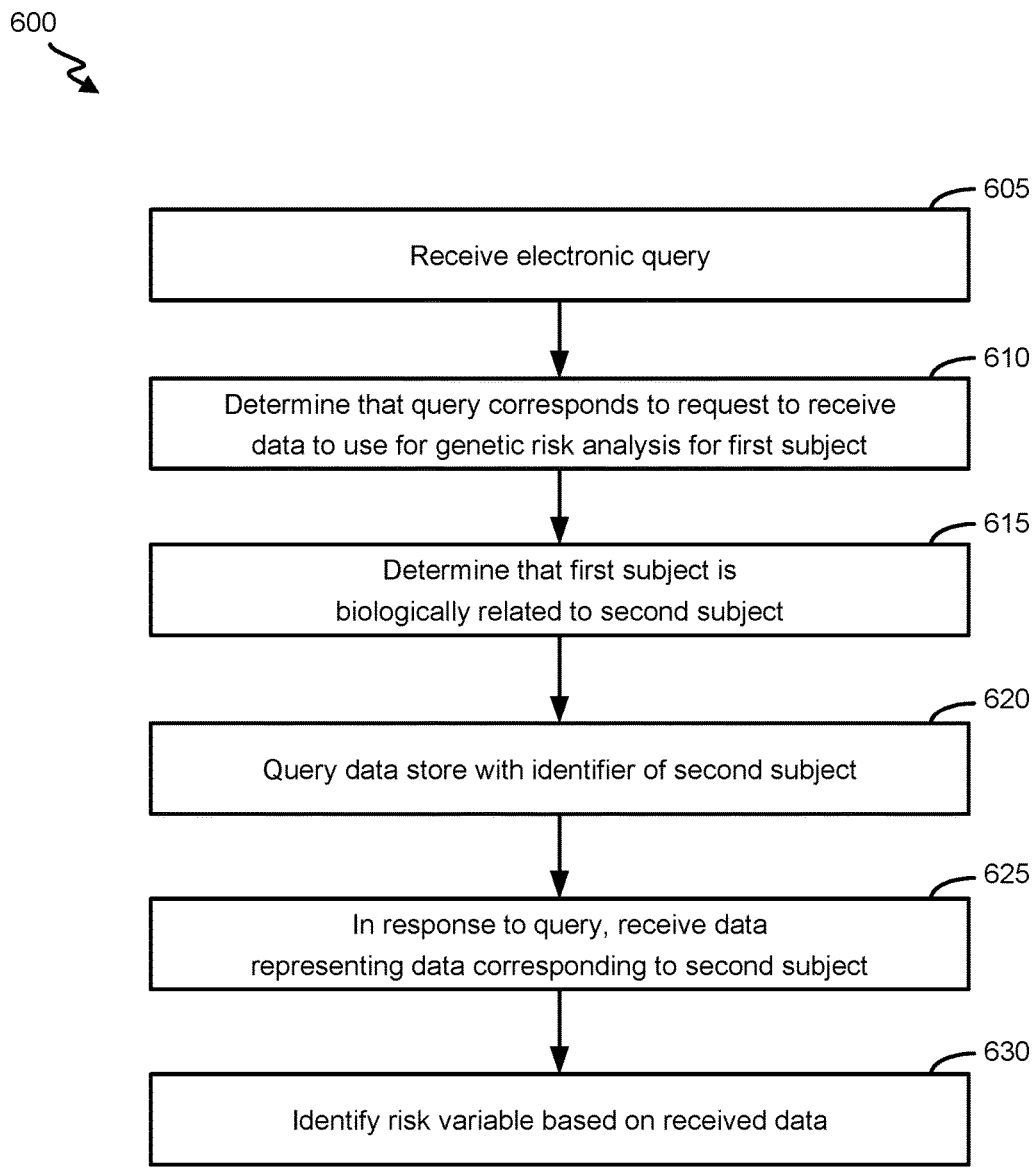
FIG. 6 shows an embodiment of a process for generating a risk variable for one subject based on genetic data of another subject.

Referring next to FIG. 6, an embodiment of a process 600 for generating a risk variable for one subject based on genetic data of another subject is shown. Process 600 may be performed in part or in its entirety by, for example, assessment system 105. Process 600 begins at block 605 where an electronic query is received from a requestor device. The electronic query may be received, for example, from a client device or physician device. The electronic query may be received via, for example, a webpage or app page. At block 610, it is determined that the electronic query corresponds to a request to receive data to use for a genetic risk analysis for a first subject. The first subject may include a client identified in or in association with the electronic query.

At block 615, it is determined that the first subject is biologically related to a second subject. The determination may be made, for example, via input having been provided by the first subject, input having been provided by the second subject, input having been provided by another entity, a communication received (e.g., in response to a request) from a remote or local genealogical data store, and/or based on an automated analysis of genetic data. In some instances, the second subject corresponds to another client of an assessment system.

At block 620, a data store is queried with an identifier of the second subject. The data store may include a local or remote data store. At block 625, in response to the query, data that is received that represents genetic data of the second subject or an input corresponding to a health characteristic of the second subject. The received data may include, for example, a sequence, variant detection and/or risk variable.

At block 630, a risk variable is identified based on the received data. The risk variable may identify a risk of developing a condition. In some instances, the risk variable is generated based on data from multiple second subjects determined to be biologically related to the second subject.

The risk variable may be transmitted to the first subject during an initial phase of a biological analysis or risk-assessment analysis. It may thus provide an initial risk estimate that may be provided prior to processing of any biological sample. It may be configured to be updated and/or modified upon subsequent access to genetic data for the first subject.

Figure 7:
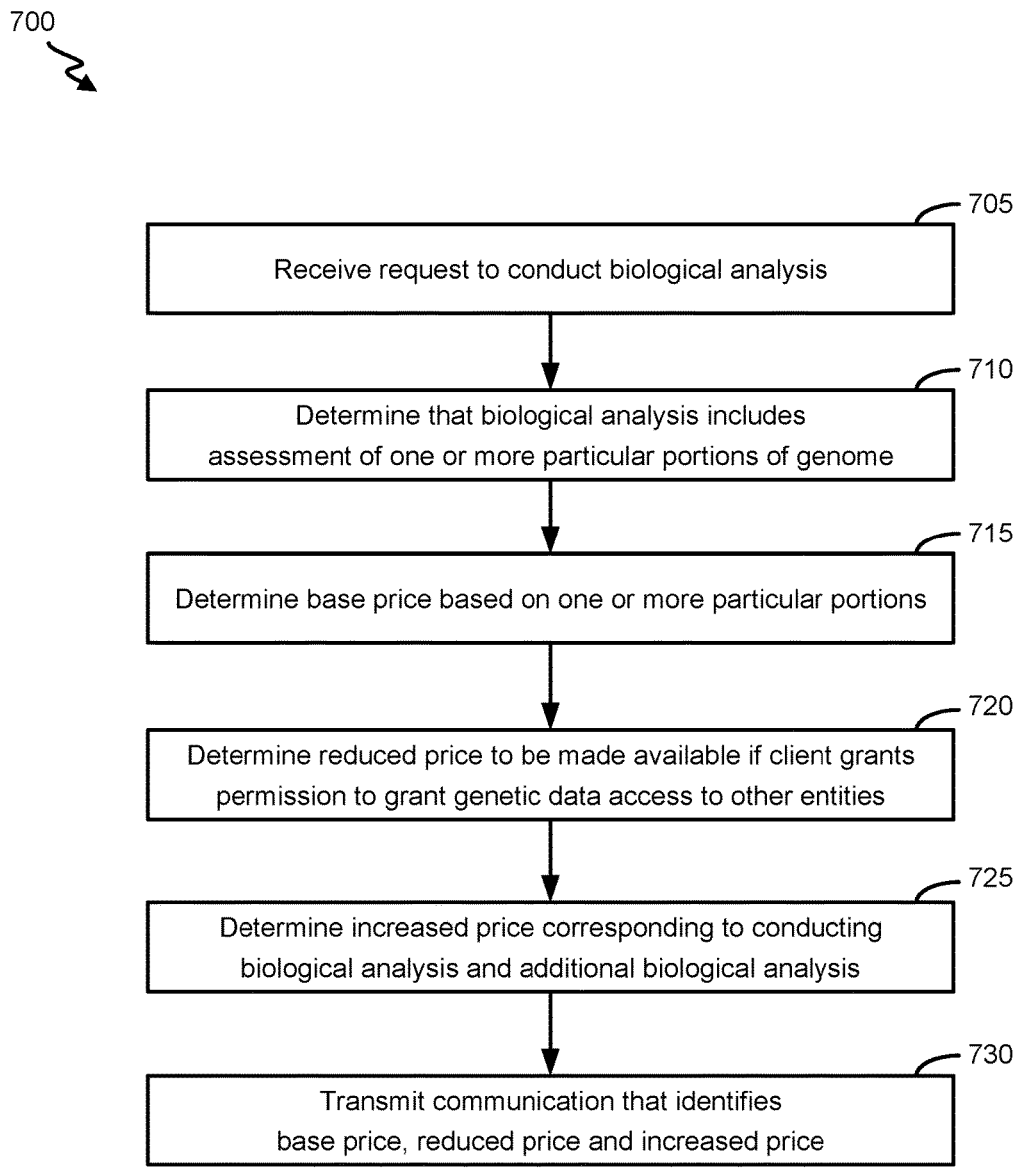
FIG. 7 shows an embodiment of a process for determining a set of potential prices for conducting biological analyses.

Referring next to FIG. 7, an embodiment of a process 700 for determining a set of potential prices for conducting biological analyses is shown. Process 700 may be performed in part or in its entirety by, for example, assessment system 105. Process 700 begins at block 705 where an electronic request is received from a first device. The request is one requesting that a biological analysis pertaining to a condition and a client be conducted. The electronic query may be received, for example, from a client device or physician device. The electronic query may be received via, for example, a webpage or app page.

At block 715, a base price is determined based on the one or more particular portions of the human genome. The base price may be a fixed price or a price determined based on one or more factors. The one or more factors may include, for example, which analysis was requested, a system positioned to potentially perform the analysis (e.g., assessment system of another system), how many portions are required for the analysis, whether (and, if so, what) new sequencing is required for the analysis, whether an analysis has previously been performed for the requestor, a characteristic of the requestor (e.g., location or age), and so on.

At block 720, a reduced price is determined that is to be made available if the client grants permission to provide data corresponding to the one or more particular portions of the human genome to one or more other entities. The provision of data may include identifiable access, such that the client can be identified, or de-identified access. The one or more other entities can include, for example, one or more developers. The data provided may include the same one or more portions and/or one or more other portions. The data may be provided to enable the one or more other entities to analyze the data. In various circumstances, the provision of data may correspond to a permission to contact the client based on a result of an analysis (e.g., to provide an up-sell opportunity).

At block 725, an increased price is determined that corresponds to conducting the biological analysis and to conducting one or more other biological analyses for the client. The one or more other biological analyses may include one or more specific analyses and/or a general indication that (for example) any or a specified number of additional analyses may be performed. The one or more other biological analyses may include performing an analysis related to the requested analysis.

At block 730, a communication is transmitted to the first device that identifies the base price, reduced price and increased price. The communication can be transmitted, e.g., in response to an HTML request so as to trigger presentation of a webpage. In some instances, the communication can trigger presentation of an app page. A communication can enable a selection of an option a selection associated with any of one or more of the prices. Account data for the client may be updated accordingly.

Figure 8:
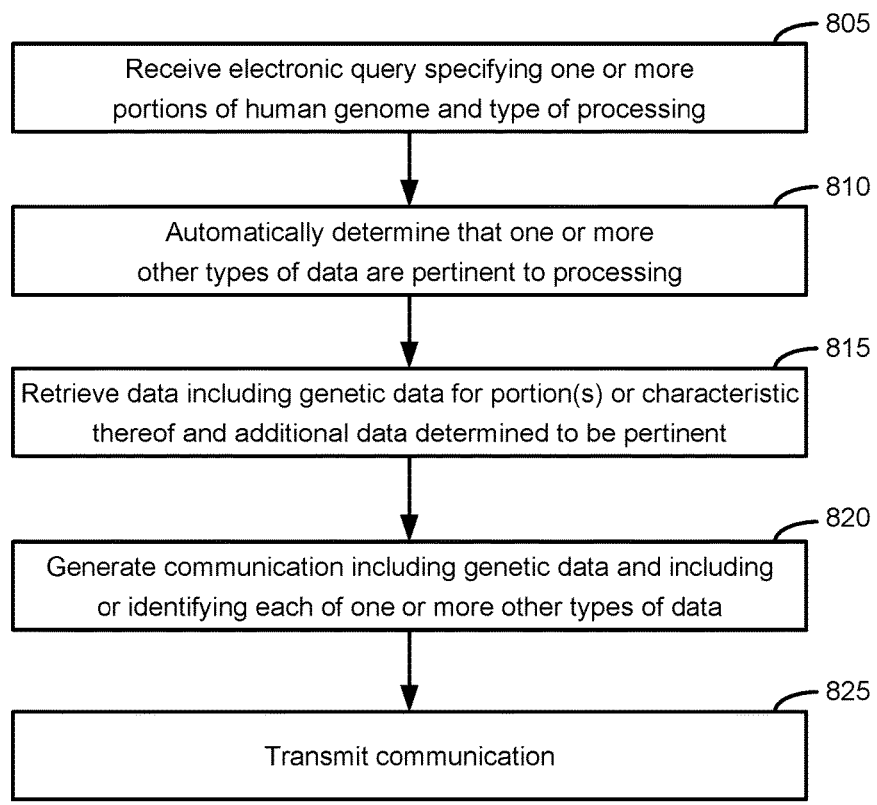
FIG. 8 shows an embodiment of a process for processing electronic queries for genetic data.

Referring next to FIG. 8, an embodiment of a process 800 for processing electronic queries for genetic data shown. Process 800 may be performed in part or in its entirety by, for example, assessment system 105. Process 800 begins at block 805 where an electronic query is received from a requestor device. The electronic query specifies one or more portions of the human genome and a type of processing to be performed. The query may be received, for example, from an external assessment device. The query may identify the one or more portions and/or a use or type of analysis.

At block 810, it is automatically determined that one or more other types of data are further pertinent to the type of processing to be performed. The one or more other types of data may include or correspond to, for example, one or more other portions of the human genome and/or to other types of data. The other types of data may include types of data not identified in the query and/or may include (for example) epigenetic data, input-derived data and/or health-record data. In one instance, the query identifies a first type of variant analysis requested in reference to one or more particular genes, and the one or more other types of data correspond to a second type of variant analysis in reference to the one or more particular genes and/or an analysis in reference to one or more other genes.

At block 815, data is retrieved that includes, in correspondence to a subject: genetic data corresponding to a sequence at the one or more portions or a characteristic thereof and additional data of the one or more other types of data. At least part of the retrieved data includes a non-genetic data point pertaining to a health or activity of the subject. The data may be retrieved from a local data store and/or a data store that is managed by and/or accessible to a data system performing process 800. In some instances, retrieving the data includes transmitting a request to a remote system that identifies the data and receiving a corresponding request.

At block 820, a communication is generated that includes the genetic data and includes or identifies each of the one or more other types of data. For example, the communication may include both the genetic data and the other data or the communication may include the genetic data that was requested in the genetic data and may indicate that other data relevant to the query (which may, but need not, be specifically identified) may be or is available. At block 825, the communication is transmitted to the requestor device.

Figure 9:
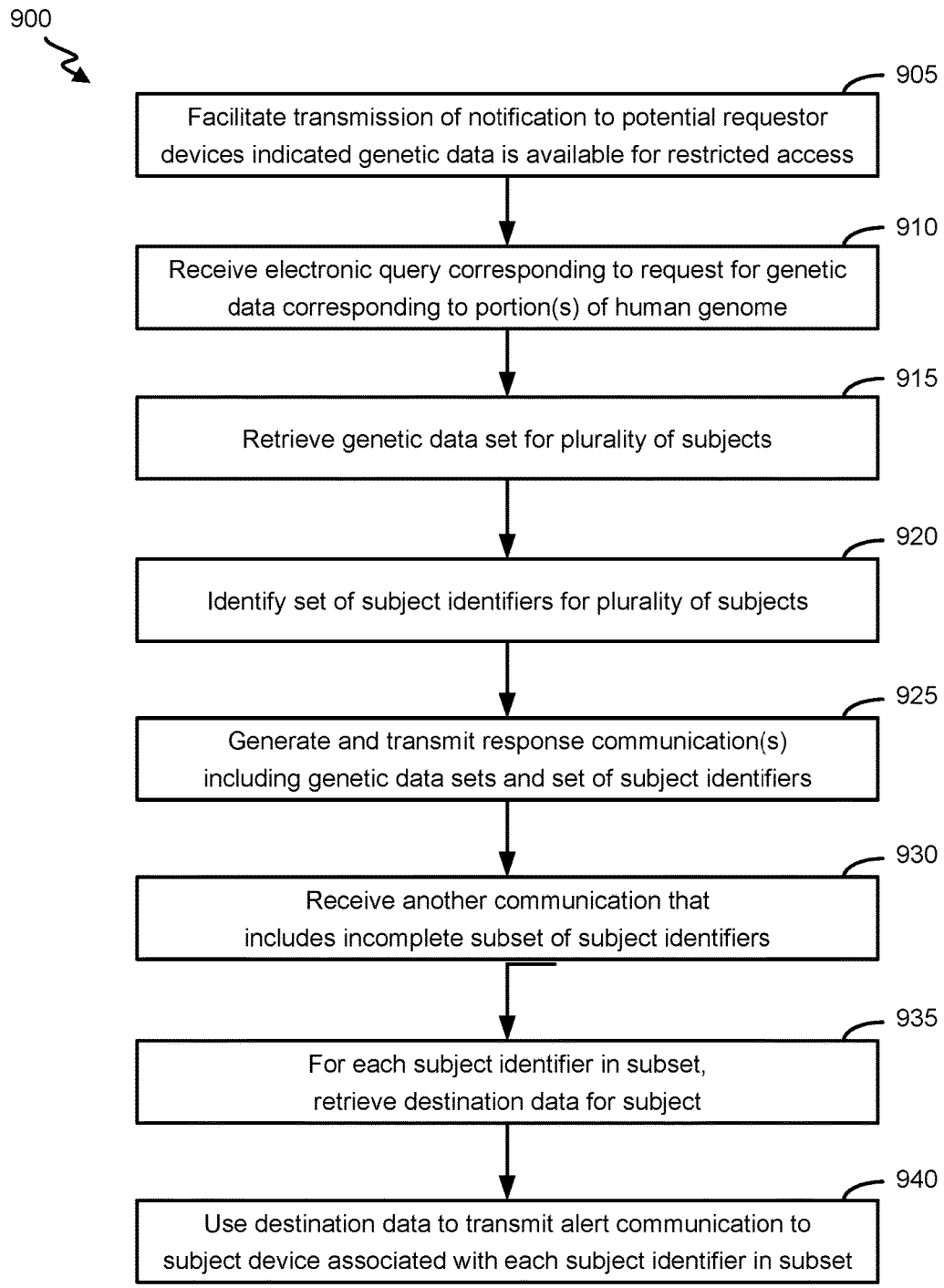
FIG. 9 shows an embodiment of a process for alerting subjects identified based on external data analyses of at least partly de-identified data.

Referring next to FIG. 9, an embodiment of a process 900 for alerting subjects identified based on external data analyses of at least partly de-identified data is shown. Process 900 may be performed in part or in its entirety by, for example, assessment system 105. Process 900 begins at block 905 where a transmission of a notification is facilitated to a plurality of potential requestor devices that indicates that subject genetic data of one or more specified types are available for restricted access. The indication that data is available for restricted access may indicate, for example, that data may be provided but that certain conditions may need to be satisfied before it is provided (e.g., establishing credibility of a requestor and/or determining that corresponding data-access permissions of one or more clients has been granted).

At block 910, an electronic query is received from a requestor device that corresponds to a request to receive genetic data corresponding to one or more portions of the human genome. At block 915, from a data store and for each subject of a plurality of subjects, a genetic data set associated with the subject is retrieved. The genetic data set corresponds to the one or more portions of the human genome. For example, the genetic data set may identify a sequence of each of one or more genes, any (and, in some instances, all) variants detected within a sequence of each of one or more genes, and/or a classification of any (and, in some instances, all) variants detected within a sequence of each of one or more genes. The genetic data set may be collected for (for example) each client, each client for which a corresponding data-access was granted, each client corresponding to an identified characteristic and/or each identified client.

At block 920, a set of subject identifiers is identified where each subject identifier in the set of subject identifiers identifying a subject of the plurality of subjects. Thus (for example), for each retrieved genetic data set, a subject identifier is identified. The subject identifier can include (for example) one generated based on a pseudo-random generation technique or counting technique. Identifying the subject identifier may include retrieving or generating a subject identifier. In the latter instance, the subject identifier may be stored (e.g., in association with the genetic data).

At block 925, one or more response communications are generated and transmitted to the requestor device that includes, for each subject of the plurality of subjects, the genetic data set and a subject identifier of the set of subject identifiers that corresponds to the subject. Thus, for example, the one or more response communications may identify an association between the subject identifier and the genetic data set. The one or more response communications may include, for example, one or more encrypted communications. The one or more communications may be transmitted, for example, via a webpage or app page or via an email or other type of message. The transmission of the response communication(s) may be conditioned upon a result of one or more assessments, such as an authentication of a requesting device.

At block 930, another communication is received from the requestor device that includes an incomplete subset of the set of subject identifiers. The incomplete subset of the set of subject identifiers includes a subset having been identified by performing a processing on the genetic data sets associated with the plurality of subjects. The other communication may be received from a same device or system to which the one or more response communications were transmitted. For example, a first quantity of genetic data sets may have been transmitted to an external system. The external system may have then identified that, for each of a second quantity of the first quantity, an assessment indicates that a client is at risk for another condition, that a given medication is likely (or is not likely) to be effective, and so on. Each of the second quantity of genetic data sets may be identified in the other communication.

At block 935, for each subject identifier in the incomplete subset, destination data corresponding to the subject is retrieved. The destination data may include, for example, an email address, IP address, login information, and/or phone number.

At block 940, for each subject identifier in the incomplete subset, the destination data is used to transmit an alert communication to a subject device associated with the subject identifier, the alert including information pertaining to the processing on the genetic data sets. The alert communication may identify a result of an assessment performed by an external system, may identify a type of analysis performed by an external system, and/or may include information pertaining to the external system (e.g., a webpage address, company name, fee for obtaining results, phone number, email address and/or so on). It will be appreciated that variations are contemplated. For example, an external system performing an analysis using provided data may contact clients directly.

Figure 10:
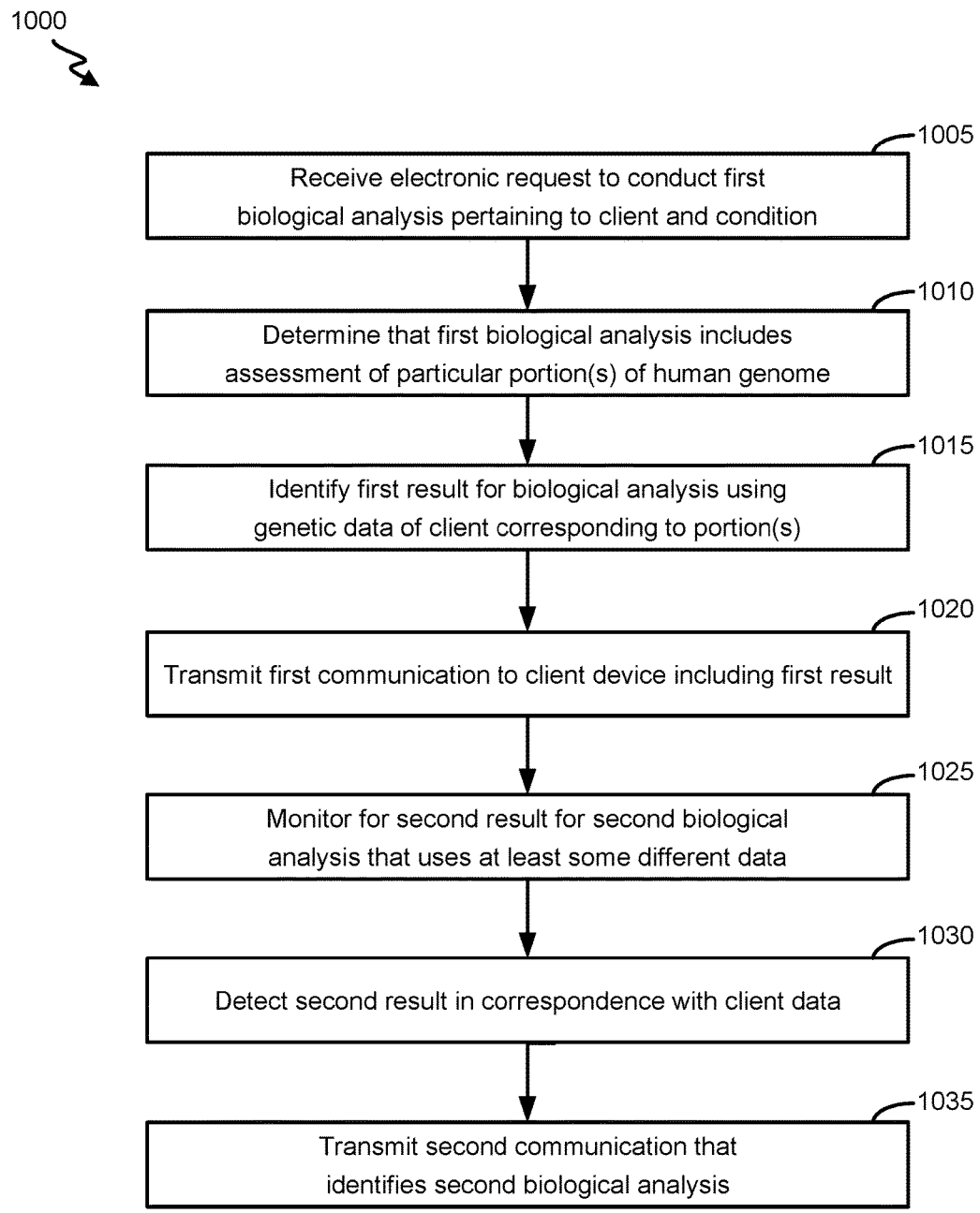
FIG. 10 shows an embodiment of a process for alerting a subject of a new analysis

Referring next to FIG. 10, an embodiment of a process 1000 for alerting a subject of a new analysis is shown. Process 1000 may be performed in part or in its entirety by, for example, assessment system 105. Process 1000 begins at block 1005 where an electronic request to conduct a first biological analysis pertaining to a condition and a client. At block 1010, it is determined that the first biological analysis includes an assessment of one or more particular portions of the human genome. Blocks 1005 and/or 1010 may correspond to similar actions disclosed herein.

At block 1015, a first result for the biological analysis for the client is identified. The first result is one that has been generated based on genetic data of the client corresponding to the one or more particular portions of the human genome. The first result may include, for example, a risk variable. For example, a risk variable may identify a predicted risk of developing a condition. At block 1020, a first communication is transmitted to a client device associated with the client. The first communication includes the first result.

At block 1025, monitoring is performed for a second result for a second biological analysis that is of a different type than the first biological analysis and uses at least some data not used in the first biological analysis. The monitoring may include local or remote monitoring. For example, the monitoring may include monitoring incoming communications from each of one or more external devices for results pertaining to the client. The monitoring may further or alternatively include monitoring to determine whether an analysis protocol, variant classification, alignment scheme and so on has changed so as to change or supplement the first result. As yet another example, the monitoring may involve determining whether new sequences of the client are available for analysis and/or whether one or more genetic data points of a related client are available for analysis. The second result may, but need not, but of a same type as the first result. For example, both the first result and the second result may correspond to a risk of developing a particular condition, or the first result and second result may correspond to risks of developing different conditions, or the first result may correspond to a risk of developing a condition and the second result to a predicted efficacy of a treatment. At block 1030, it is detected that a second result for a second biological analysis, that is of a different type than the first biological analysis and uses at least some data not used in the first biological analysis, has been identified.

At block 1035, a second communication is transmitted to the client device that includes an identification of the second biological analysis. The second communication may be transmitted, for example, via a webpage or app page, email, phone message, SMS message or other type of communication. In some instances, whether block 1035 is performed (or whether blocks 1025-1035 are performed) may depend on preferences and/or requests of a client. For example, a client may need to pay an additional fee for such monitoring and/or agree for such monitoring and alerts to be performed.

Figure 11:
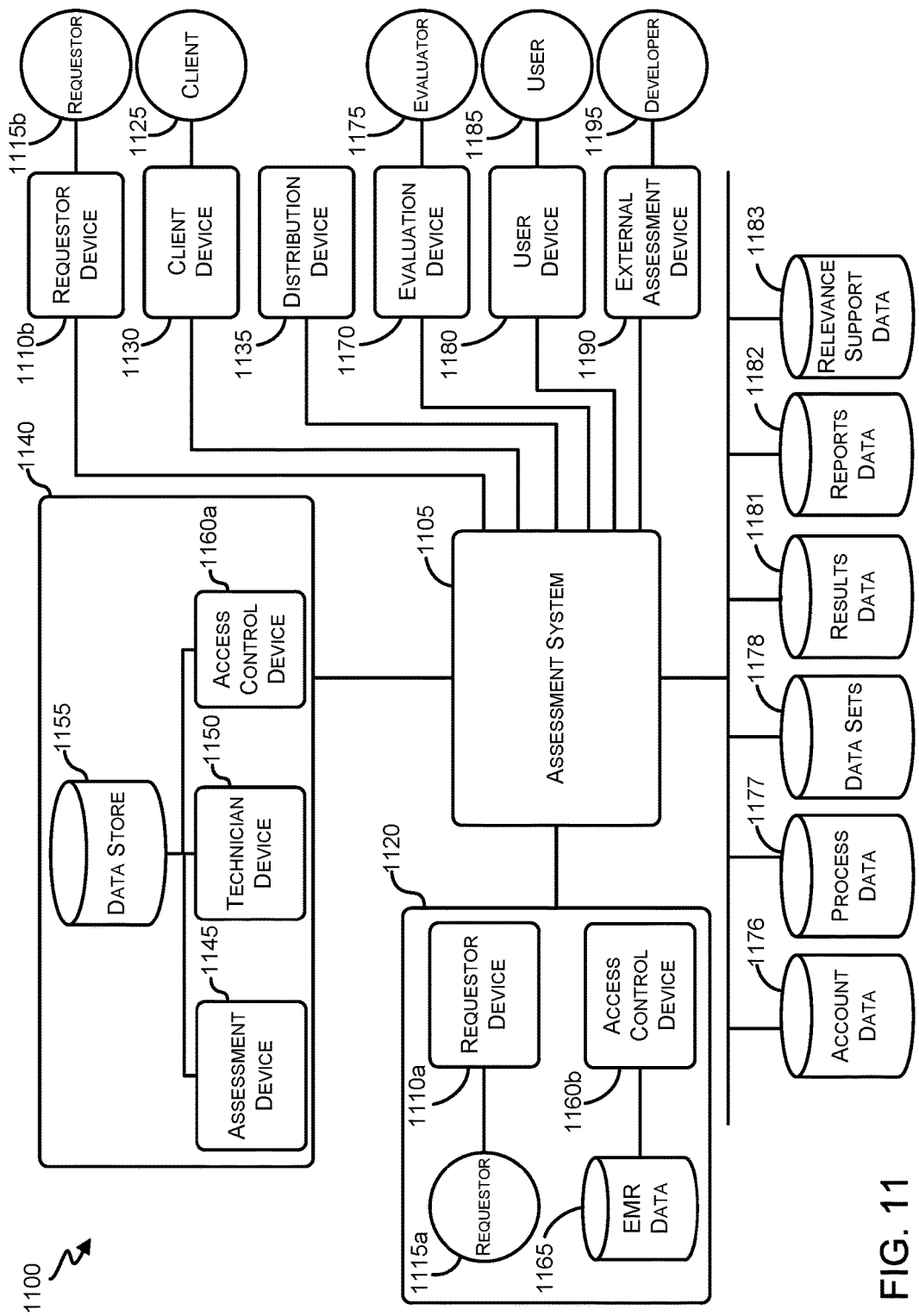
FIG. 11 shows a representation of a data processing network, in accordance with some embodiments of the invention.
Figure 12:
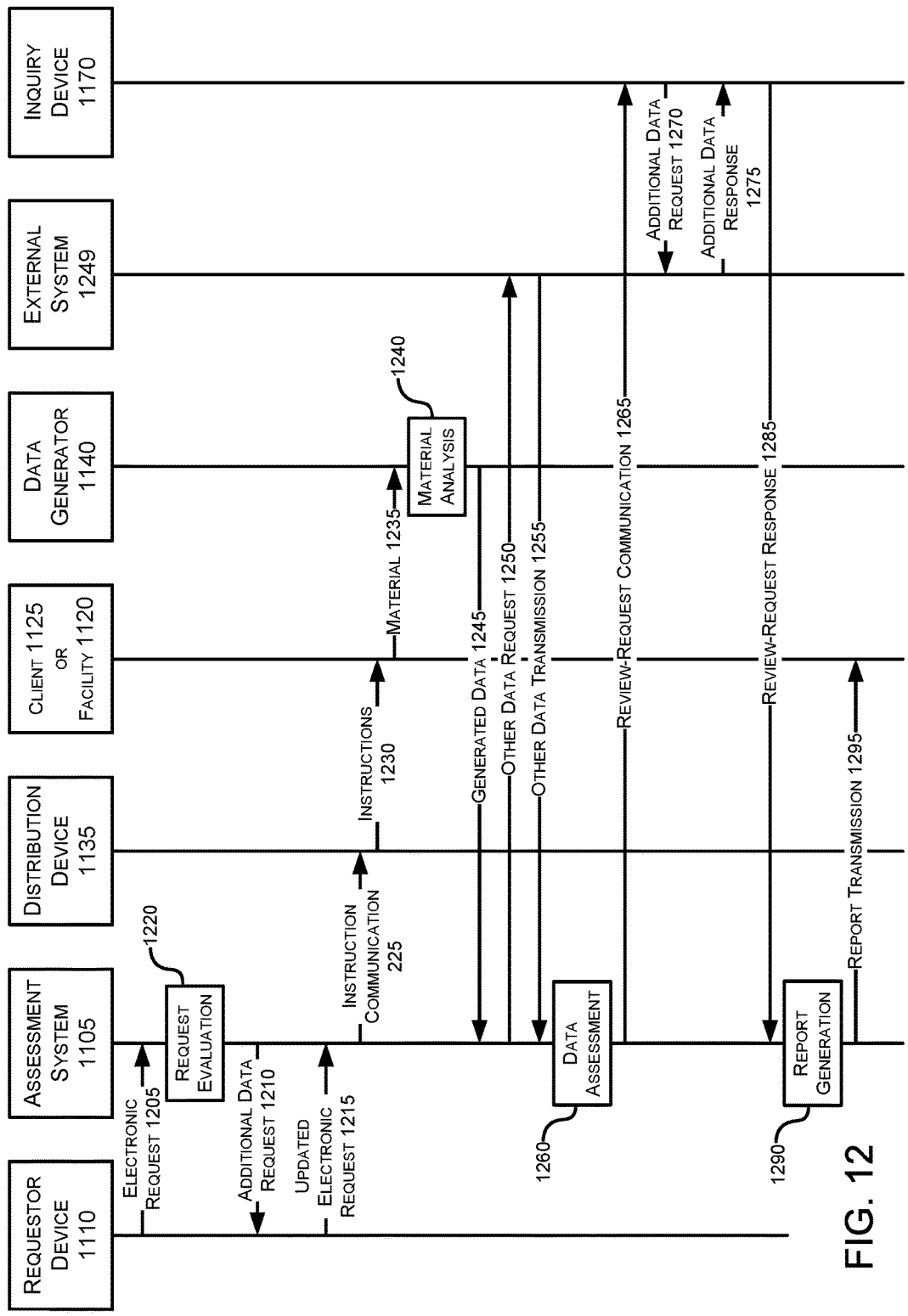
FIG. 12 shows a communication exchange between systems and devices of a data processing network, in accordance with some embodiments.

FIG. 11 shows a representation of an assessment network 100G. In addition, FIG. 12 illustrates interactions between various systems or components of assessment network 1100 to illustrate the flows of data and materials, for example. Assessment system 1105 may, for example, receive an electronic request 1205 from a requestor device 1110. Assessment system 1105 may include one or more electronic devices (e.g., storage devices, servers, and/or computers) and may, but need not, reside partly or entirely at a remote server. Requestor device 1110 may be configured and located to receive input from a requestor 1115. In one instance, requestor device 1110a is located in an external facility 1120. In one instance, requestor device 1110b includes an internally linked requestor device 1110b, such as one that itself receives invitations, such as from assessment system 1105, to generate electronic requests.

Request 1205 may include instructions to conduct a data-set analysis, for example. Optionally, request 1205 may be encrypted prior to transmission; such an electronic request may be decrypted upon receipt. Request 1205 may identify, or otherwise indicate, one or more states to be evaluated during the analysis and/or during an assessment. Request 1205 may identify a client and/or include additional data pertaining to the client, such as client-identifying data.

The client may be equated to, by assessment system 1105, a client device 1130. In some instances, a client device 1130, associated with client 1125, initially transmits a preliminary electronic request for the analysis and/or assessment to assessment system 1105. For example, such a preliminary electronic request may be initiated via interaction with a website associated with assessment system 1105. The same or a subsequent preliminary request may identify a particular requestor (e.g., by name, office location, phone number, and/or email address) and/or may request that a requestor 1115b associated with an internally linked requestor device 1110b submit such a request.

When a particular entity is identified in a preliminary electronic request, assessment system 1105 may identify a destination address (e.g., IP address or email address) associated with the entity and transmit a communication identifying information associated with the preliminary request (e.g., the client, a type of analysis, and so on). The communication may include a partial instruction and/or an input field that would confirm that the request of the client 1125 is to be generated and transmitted back to assessment system 1105. Such a communication may facilitate receipt of the electronic request 1205 from requestor device 1110b.

When it is requested that a requestor 1115b associated with an internally linked requestor device 1110b submit such a request, assessment system 1105 may transmit a similar communication to a requestor device 1110b that may have been selected from among multiple internally linked requestor devices. The selection may be based on a load balancing technique, availability hours, expertise, locations of the multiple requestor devices, a pseudo-random selection technique, and/or an entity affiliation.

Once request 1205 has been received from a requestor device 1110 (e.g., in response to a preliminary request from a client device 1130), assessment system 1105 may evaluate, such as at block 1220, the request 1205 to ensure that all required data has been provided and that all required data pertaining to client 1125 has been identified (e.g., via the request, a preliminary request and/or stored data). If assessment system 1105 determines that all required information has not been identified, a request 1210 for such information may be transmitted to requestor device 1110 and/or client device 1130. The request 1205 may be updated with this information and an updated electronic request 1215 may be transmitted to assessment system 1105. In various instances, an object provided to a user depends on an analysis requested, whether, and what kind of, new data-generation processing of a material is required for the analysis, a number of data-set units being assessed (e.g., and whether they have been previously assessed), a number and/or type of analyses being requested, a number and/or type of analyses previously requested, a number and/or type of analyses predicted to be requested subsequently, a state for which a progression prediction is being requested, whether a user is granting other entities' access to the client's data or results, whether a user is authorizing additional analyses to be performed on the client's data, and/or whether a user is granting permission to send offers to request user access to results or reports other than those initially being requested.

When all required information has been provided, assessment system 1105 may send an instruction communication 1225 to a distribution device 1135. Optionally, communication 1225 may be encrypted prior to transmission; such an encrypted communication may be decrypted upon receipt. Optionally, communication 1225 may be transmitted using communications system 1108 and/or over one or more network links, such as including transmission, at least in part, over a public communications network, such as the Internet. Communication 1225 may include, for example, a name and address of client 1125 and, in some instances, an indication as to what is to be provided to client 1125 for collection of a material for subsequent analysis. For example, a request 1205 may indicate a type of analysis that is to be performed on a material (e.g., an analysis pertaining to a likelihood of getting one or more particular types of states) and/or a type of material (e.g., type of sample) that is to be analyzed. Communication 1225 may identify the type of analysis, type of material, and/or kit associated with collection of the material. The communication 1225 may thus facilitate and/or trigger a physical distribution of instructions 1230, which may include a kit or other sample collection materials, to a client address. The instructions 1230 may include, for example, instructions as to how to collect a material, a container for storing the material and/or information pertaining to an instruction or type of analysis to be conducted. Alternatively, the instructions 1230 may be provided to a facility 1120, such as may be associated with a requestor 1115a, who may aid client 1125 in obtaining the material.

A material 1235 from client 1125 may then be directed to and received at a data generator 1140 for analysis 1240. Data generator 1140 may be, for example, part of a facility. Data generator 1140 may include one or more assessment devices 1145 configured to generate data reads, data elements, or data sets for various data-set units using the material 1235 as part of analysis 1240. For example, an assessment device 1145 may include a data-characterizer device (e.g., sequencer and/or polymerase chain reaction machine). Data generator 1140 may further include one or more devices 1150, such as a desktop or laptop computer. Generated data 1245 generated by or at one or more devices (e.g., assessment device 1145 or technician device 1150) may be stored at a data store 1155, which may be remote from all data generator devices or part of a data generator device. The data 1245 may, for example, include identifying client information (e.g., a name and address), facility information (e.g., location and name), device specifications (e.g., manufacturer and model of assessment device) and data. In some embodiments, a facility, such as facility 1120 or facility 1140, may correspond to a lab.

In some instances, data is optionally collected or requested from one or more external systems 1249. Thus, assessment system 1105 may transmit one or more other data requests 1250 and one or more other data transmissions 1255 may provide the other data. For example, one or more data sets and/or one or more processed versions thereof (e.g., identifying one or more sparse indicators) corresponding to an existing or new client may be received from an external system 1249, As another example, assessment system 1105 may transmit a client data set to an external system 1249, and external system 1249 may then return a result of an assessment of the client data set. As yet another example, other data may include a data set (or results based on such data) corresponding to another individual (e.g., an entity related to a client and/or an entity sharing a characteristic with a client). The other individual may be, for example, identified based on input from the client and/or automatically identified (e.g., based on a query of a data store to identify clients associated with inputs or results indicating a shared characteristic or relationship). In some instances, a state assessment variable may be generated based on data from multiple other people, and the data for each other person may be weighted based on (for example) how closely related the person is with a client and/or how many or which characteristics the person shares with a client.

An access control device 1160a may control which devices and/or entities may gain access to the data 1245, which may apply to devices and/or entities internal to data generator 1140 and/or to devices and/or entities external to data generator 1140. Access control device 1160a may implement one or more rules, such as restricting access to client data to one or more particular devices (e.g., associated with assessment system 1105). Such access may further or alternatively be controlled via logins, passwords, device identifier verification, etc.

In various instances, access control device 1160a controls access via control of pushed transmissions and/or via control of processing pull requests. For example, a rule may indicate that data 1245 pertaining to a material, such as a sample, is to automatically be transmitted to a particular assessment system 1105 (and/or device associated therewith) upon completion of a facility-based assessment or detection of particular data (e.g., data matching a request). Access control device 1160a may then monitor for such a criterion to be met and may then generate and transmit appropriate data.

Data 1245 may include a plurality of data reads, data elements, or sets (e.g., each data read in the plurality of data reads corresponding to a same client, or at least some of the plurality of data reads corresponding to different clients). In various instances, data 1245 may be transmitted to assessment system 1105 in a batch-mode, in a streaming mode, in real-time as data is produced, and/or upon request. Data 1245 may also be stored at a data store local or remote to data generator 1140. A given transmission or stream may include data that corresponds to a single, or in other instances to multiple, client, sample, and/or data reads. In some instances, access control device 1160a evaluates one or more transmission conditions, which may indicate, for example, whether and/or what data is to be transmitted given a quantity of data collected (e.g., generally, since a past transmission and/or for a given client or sample) and/or given a time since a previous transmission. In one instance, as data reads are generated by an assessment device, a data set is generated so as to include each new data read and one or more identifiers (e.g., of a client, sample, time and/or facility device). The data may then be transmitted via a discrete communication (e.g., via FTP, over a webpage upload, email message, or SMS message) to assessment system 1105. In one instance, the data may then be appended to a stream that is being fed to assessment system 1105.

It will be appreciated that assessment network 1100 may, in some instances, include multiple data generators 1140, each of which may include an assessment device 1145, technician device and/or access control device 1160a. Further, a given data generator 1140 may, in some instances, include multiple assessment devices 1145, multiple technician devices 1150 and/or multiple access control devices 1160a. Thus, data 1245 received at assessment system 1105 may include data collected by and/or derived from data collected by different assessment devices, which may result in the data having different biases, units, and/or representation. Similarly, personnel operating different technician devices 1150 may utilize different protocols and/or data interpretation techniques, which may again result in receipt of data at assessment system 105 that has different biases, units, variables, and so on. Further, even data originating from a same device may, in time, exhibit different biases, units, and so on, which may be a result of a manipulation of a control of the device and/or equipment wear.

Thus, in some instances, assessment system 1105 performs a comparison across data 1245 received from a data generator device (e.g., an access control device 1160a or directly from an assessment device 1145 or technician device 1150) associated with data generator 1140. The comparison may be across, for example, data collected at different facilities, data based on measurements collected at different devices, and/or data collected at different times. It will be appreciated that the comparison may include a direct comparison of collected data or comparing preprocessed versions of the collected data. For example, received data may first be preprocessed via a transformation and/or dimensionality-reduction technique, such as principal component analysis, independent component analysis, or canonical correspondence analysis.

The comparison may include, for example, performing a clustering technique so as to detect whether data corresponding to a given facility, device, or time period predominately resides in a different cluster than data corresponding to one or more other facilities, devices, or time periods. The clustering technique may include, for example, a connectivity based clustering technique, a centroid-based clustering technique (e.g., such as one using k-means clustering), a distribution-based clustering technique, or a density-based clustering technique.

The comparison may additionally or alternatively include a statistical technique, such as one that employs a statistical test to determine whether two or more data sets (e.g., corresponding to different facilities, devices, or time periods) are statistically different. For example, a Chi-square, t-test or ANOVA may be used.

The comparison may additionally or alternatively include a time-series analysis. For example, a regression technique may be used to determine whether output from a given device is gradually changing in time.

When it is determined that particular data corresponding to a given facility, device, or time period is different than data corresponding to one or more other facilities, devices, or time periods (e.g., is assigned to a different cluster than other data or is associated with a p-value below a threshold), a normalization and/or conversion factor may further be identified. For example, a normalization and/or conversion factor may be identified based on centroids of data clusters and/or inter-cluster distances. As another example, a linear or non-linear function may be derived to relate data from a given facility, device, or time period to other data.

In some instances, a determination that particular data corresponding to a given facility, device, or time period is different than data corresponding to one or more other facilities, devices, or time periods may indicate that data from the given facility, device, or time period is not to be used. In such instances, an instruction communication may be sent to a facility to reprocess a material, such as a sample.

In addition to receiving data 1245, assessment system 1105 may further collect one or more other data that may be used to assess, for example, a likelihood for transitioning into a particular state. For example, one type of other data may include inputs provided at a client device 1130, such as inputs that indicate past-state data and/or current-state data, familial-state data and statuses, age, occupation, activity patterns, association with environments having particular characteristics, and so on. The other data may be received by way of one or more other data transmissions 1255 from external system 1249. Optionally, other data transmission 1255 may be encrypted prior to transmission; such an encrypted transmission may be decrypted upon receipt. Optionally, other data transmission 1255 may be transmitted over one or more network links, such as including transmission, at least in part, over a public communications network, such as the Internet. Optionally, other data transmission 1255 may be transmitted over at least a portion of communications system 1108.

Another type of other data may include data automatically detected at a client device 1130. For example, a wearable client device may track activity patterns so as to estimate calories burned per day, or the wearable client device may estimate a pulse distribution, client temperature, sleep patterns and/or indoor/outdoor time. This data obtained directly by client device 1130 may be directly transmitted (e.g., after request 1250 and/or authorization handshake) to assessment system 1105 and/or via another client device (e.g., via accessing health-data on a phone or computer device). Optionally, other data obtained directly by client device 1130 may be transmitted over one or more network links, such as including transmission, at least in part, over a public communications network, such as the Internet. Optionally, other data obtained directly by client device 1130 may be transmitted over at least a portion of a communication system. Optionally, other data obtained directly by client device 1130 may be part of other data transmission 1255.

Yet another type of other data may include record data, which may be stored, for example, at a record data store 1165 at and/or associated with an external facility, such as one having provided an electronic request to perform an analysis or assessment pertaining to a client and/or one as identified via input at a client device 1130. To illustrate, the other data may identify one or more client reported experiences and/or evaluation results for a client or may include a result of one or more tests.

In some instances, other data may include data pertaining to a different client. For example, it may be determined or estimated that a given client is related to another client. Such determination or estimation may be based on inputs detected at a client device identifying one or more family members (e.g., by name), and a data store may be queried to determine whether any clients match any of the family member identifications. Such relationship determination or estimation may alternatively or additionally be based on a data set analysis, such that a raw or processed data set from the given client is compared to a raw or processed data set from some or all other clients to identify, for example, whether any other clients share a threshold portion of a data set with the client. Upon detecting an above-threshold match, a percentage of value matching may be used to estimate a type of relationship between the clients. Upon identifying a related client, other data corresponding to the related client may be identified. For example, the other data may include a past or current state of the related client. The other data may be identified (for example) based on an input provided by the client or the related client or record data associated with the related client.

Thus, assessment system 1105 may have access to, for a given client, one or more data sets, data set availability modification data, client-reported data, record data, test data, activity data, and/or other types of data. These data may be detected, assessed, or otherwise evaluated, at block 1260, such as in one or more assessment processes. Data sets may be evaluated to detect and assess sparse indicators, for example, as described below in further detail. The detection and/or assessment at block 1260 may be performed, for example, partly or fully at assessment system 1105. In some instances, the detection and/or assessment at block 1260 is performed in a partly or fully automated manner. In some instances, the detection and/or assessment at block 1260 involves processing of inputs provided by a reviewer or evaluator.

Generation of a report, at block 1290, may be performed using the results of data assessment of block 1260. A report transmission 1295 may include the report and be transmitted to client 1125 or facility 1120, such as by way of client device 1130 or requestor device 1110a.

Figure 13:
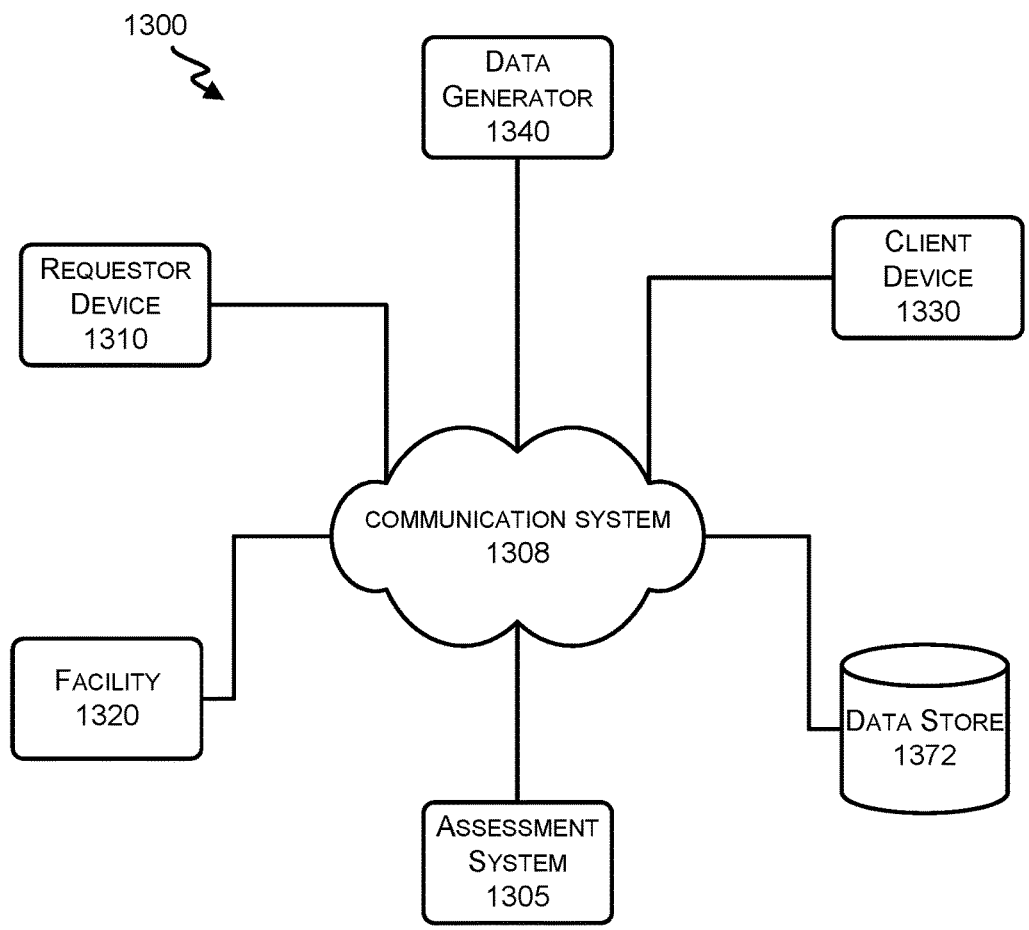
FIG. 13 shows a representation of an example communication network, in accordance with some embodiments.

Referring next to FIG. 13, an assessment network 1300 is shown in one embodiment. Assessment network 1300 may, but need not, correspond to assessment network 1100 shown in FIG. 11. Through the interaction of multiple devices and entities, an assessment system 1305 may receive data sets corresponding to individual clients. As illustrated, assessment system 1305 may connect, via communication system 1308, to each of one or more other systems or devices. Assessment network 1300 may also include additional systems or devices, as illustrated in FIG. 13. For example, assessment network 1300 may include requestor device 1310, facility 1320, client device 1330, data generator 1340, and data store 1372, in addition to other systems or devices not explicitly depicted in FIG. 13.

Data may be exchanged between various systems or devices of assessment network, such as by way of communication system 1308. Communication system 1308 may, for example, include one or more data communication systems or networks, such as a wired or wireless data connection that makes use of or is compliant with one or more Institute of Electrical and Electronics Engineers (IEEE) networking standards, such as 802.3 (Ethernet), 802.11 (Wi-Fi), or 802.16 (WiMAX), or other data communications standards such as IEEE 1394 (FireWire), Bluetooth, Universal Serial Bus (USB), Serial ATA (SATA), Parallel ATA (PATA), Thunderbolt, Fibre Channel, Small Computer System Interface (SCSI), GSM, LTE, etc. Communication system 1308 may include one or more TCP/IP compliant interconnections, such as may be present on a private or public communications network, such as the Internet. Communication system 1308 may further include servers, systems, and storage devices in the cloud. Communication system 1308 may represent or include one or more intermediate systems or data connections between various other components of assessment network 1300. Additionally, communication system 1308 may represent a direct connection between various other components of assessment network 1300, such as a direct connection between assessment system 1305 and data store 1372, which may optionally allow for communication with data store 1372 by other components of assessment network 1300 only by way of assessment system 1305, for example. It will be appreciated that data store 1372 may include one or more data stores, which may optionally be linked or otherwise configured or organized to allow for efficient retrieval and storage of data by reference to different entries in particular data stores or data tables. For example, data store 1372 may comprise a relational database or data store, in some embodiments.

One or more of the devices or systems of assessment network 1300 may be present at a single location or each may be present at various different locations and be in data communication with one another via communication system 1308, depending on the specific configuration. For example, facility 1320 and data generator 1340 may be at a same location. Requestor device 1310 may further be present at facility 1320, such as if possessed by a requestor personnel, for example. Similarly, client device 1330 may also be present at data generator 1340 or facility 1320, such as if possessed by a client, for example. In some embodiments, one or more devices or systems of assessment network 1300 may be mobile devices, such as a smartphone, tablet computer, laptop, or other compact device, which may facilitate transport between locations or with a user or client. Use of mobile devices may, for example, be advantageous for allowing input to be entered in real-time and/or on request from any location in order to facilitate expedient processing and/or analysis of data or generation of state assessments.

In one instance, assessment system 1305 receives a request communication (e.g., via communication system) from a requestor device 1310 that identifies a client. Client identifying authentication and/or other information can be received from a client device (e.g., which, in some instances, is also requestor device 1310). Assessment system 1305 may then prime data generator 1340 to detect a material associated with the client and generate a set of reads based thereupon.

Assessment system 1305 may process the reads by, for example, aligning individual reads to a reference data set (e.g., reference genome) and generating one or more client data sets. For example, a first client data set may include an identifier data set (e.g., a sequence) that identifies a base at each of a set of positions, such at each position along one or more data-set units (e.g., genes). The identifier data set may be generated by, for example, identifying a set of identifiers as those present in the reads aligned to a given position, at the position, and detecting a most common identifier from amongst the set of identifiers. A second client data set may include a coverage data set that identifies, for each position of a set of positions (e.g., at each position along one or more data-set units) a number of reads aligned to overlap with the position. Assessment system 1305 may detect one or more differences (e.g., variants) using the data set(s). For example, a difference may be identified by detecting a difference, at a given position, between a value of the identifier data set and a corresponding value of the reference data set. As another example, a difference may be identified by detecting an abrupt change in a coverage data set (e.g., such that values abruptly change approximately 2- or 3-fold). A sparse indicator may be defined for each difference so as to identify a type of difference observed (e.g., what identifier was present in an identifier data set as opposed to a reference data set or how a coverage data set changed) and a position (e.g., with respect to the reference data set and/or along one or more data-set units) at which the difference was observed.

Each sparse indicator may be assigned to a bucket which may reflect a predicted impact of the detected difference. In some instances, a set of buckets are defined. Each of one, more or all of the buckets may correspond to a predicted likelihood that a client will progress to a given state. A state may include, for example, utilizing a full memory bank, a condition (e.g., cancer), reduced bandwidth, and/or a connection drop. Thus, buckets may reflect whether and/or a degree to which a difference causes the state (e.g., reflecting memory requirements, whether the difference is (e.g., and/or is likely to be) pathogenic or benign), consumes bandwidth, and/or impairs a connection's stability). For each client, a determination as to how many sparse indicators were assigned to one or more particular buckets may be used to generate a result that identifies a state-progression prediction. The result may be transmitted to requestor device 1310 and/or client device 1330.

Reads, data sets, sparse indicators, bucket assignments and/or results may be stored (e.g., in association with corresponding client identifiers) in one or more data stores. In some instances, data may be subsequently retrieved for performing an updated assessment (e.g., using a new bucketing protocol or result-generation technique), performing a different type of assessment and/or transmitting data to another device.

Figure 14:
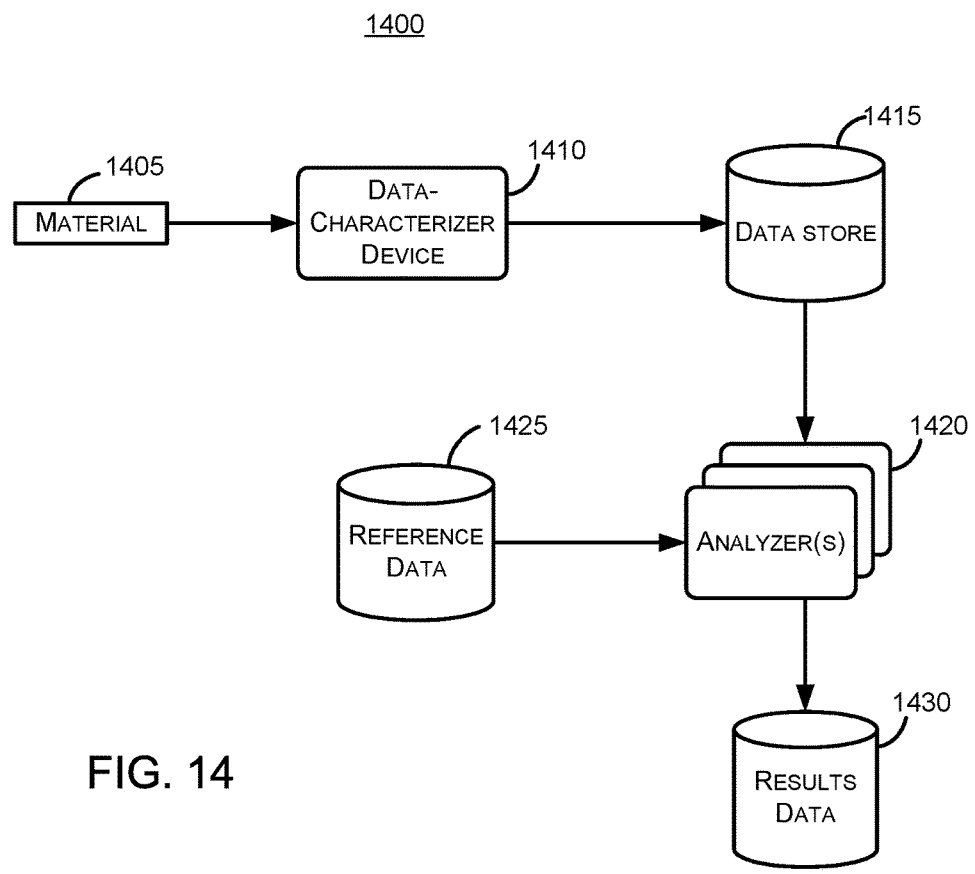
FIG. 14 shows a data flow, in accordance with some embodiments.

Turning next to FIG. 14, a data flow embodiment 1400 is shown. Initially, a test material 1405 is obtained from a client. As described above, the material 1405 may be obtained directly by the client using a collection kit. A client may be able to obtain the material themselves, particularly if the material is easy to collect. Alternatively or additionally, material 1405 is obtained at a facility. Obtaining material 1405 at a facility may be useful if the material is more difficult to obtain, or if chain-of-custody is a concern.

Material 1405 is assessed by a data-characterizer device 1410, which may generate a plurality of data sets, including coverage data sets and identifier data sets. As the data sets are determined, they may be stored in data store 1415 for subsequent analysis.

Data-characterizer device 1410 and data store 1415 may be located at a same location, such as a facility. Alternatively, data-characterizer device 1410 and data store 1415 may be remote from one another. In such a configuration, transmission of data sets from data-characterizer device 1410 to data store 1415 may occur using any of a variety of data communication standards and/or protocols. In one example, data sets are transmitted from data-characterizer device 1410 over a wired and/or wireless network to reach data store 1415. In another example, data sets are stored by data-characterizer device 1410 directly to a storage medium, such as a flash drive or hard drive, which may be used to facilitate relaying data sets to remote data store 1415. Optionally, data store 1415 may comprise the storage medium. Data sets stored in data store 1415 may be analyzed by data set analyzer 1420. Data set analyzer 1420 may be located at a same or different location from data-characterizer device 1410 and/or data store 1415.

Depending on the particular configuration, data sets generated by data-characterizer device 1410 and/or stored in data store 1415 may be analyzed individually, in real-time as the data sets are produced, or in batches, such as upon completion of a plurality of data sets. Data set analyzer 1420 may utilize reference data stored in reference data store 1425 in analysis of the data sets generated by data-characterizer device 1410 and/or stored in data store 1415.

A variety of analyses may be performed on the data sets by data set analyzers 1420. For example, data set analyzer 1420 may align each read in a data set to a portion of one or more reference sets. Data set analyzer 1420 may also generate coverage data and/or identifier data using reads from the data set. Upon completion of the analysis, the information corresponding to the data sets (e.g., coverage data and/or identifier data) and/or alignment indications may be transmitted to and/or stored in one or more results data stores 1430, which may correspond to a portion of data store 1372.

It will be appreciated that data set analysis may be resource intensive, and thus a plurality of data set analyzers 1420 may be used during the analysis process to distribute the resource burden, for example, and/or increase the rate at which data sets may be analyzed. For example, if a plurality of alignments are to be evaluated, such as by determining a potential alignment of an individual data set against multiple reference data sets, it may be desirable to distribute the tasks among multiple data set analyzers 1420. Load balancing between a plurality of data set analyzers 1420 may be performed to further enhance the use of resources, for example. Additionally, it may be desirable to compare the data sets stored in data store 1415 against multiple reference data sets, such as from related family members or from people sharing one or more characteristics, as described above, and comparisons of the data sets with different reference data sets may be performed by different data set analyzers.

Additionally or alternatively, data sets may be analyzed by one or more data set analyzers 1420 to identify one or more sparse indicators. Additionally or alternatively, data sets may be analyzed by one or more data set analyzers 1420 to categorize each data set, alignment, or detected sparse indicator. Additionally or alternatively, data sets may be analyzed by one or more data set analyzers 1420 to score each data set, alignment, or detected sparse indicator. Again, sparse indicators, categories, and scores may be transmitted to and/or stored in results data store 1430, which may be included in data store 1372.

Detecting sparse indicators may include aligning each data set with a reference data set. The reference data set may include part of a full reference data set and/or may include a data set identified based on identifying median or mode data elements across a plurality of data set derived from samples from a population. In some instances, an alignment is determined to be accurate throughout the data set, and differences between the data set and reference data set can be represented as sparse indicators, each corresponding to one or more positions (e.g., relative to an axis of the reference data set or to an axis of the data set). In some instances, a sparse indicator may further be defined using a value or identifier data of the data set (e.g., that differs from a corresponding value in the reference data set). In some instances, a sparse indicator may be defined based on identifying a type of structural difference detected in the data set relative to the reference data set (e.g., duplication, insertion, inversion or deletion). In some instances, an alignment is determined to be accurate throughout part of the data set but not for another part. It may then be determined that such partial alignment is attributable to the data set, for example, lacking representation of a part of the reference sequence or having an additional set of values. A sparse indicator may therefore identify information corresponding to multiple positions (e.g., reflecting a start and stop of a part of a reference data set not represented in a data set or the converse) and/or multiple values (e.g., reflecting which values were in one of either the reference data set or the data set but not in the other).

In some instances, a state transition likelihood associated with a particular deviation (e.g., sparse indicator) and/or with a combination of deviations is unknown or is associated with a below-threshold confidence. With reference again to FIG. 11 and FIG. 12, upon detecting such a deviation or combination (or a threshold quantity thereof), the particular deviation and/or combination may be identified in a review-request communication 1265 and transmitted to an evaluation device 1170. Evaluation device 1170 may then present the identification to an evaluator 1175 and detect input that is indicative of an estimated likelihood to associate with the deviation and/or combination, for example, as part of an optional review analysis process. A review-request response 1285 may be transmitted from evaluation device 1170 to assessment system 1105, for example, to provide the results of any review or input generated by an evaluator 1175. The data included in review-request response 1285 may be used in report generation process of block 1290 and may be included and/or otherwise influence the content of the final report transmitted in report transmission 1295.

A result generated by assessment system 1105 may include a quantitative or qualitative (e.g., categorical) likelihood variable, such as one corresponding to a transitioning to a particular state. For example, the likelihood variable may include a percentage probability or range of transitioning into a particular state. As another example, the likelihood variable may be partitioned into three categories.

Assessment system 1105 may generate an electronic report, at block 1290, that includes the result and/or that is selected based on the result. A report communication or transmission 1295 may include the report and be transmitted to client 1125 or facility 1120, such as by way of client device 1130 or requestor device 1110a. As an example, a report may identify one or more sparse indicators detected in a client data set and/or a bucket of each of one or more sparse indicator. A report may identify a likelihood (e.g., numeric or categorical) of transitioning to a particular state and/or a technique for having generated such a result. A report may identify types of data (e.g., particular data-set units and/or other type of data) used in the analysis. A report may identify a confidence in a result (e.g., a likelihood variable). A report may identify a recommendation (e.g., to contact a requestor or to receive a particular test or evaluation).

In some instances, a report must be approved (e.g., by a requestor 1115a or 1115b) before it is transmitted to a client device 1130. A report-reviewing interface may, but need not, include a configuration to allow a reviewing entity to change or add to the report. A report-reviewing interface may further allow or require a reviewing entity to identify a time at which to send the report to a client.

Assessment system 1105 may update and may have access to a variety of data stores, part or all of which may be remote from, co-localized with assessment system 1105, and/or included in assessment system 1105. One or more of the data stores may include a relational data store, such that data from one data store or structure within a data store may be used to retrieve corresponding data from another data store or structure.

Each of one, more, or all of the data stores may be associated with one or more access constraints. Access constraints applicable to a given data store may be stored as part of the data store or separately (e.g., in an access control data store). Access constraints that apply to one type of data may differ from access constraints that apply to another type of data. For example, account and client data may be associated with stricter access constraints than results data, to make it more difficult for a user, developer, or hacker to be able to link data to a particular individual. An access constraint may identify one or more individuals, devices, systems, and/or occupations permitted to access some or all data in a data store. An access constraint may include a rule, such as one that indicates that a user is permitted to access data pertaining to any of a group of users that the entity was involved in with respect to a transfer of a kit, or that indicates that any low-level authorized user is permitted to access de-identified data but not identifiable data, or that indicates that a high-level authorized user is permitted to access all data. As another example, access constraints may indicate that process data is to be hidden from external developers and available to internal users; that data-set unit, sparse indicator, and data set availability data is to be made available to all authorized external developers and internal users; and that client data is to be availed to authorized internal users and only availed to external developers to the extent to which each corresponding users represented in the data is a user of the developer (e.g., and that the client authorized such data access).

When different access rights apply to different types of data, a query protocol may be established to address instances where a query relates to each type of data. For example, a query may request Variable X for each client corresponding to Data Y, and Variable X and Data Y may correspond to different access constraints. As another example, a query may request a count of clients for which both Data Y and Data Z was detected, and Data Y and Z may correspond to different access constraints. One example of a query protocol is to use a most restrictive overlap of data constraints applying to the query. Another example of a query protocol is to permit use of an at least partly more relaxed access constraint so long as it relates to defining a client set or state and not to results to be returned or processed.

In some instances, an access constraint is configured to inhibit an identification of particular data (e.g., client identity). Such a constraint may relate to a precision of requested data. To illustrate, a constraint may be configured to permit a user to request and receive data identifying client locations, so long as the request is configured to not request too specific of a location and/or so long as the request corresponds to a number of client data elements sufficiently large to obscure (e.g., in a statistical result) a precise location. Compound queries may be more sensitive to potential identification concerns, such that one or more access constraints are configured to permit access to less precise data when multiple data elements are being requested.

Various data stores may be included in assessment networks 1100 and 1300. The data stores may include, for example, an account data store 1176, which may include login credentials for one or more users or clients and/or types of data access to be granted to each user or client; process data store 1177, which may identify facility analysis characteristics pertaining to particular data elements (e.g., identifying a facility, piece of equipment, and/or processing time); data sets data store 1178, which may identify one or more data sets associated with a given client or material, such as a sample; and one or more data-set expressions or signatures associated with a given client or material, such as a sample. The data stores may further or alternatively include a results data store 1181, which may identify one or more sparse indicators identified by and/or one or more results generated by assessment system 1105 that are associated with a given client or material, such as a sample.

The data stores may further or alternatively include a reports data store 1182, which may include one or more report templates (e.g., each associated with one or more result types) and/or one or more reports to be transmitted or having been transmitted to a client device; and/or a relevance support data store 1183, which may identify which types of data (e.g., data-set units, full or partial reference data sets, activity patterns, inputs, records, tests, etc.) are established to be, potentially, established not to be, or unknown whether to be relevant for evaluating a particular type of likelihood (e.g., a likelihood of transitioning into a particular state).

Relevance support data store 1183 may include identifications of one or more content objects. The identifications may include, for example, web addresses, journal citations, or article identifiers. In some instances, an identification identifies one or more sources associated with the content object (e.g., scientist, author, journal, or data store). Content objects may be tagged with one or more tags, which may identify, for example, a sparse indicator, a data-set unit, a data set, and/or a type of assessment. In some instances, each of one or more content objects are associated with a score which may reflect a credibility of the content object. The score may be based, for example, on a publication frequency of a source, an impact factor of a source, a date of publication of the content object, and/or a number of citations to the content object.

It will be appreciated that the illustrated data stores 1155, 1165, 1176, 1177, 1178, 1181, 1182, and 1183 may each, independently and optionally, be included as a portion of data store 1372, which may include a relational database, for example.

Assessment network 1100 may also include a user device 1180 configured to detect input from a user 1185. User 1185 may be associated with an account or other authentication data indicating that access to some or all of the data is to be granted. Accordingly, user 1185 may be able to interact with various interfaces (presented at user device 1180) to view data pertaining to one or more particular clients (e.g., in an identified or de-identified manner), to view summary data that relates to data from multiple clients, to explore relationships between data types, and so on. In some instances, an interface may be configured to accept inputs from a user 1185 so as to enable the user to request data pertaining to (for example) materials with sparse indicators in particular data-set units, particular sparse indicators and/or state likelihoods.

In some instances, data is transmitted by assessment system 1105 and received at user device 1180. The transmitted data may relate to durations of work flow processing time periods. Specifically, as may be appreciated by disclosures included herein, generating outputs for users and/or requestors may involve multiple steps, each of which may include a process, which may be referred to herein as a task, of an entity and/or device. Completion times of individual processes may then be monitored and assessed. A work flow may include a structure and definition for these processes. For example, various work flows may include some or all of the following tasks:

Inputs are collected at client device 1130, transmitted by client device 1130, and received by assessment system 1105, where the inputs correspond to a preliminary request to conduct an assessment based on a material and ensure that all required inputs have been received;

A same or different client device 1130 (e.g., a wearable device) collects and transmits other data indicative of the client's activity or status;

Inputs collected at requestor device 1110$a$, 1110$b$ and transmitted to assessment system 1105 that correspond to a request for assessment for the client;

Access control device 1160$b$ at facility 1120 collects and transmits record data of the client;

Distribution device 1135 receives alert corresponding to new request and address information and confirms shipping of kit for sample collection to the client;

Client 1125 receives kit, collects material and sends to data generator 1140;

Assessment device(s) 1145 collects data-set data, and access control device 1160$a$ sends facility data to assessment system 1105;

Assessment system 1105 detects any sparse indicators in data set(s) and/or any modifications in data set expression;

Assessment system 1105 assigns any sparse indicators and/or data set availability modifications;

Evaluation device 1170 collects inputs identifying an assignment of any sparse indicators and/or data set availability modifications as of an unknown likelihood;

Confirmatory facility testing of any sample associated with a sparse indicator and/or data set availability modification having a particular assignment at same or different facilities;

Assessment system 1105 aggregates sparse indicator data, assignment data, record data, user or client inputs, other data, and/or activity or status data and generates one or more likelihood variables;

Assessment system 1105 generates electronic report with the one or more likelihood variables;

Evaluation device 1170 and/or requestor device 1110$a$ collect inputs indicating that the electronic report is approved for transmission to client device 1130; and Assessment system 1105 transmits the electronic report to client device 1130.

A work flow may include a task order that indicates that, for example, a first task is to be completed prior to performance of a second task, though a work flow may alternatively be configured such that at least some tasks may be performed in parallel. In some instances, one or more tasks in a work flow are conditional tasks that need not be performed during each iteration of the work flow. Rather, whether a conditional task is to be performed may depend on a circumstance, such as whether a result from a prior task is of a particular type or exceeds a threshold.

Using a work flow, assessment system 1105 may track timing of individual tasks during individual iterations of a work flow. Each iteration may correspond to generating a likelihood variable for a given client and may involve various other entities (e.g., reviewers, facilities, etc.), which may be selected based on, for example, user preference, a physical location of a client device, and/or availability. For tasks performed at assessment system 105, timing may be directly determined. For tasks performed by, at, and/or via another device, assessment system 1105 may track timing via electronic transmissions between systems. For example, a start may be identified by an instruction communication sent from assessment system 1105 and/or a when a communication was received indicating that the corresponding task was beginning. As another example, an end time may be identified by transmission of a communication including a result of the corresponding task sent from assessment system 1105 and/or when a communication was received indicating that the corresponding task was complete.

Figure 15:
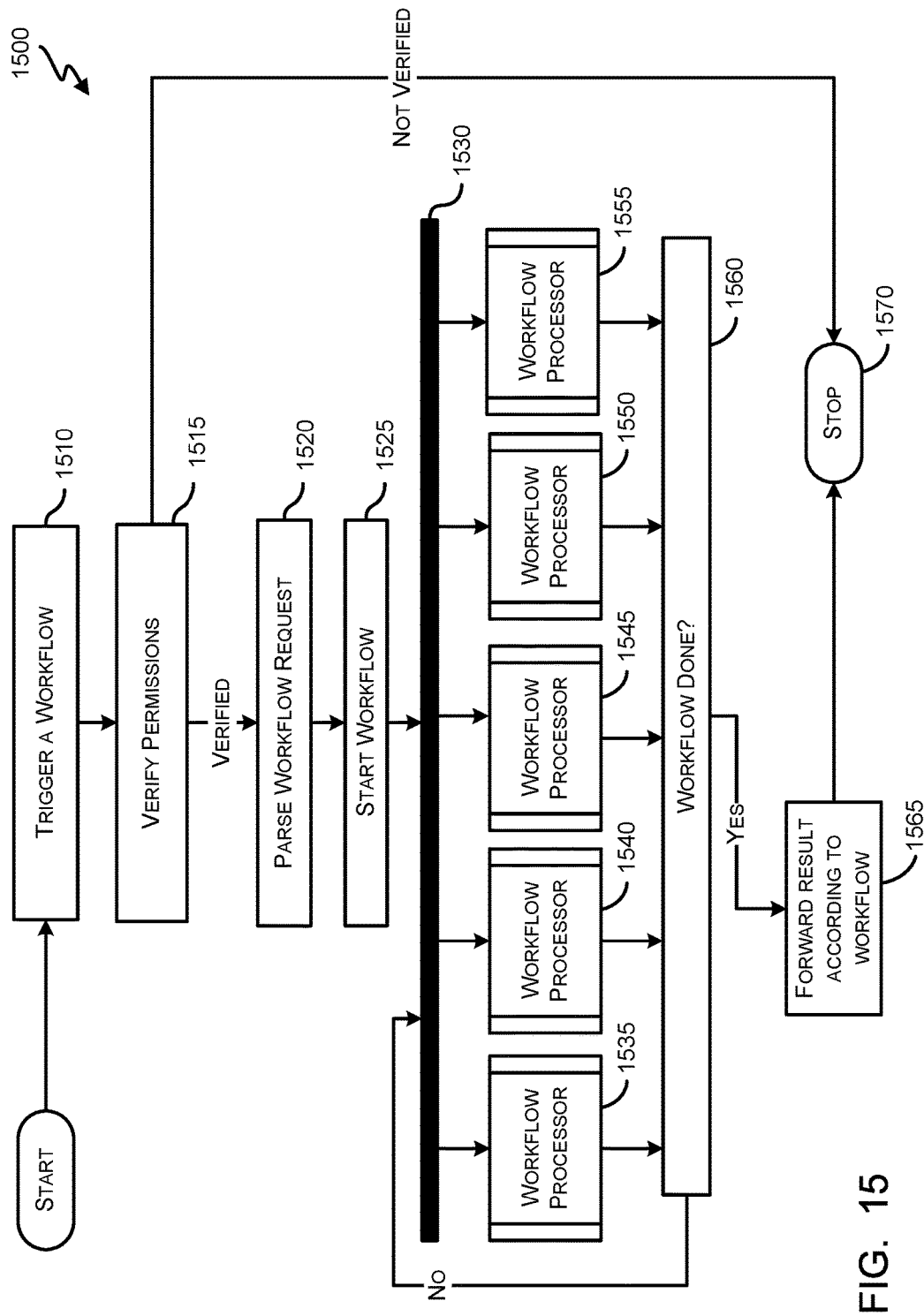
FIG. 15 shows an illustration of a work flow iteration, in accordance with some embodiments.

FIG. 15 shows a representation of an embodiment of a process 1500 for processing tasks in the assessment network 1100. The process starts when an event triggers a first work flow as shown at block 1510. Any number of events occurring internal to the assessment network 1100 and external to the assessment network 1100 may trigger a first work flow in any number of ways. Each of the assessment system 1105, a requestor device 1110, a client device 1130, a distribution device 1135, a facility data generator, an evaluation device 1170, a user device 1180, and an external assessment device 1190 may trigger a work flow, for example. For instance, the assessment system 1105 may trigger a work flow when it receives an electronic request 1205. A requestor device 1110 may trigger a work flow by transmitting electronic request 1205. A user device may trigger a work flow based on inputs collected. A data generator 1140 may trigger a work flow upon receipt of a sample. Other examples are possible and it will be appreciated from the present description that any one or more data transmissions between various devices and systems of assessment network 1100 may trigger a work flow. It will also be appreciated that various work flows may be initiated sequentially or simultaneously, depending on the particular need for completion of one work flow to complete before another work flow may begin. In addition, additional work flows may be triggered while in the midst of processing one work flow. In some embodiments, an assessment system or assessment device manages and/or coordinates triggered work flows. Optionally, task start times may be tracked, as described above, and triggering a work flow may include tracking the start time of tasks associated with the work flow.

Some task work flows may require verification of permissions and/or authorizations, such as depicted at block 1515, before the work flow is permitted to begin. For example, a transmission of record data of a client may require explicit authorization from a client or a requestor before the transmission may begin, for example, due to the sensitivity of information that may be included in the record data. As another example, transmission of information of a client to an external assessment device may also require client permission. In this way, permission verification may prevent unanticipated or unauthorized transmission of information to a particular work flow processor for which such transmission may be undesirable. Timing of permission request and verification may further be tracked, such as to allow identification of bottlenecks in work flow and/or task processing associated with permission verification. U.S. patent application Ser. No. 15/133,089, filed on Apr. 19, 2016 and U.S. Provisional Applications 62/150,218, filed on Apr. 20, 2016, and 62/274,660, filed on Jan. 4, 2016, disclose details regarding various work flow processes, and are each hereby incorporated by reference in its entirety for all purposes.

As illustrated in FIG. 15, if permissions are not verified, the work flow may be stopped, at block 1570. If permissions are verified, the work flow may proceed to block 1520. It will be appreciated that not all work flows require permission verification, and so block 1515 may be considered to be optional.

Depending on the particular work flow initiated, the work flow request may require parsing, at block 1520, to ensure that various portions of the work flow may be handled appropriately. Parsing may include determining that all required inputs, data, and/or materials needed for completing the work flow are available. In the event that additional inputs, data, and/or materials are needed, the work flow may be returned to the triggering device to request the additional inputs, data, and/or materials, for example. Parsing may also include aspects of load-balancing. Parsing may also include, for example, analyzing the work flow request and associated data and/or materials to ensure the data, materials and/or multiple individual sub-work flow processes are directed to an appropriate work flow processor 1535, 1540, 1545, 1550, 1555, etc. Task start times may optionally be tracked based on completion of parsing a work flow request, for example.

In one embodiment, a work flow may correspond to performing a data set analysis on a sample, which may include dividing the sample into sub-samples. The sub-samples may, for example, be redundantly analyzed to ensure accuracy. Parsing at block 1520 may include identifying necessary resources for completing a particular work flow.

After parsing the work flow request, the triggered work flow is started, at block 1525. Optionally, synchronizer 1530 oversees the processing of individual work flow processes by work flow processors. Optionally, tracked task start times may correspond to times at which the triggered work flow is actually passed to a work flow processor.

Some task work flows may include multiple individual work flow processes, such as a sequencing work flow for sequencing data-set unit data or sparse indicator data from a sample, where each individual work flow process may correspond to, for example, one or more data sets. These individual work flow processes may be performed in series, for example, such as if a particular work flow process requires input from a previous work flow process. The individual work flow processes may alternatively be performed in parallel, for example, if the separate work flow processes do not rely on an a result from another work flow process that may be performed simultaneously. Additionally, individual work flow processes may be started and completed without regard to other work flow processes that may be operating. Upon a work flow processor 1535, 1540, 1545, 1550, 1555 completing the designated tasks, at 1560, the work flow may be evaluated to determine whether the work flow is completed. If additional processing is required, the work flow may return to synchronizer 1530 for appropriate queuing. If no additional processing is required, the work flow result may be forwarded as appropriate, at 1565. Once a particular work flow is forwarded, the task associated with the work flow may stop, at block 1570. Optionally, task stop or end times may be tracked based on the time at which a work flow proceeds to stop at block 1570.

Assessment system 1105 may store task start and completion times, and/or task completion time periods (i.e., a difference between corresponding task completion and task start times) in process data store 1177 in association with an identifier of the corresponding task and an identifier of a corresponding work flow iteration (e.g., an identifier of a client or sample).

Assessment system 1105 may collect task start and completion times that correspond, for example, to a given time period, facility, user or client group, analysis type, etc. and analyze the data at a population level. Through such analysis, assessment system 1105 may identify average, median, or mode completion time periods for individual tasks so as to identify tasks, facilities, or entities associated with work flow processing delay. Further or alternatively, assessment system 1105 may identify a backlog for individual tasks by identifying a number of "open" tasks for which a start time has been identified but for which no completion time is identified. Tasks, facilities, and/or entities associated with high backlog may then be identified.

Such task completion time monitoring may be performed automatically and/or in response to a query communication from user device 180. For example, assessment system 1105 may determine, for each handling entity (e.g., facility, distribution device, reviewer, or facility) a portion of tasks completed by a first threshold time identified for a given task. Upon detecting that the portion exceeds a second threshold, an alert communication may be transmitted to user device 1180 and/or a device of an associated entity. As another example, assessment system 1105 may present a statistic (e.g., mean) corresponding to a processing time of each task in a work flow. The presentation may be interactive, such that more details about a statistic may be presented in response to a user selection of the statistic. For example, the statistic may be broken down by entity and/or task start time period, or more detailed information (e.g., a distribution or list of start and completion times) may be presented.

In some instances, data transmitted from assessment system 1105 to user device 1180 may relate to data queries received from user device 1180. The query may, in some instances, include one that specifically or implicitly identifies one or more data-set units. For example, identification of a given kit or assessment may be associated with one or more data-set units. Assessment system 1105 may identify data that any access constraints indicate are accessible to the user, and present high-level population data. For example, assessment system 1105 may identify a portion of clients for which any sparse indicator or a particular sparse indicator was detected at each of the one or more data-set units. Such data may be presented in an interactive manner, such that a user may select a represented portion of the data to drill down into that data. For example, the interface may accept a selection of a representation of each data-set unit, and the interface may be updated to identify a distribution of particular sparse indicators detected at the data-set unit.

A drill-down may be configured to, at some level, begin representing non-data set data. For example, a selection of a particular sparse indicator or data-set unit may result in a display identifying a distribution of history data or demographic data from amongst clients associated with the particular sparse indicator or a sparse indicator at the data-set unit. Thus, the drill-down may include retrieving data from different data stores depending on a level of precision. Further, each step in the drill-down may involve evaluating one or more applicable access constraints.

In some instances, a query may pertain to one or more data-set units, and query processing may include retrieving data (or results derived therefrom) and retrieving data set availability data (or results derived therefrom). For example, query processing may include identifying, for each subject and for each of the one or more data-set units, whether a sparse indicator or an data set availability modification was detected. A query result presentation may identify, for example, a portion of subjects for which a sparse indicator or modification was detected for each of the data-set units and/or a query result presentation may identify, for each of the one or more data-set units, a portion of subjects or clients for which a particular type of sparse indicator or modification was detected. The presentation may again be configured to accept drill-down inputs so as to enable a user to further explore the pertinent data.

As another example, query processing may include identifying instances in which, for a given client, both a sparse indicator (e.g., generally or of a particular type) and an data set availability modification (e.g., generally or of a particular type) was detected (e.g., generally, at a particular data-set unit and/or at a particular position at a data-set unit).

Again with reference to FIG. 11, assessment network 1100 may also include an external assessment device 1190 configured to detect input from a developer 1195. Via such inputs, external assessment device 1190 may send electronic requests for data (e.g., relating to particular data-set units, a particular user or client and/or particular user or client inputs) to assessment system 1105. The inputs may be received, for example, via a webpage, application, or app page, which may identify general types of data that is available for restricted access. Assessment system 1105 may evaluate the request to determine, for example, whether a corresponding client 1125 authorized such access (which may be verified via a communication exchange between assessment system 1105 and client device 1130) and/or whether such access is relevant to a purported type of analysis.

The evaluation may include assessing one or more permissions associated with a given user or client. In various instances, a permission may be set to be conditioned upon an entity or system transmitting a request, a type of data being requested, a size of data being requested, or a potential type of processing identified as being a use for the data. For example, a client may specify that an external assessment device may be granted access to data, such as data that includes data sets or sparse indicator detections, if the requested data pertains to fewer than a first threshold number of data-set units, that access to data that includes sparse indicator detection may be granted if the requested data pertains to fewer than a second threshold number of data-set units, and that access to the data is to be otherwise restricted.

Evaluation processing may depend, in part, on whether a system or entity associated with a request has provided any data previously or presently and/or what type of data is being provided. For example, external assessment devices and/or associated systems may provide data (e.g., generated from an external facility and/or client sample), results data, input data, data set availability data, test data, and/or history data.

Evaluation processing may depend on one or more permissions or restrictions associated with a request. The permissions or restrictions may be set, for example, based on client input, or lack thereof, and/or based on which type of analysis and/or data storage was initially agreed to by a client. For example, an interface may be configured so as to enable a user or client to permit or restrict storage of particular types of data (e.g., data sets and/or sparse indicator detection beyond what is needed to perform a requested analysis), to permit or restrict sharing data to one or more other entities (e.g., generally, of a given type or specific entities), and/or to permit or restrict using data to perform one or more other types of analyses. Permissions or restrictions pertaining to whether various analyses may be particularly important given that rules or regulations may require particular results of analyses to be transmitted to a client. Thus, if such information is not desired, analyses must be restricted.

In some instances, an interface may be configured to enable a user or client to specify a degree of identification to be associated with data of the client with regard to storage and/or distribution. For example, a user or client may be able to indicate that data and/or results are to be associated with a pseudo-randomly generated unique identifier of the client rather than client identifying information. As another example, a client may be able to indicate that data is to be stored so as to require a key for access, which may be held by the client. As another example, a client may authorize transmission of the client's data to external assessment devices so long as identifying information of the client (e.g., name, email, address, social security number, phone number, and so on) is not provided without subsequent explicit permission.

In some instances, a same or different permission may be established to apply to other type of data (e.g., with regard to storage and/or distribution), such as personal data, inputs and/or sensor data. In some instances, a same or different permission may be established so as to relate to data collected from external systems. For example, a permission may indicate whether an assessment system is authorized to request physician-system data (and/or what type of data), an external assessment device-data, etc., and/or how an assessment is to handle results provided by an external system.

If the evaluation indicates that access is to be granted, assessment system 1105 may, for example, send an instruction communication to data generator 1140 to conduct a new analysis of an existing sample, send a data request to a device (e.g., access control device 1160b, client device 1130), and/or retrieve data from a data store (e.g., and extract pertinent information from any larger data structure, such as extracting data-set unit-specific data from a reference dataset). When part or all of the data is accessible, one or more communications may be transmitted to the developer. The one or more meetings may include the data and/or may include information (e.g., access credentials, login information, or ftp IP address and credential information) to enable the developer to access the data. In some instances, other data different from that which was requested may be provided. The other data may include, for example, quality control metrics of the provided data, other data determined to be relevant to an analysis, and/or other data that is being provided in lieu part or all of data that had been requested.

Various devices in assessment network 1100 may communicate with one or more other devices in assessment network 1100 via a network, such as a communication system, the Internet, a local-area network, or a short-range network. Communications may be sent in a secure manner to, e.g., inhibit unauthorized access to health-record data. Techniques such as token authentication and/or encryption may be used.

It will be appreciated that the representations of devices and configurations depicted in FIGS. 11, 12, and 13 are illustrative. For example, while a single data generator 1140, client device 1130, and data stores 1178, etc., are shown, a system may include multiple data generators 1140, client devices 1130, data store 1178, etc. As another example, while access control devices 1160a, 1160b are shown as being connected to data store 1155 and record data store 1165, additional access control devices may be present in assessment network 1100. For example, an access control device may be included within or connected to assessment system 1105 so as to control access that requestor device 1110b, client device 1130, distribution device 1135, evaluation device 1170, user device 1180 and/or external assessment device 1190 may achieve.

Figure 16:
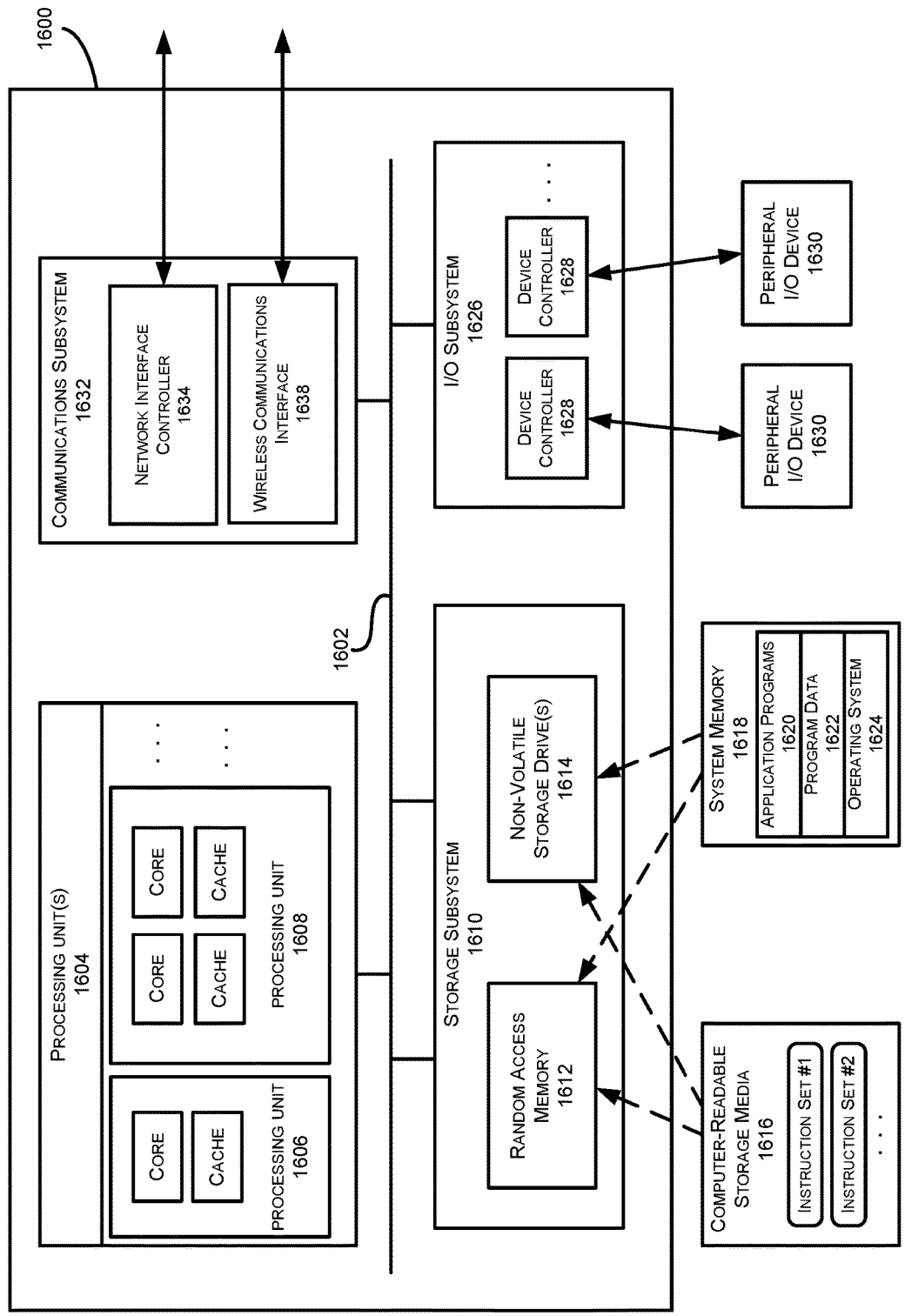
FIG. 16 shows a block diagram of an example data processing network device or system, in accordance with some embodiments.

With reference now to FIG. 16, a block diagram of an illustrative assessment network device 1600 is shown. The device 1600 may correspond to any of the devices or systems of the assessment network 1100 described above, or any other computing devices described herein, and specifically may include, for example, one or several of an assessment system 1105, a requestor device 1110, a client device 1130, a distribution device 1135, an assessment device 1145, a technician device 1150, an access control device 1160a, a reviewer device 1180, an external assessment device 1190, external system 1249, data-characterizer device 1410, data set analyzer 1420, and/or any of the work flow processors 1535, 1540, 1545, 1550, and 1555. Aspects of device 1600 may further be incorporated in one or more of data stores 1155, 1165, 1176, 1177, 1178, 1181, 1182, 1183, 1415, 1425, and 1430 and data store 1372. It will be appreciated that each of the devices referred to that may correspond to an instance of device 1600 may be independent and unique from all other instances of device 1600 and may include fewer or additional components as those illustrated in FIG. 16.

In the example illustrated in FIG. 16, device 1600 includes processing units 1604 that communicate with a number of peripheral subsystems via a bus subsystem 1602. These peripheral subsystems include, for example, a storage subsystem 1610, an I/O subsystem 1626, and a communications subsystem 1632.

Bus subsystem 1602 provides a mechanism for letting the various components and subsystems of device 1600 communicate with each other. Although bus subsystem 1602 is shown schematically as a single bus, alternative embodiments of the bus subsystem may utilize multiple buses. Bus subsystem 1602 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which may be implemented as a Mezzanine bus manufactured to the IEEE P1386.1 standard.

Processing unit 1604, which may be implemented as one or more integrated circuits (e.g., a conventional microprocessor or microcontroller), controls the operation of device 1600. Processing unit 1604 may be implemented as a special purpose processor, such an application-specific integrated circuit, which may be customized for a particular use and not usable for general-purpose use. One or more processors, including single core and/or multicore processors, may be included in processing unit 1604. As shown in FIG. 16, processing unit 1604 may be implemented as one or more independent processing units 1606 and/or 1608 with single or multicore processors and processor caches included in each processing unit. In other embodiments, processing unit 1604 may also be implemented as a quad-core processing unit or larger multicore designs (e.g., hexa-core processors, octo-core processors, ten-core processors, or greater).

Processing unit 1604 may execute a variety of software processes embodied in program code, and may maintain multiple concurrently executing programs or processes. At any given time, some or all of the program code to be executed may be resident in processor(s) 1604 and/or in storage subsystem 1610. In some embodiments, device 1600 may include one or more specialized processors, such as digital signal processors (DSPs), outboard processors, graphics processors, application-specific processors, and/or the like.

I/O subsystem 1626 may include device controllers 1628 for one or more user interface input devices and/or user interface output devices 1630. User interface input and output devices 1630 may be integral with device 1600 (e.g., integrated audio/video systems, and/or touchscreen displays), or may be separate peripheral devices which are attachable/detachable from device 1600. The I/O subsystem 1626 may provide one or several outputs to a user by converting one or several electrical signals to user perceptible and/or interpretable form, and may receive one or several inputs from the user by generating one or several electrical signals based on one or several user-caused interactions with the I/O subsystem such as the depressing of a key or button, the moving of a mouse, the interaction with a touchscreen or trackpad, the interaction of a sound wave with a microphone, or the like.

Input devices 1630 may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices 1630 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, haptic devices, and eye gaze tracking devices. Additional input devices 1630 may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices 1630 may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, haptic devices, and the like. In general, use of the term "output device" is intended to include all possible types of devices and mechanisms for outputting information from device 1600 to a user or other computer. For example, output devices 1630 may include, without limitation, a variety of display devices that visually convey text, graphics and audio/video information such as monitors, printers, speakers, headphones, automotive navigation systems, plotters, voice output devices, and modems.

Device 1600 may comprise one or more storage subsystems 1610, comprising hardware and software components used for storing data and program instructions, such as system memory 1618 and computer-readable storage media 1616. The system memory 1618 and/or computer-readable storage media 1616 may store program instructions that are loadable and executable on processing units 1604, as well as data generated during the execution of these programs. Program instructions may include instructions to perform one or more actions or part(s) or all of one or more methods or processes described herein. For example, program instructions may include instructions for identifying and/or aligning sparse indicators. Program instructions may include instructions for generating, transmitting, and/or receiving communications. Program instructions may include instructions for automated processing. Program instructions may include instructions for generating automated processing and/or stage results. Program instructions may include instructions for performing a work flow iteration.

Depending on the configuration and type of device 1600, system memory 1618 may be stored in volatile memory (such as random access memory (RAM) 1612) and/or in non-volatile storage drives 1614 (such as read-only memory (ROM), flash memory, etc.). The RAM 1612 may contain data and/or program modules that are immediately accessible to and/or presently being operated and executed by processing units 1604. In some implementations, system memory 1618 may include multiple different types of memory, such as static random access memory (SRAM) or dynamic random access memory (DRAM). In some implementations, a basic input/output system (BIOS), containing the basic routines that help to transfer information between elements within device 1600, such as during start-up, may typically be stored in the non-volatile storage drives 1614. By way of example, and not limitation, system memory 1618 may include application programs 1620, such as user applications, Web browsers, mid-tier applications, server applications, etc., program data 1622, and an operating system 1624.

Storage subsystem 1610 also may provide one or more tangible computer-readable storage media 1616 for storing the basic programming and data constructs that provide the functionality of some embodiments. Software (programs, code modules, instructions) that when executed by a processor provide the functionality described herein may be stored in storage subsystem 1610. These software modules or instructions may be executed by processing units 1604. Storage subsystem 1610 may also provide a repository for storing data used in accordance with the present invention.

Storage subsystem 1610 may also include a computer-readable storage media reader that may further be connected to computer-readable storage media 1616. Together and, optionally, in combination with system memory 1618, computer-readable storage media 1616 may comprehensively represent remote, local, fixed, and/or removable storage devices plus storage media for temporarily and/or more permanently containing, storing, transmitting, and retrieving computer-readable information.

Computer-readable storage media 1616 containing program code, or portions of program code, may include any appropriate media known or used in the art, including storage media and communication media, such as but not limited to, volatile and non-volatile, removable and non-removable media implemented in any method or technology for storage and/or transmission of information. This may include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This may also include nontangible computer-readable media, such as data signals, data transmissions, or any other medium that may be used to transmit the desired information and that may be accessed by device 1600.

By way of example, computer-readable storage media 1616 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray disk, or other optical media. Computer-readable storage media 1616 may include, but is not limited to, Zip drives, flash memory cards, universal serial bus (USB) flash drives, secure digital (SD) cards, DVD disks, digital video tape, and the like. Computer-readable storage media 1616 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for device 1600.

Communications subsystem 1632 may provide a communication interface from device 1600 and remote computing devices via one or more communication networks, including local area networks (LANs), wide area networks (WANs) (e.g., the Internet), and various wireless telecommunications networks. As illustrated in FIG. 16, the communications subsystem 1632 may include, for example, one or more network interface controllers (NICs) 1634, such as Ethernet cards, Asynchronous Transfer Mode NICs, Token Ring NICs, and the like, as well as one or more wireless communications interfaces 1638, such as wireless network interface controllers (WNICs), wireless network adapters, and the like. Additionally and/or alternatively, the communications subsystem 1632 may include one or more modems (telephone, satellite, cable, ISDN), synchronous or asynchronous digital subscriber line (DSL) units, FireWire interfaces, USB interfaces, and the like. Communications subsystem 1632 also may include radio frequency (RF) transceiver components for accessing wireless voice and/or data networks (e.g., using cellular telephone technology, advanced data network technology, such as 3G, 4G or EDGE (enhanced data rates for global evolution), Wi-Fi (IEEE 802.11 family standards, or other mobile communication technologies, or any combination thereof), global positioning system (GPS) receiver components, and/or other components.

The various physical components of the communications subsystem 1632 may be detachable components coupled to the device 1600 via a computer network, a FireWire bus, a serial bus, or the like, and/or may be physically integrated onto a motherboard or circuit board of device 1600. Communications subsystem 1632 also may be implemented in whole or in part by software.

In some embodiments, communications subsystem 1632 may also receive input communication in the form of structured and/or unstructured data feeds, event streams, event updates, and the like, on behalf of one or more users who may use or access device 1600. For example, communications subsystem 1632 may be configured to receive data feeds in real-time from other communication services, web feeds such as Rich Site Summary (RSS) feeds, and/or real-time updates from one or more third party information sources. Additionally, communications subsystem 1632 may be configured to receive data in the form of continuous data streams, which may include event streams of real-time events and/or event updates (e.g., data set completion, results transmission, other data transmission, report transmission, etc.). Communications subsystem 1632 may output such structured and/or unstructured data feeds, event streams, event updates, and the like to one or more data stores that may be in communication with device 1600.

Due to the ever-changing nature of computers and networks, the description of device 1600 depicted in FIG. 16 is intended only as a specific example. Many other configurations having more or fewer components than the device depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, it will be appreciated that there are other ways and/or methods to implement the various embodiments.

Figure 17:
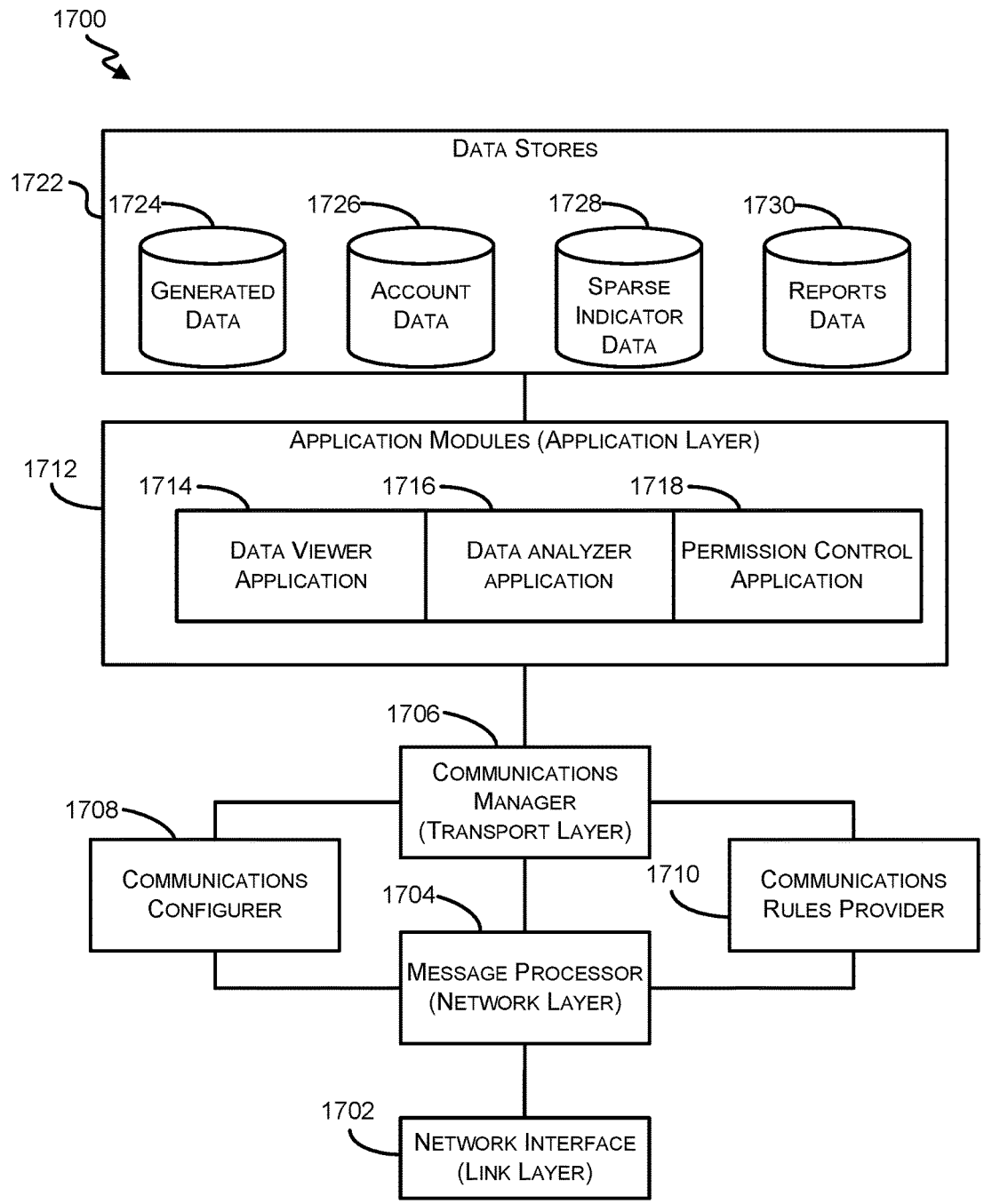
FIG. 17 illustrates components of a data processing network device or system, in accordance with some embodiments.

With reference now to FIG. 17, a diagram of components of an illustrative assessment network device 1700 is shown. The device 1700 may correspond to any of the devices or systems of the assessment network 1100 described above, or any other computing devices described herein, and specifically may include, for example, one or several of an assessment system 1105, a requestor device 1110, a client device 1130, a distribution device 1135, an assessment device 1145, a technician device 1150, an access control device 1160a, a reviewer device 1180, an external assessment device 1190, external system 1249, data-characterizer device 1410, data set analyzer 1420, any of the work flow processors 1535, 1540, 1545, 1550, and 1555, and/or device 1600. Aspects of device 1700 may further be incorporated in one or more of data stores 1155, 1165, 1176, 1177, 1178, 1181, 1182, 1183, 1415, 1425, and 1430, and data store 1372. It will be appreciated that each of the devices referred to that may correspond to an instance of device 1700 may be independent and unique from all other instances of device 1700 and may include fewer or additional components as those illustrated in FIG. 17.

Various components may be included in device 1700. Components may include some or all of the following: a network interface 1702 (which may operate in or function as a link layer of a protocol stack), a message processor 1704 (which may operate in or function as a network layer of a protocol stack), a communications manager 1706 (which may operate in or function as a transport layer of a protocol stack), a communications configurer 1708 (which may operate in or function as a portion of transport and/or network layer in a protocol stack), a communications rules provider 1710 (which may operate in or function as part of a transport and/or network layer in a protocol stack), and applications 1712 (which may operate in or function as an application layer of a protocol stack).

Network interface 1702 receives and transmits messages via one or more hardware components that provide a link-layer interconnect. The hardware components associated with network interface 1702 may include, for example, a radio frequency (RF) antenna or a port (e.g., Ethernet port) and supporting circuitry. In some embodiments, network interface 1702 may be configured to support wireless communication, e.g., using Wi-Fi (IEEE 802.11 family standards), Bluetooth, or other wireless communications standards.

The RF antenna, if present, may be configured to convert electric signals into radio and/or magnetic signals (e.g., to radio waves) to transmit to another device and/or to receive radio and/or magnetic signals and convert them to electric signals. RF antenna may be tuned to operate within a particular frequency band. In some instances, device 1700 includes multiple antennas, and the antennas may be, for example, physically separated. In some instances, antennas differ with respect to radiation patterns, polarizations, take-off angle gain and/or tuning bands. Network interface 1702 may include one or more phase shifters, filters, attenuators, amplifiers, switches and/or other components to demodulate received signals, coordinate signal transmission and/or facilitate high-quality signal transmission and receipt using the RF antenna.

In some instances, network interface 1702 includes a virtual network interface, so as to enable the device to utilize an intermediate device for signal transmission or reception.

For example, network interface 1702 may include or utilize virtual private networking (VPN) software.

Network interface 1702 may be configured to transmit and receive signals over one or more connection types. For example, network interface may be configured to transmit and receive Wi-Fi signals, Ethernet signals, cellular signals, Bluetooth signals, etc.

Message processor 1704 may coordinate communication with other electronic devices or systems, such as one or more user devices, requestor devices, assessment systems, data stores, assessment devices, distribution device, reviewer device, etc. In one instance, message processor 1704 is able to communicate using a plurality of protocols (e.g., any known, future and/or convenient protocol such as, but not limited to, internet protocol (IP), short message service, (SMS), multimedia message service (MMS), etc.). Message processor 1704 may further optionally serialize incoming and/or outgoing messages and facilitate queuing of incoming and outgoing message traffic.

Message processor 1704 may perform functions of an Internet or network layer in a network protocol stack. For example, in some instances, message processor 1704 may format data packets or segments, combine data packet fragments, fragment data packets and/or identify destination applications and/or device addresses. For example, message processor 1704 may defragment and analyze an incoming message to determine whether it is to be forwarded to another device and, if so, may address and fragment the message before sending it to the network interface 1702 to be transmitted. As another example, message processor 1704 may defragment and analyze an incoming message to identify a destination application that is to receive the message and may then direct the message (e.g., via a transport layer) to the application.

Communications manager 1706 may implement transport-layer functions. For example, communications manager 1706 may identify a transport protocol for an outgoing message (e.g., transmission control protocol (TCP) or user diagram protocol (UDP)) and appropriately encapsulate the message into transport protocol data units. Message processor 1704 may initiate establishment of connections between devices, monitor transmissions failures, control data transmission rates, and monitor transmission quality. As another example, communications manager 1706 may read a header of an incoming message to identify an application layer protocol used to receive the message's data. The data may be separated from the header and sent to the appropriate application. Message processor 1704 may also monitor the quality of incoming messages, detect out of order incoming packets, detect missing packets, reorder out of order packets, request retransmission of missing packets, request retransmission of out of order packets, etc.

In some instances, characteristics of message-receipt or message-transmission quality may be used to identify a quality status of an established communications link. In some instances, communications manager 1706 may be configured to detect signals indicating the stability of an established communications link (e.g., a periodic signal from the other device system, which if received without dropouts, indicates a stable link).

In some instances, a communication configurer 1708 is provided to track attributes of another system so as to facilitate establishment of a communication session. In one embodiment, communication configurer 1708 further ensures that inter-device communications are conducted in accordance with the identified communication attributes and/or rules. Communication configurer 1708 may maintain an updated record of the communication attributes of one or more devices or systems. In one embodiment, communications configurer 1708 ensures that communications manager 706 may deliver the payload provided by message processor 1704 to the destination (e.g., by ensuring that the correct protocol corresponding to the receiving system is used). Optionally, communications configurer 1708 may reformat, encapsulate, or otherwise modify the messages directed to the message processor 1704 to ensure that the message processor 1704 is able to adequately facilitate transmission of the messages to their ultimate destination.

A communications rules provider 1710 may implement one or more communication rules that relate to details of signal transmissions or receipt. For example, a rule may specify or constrain a protocol to be used, a transmission time, a type of link or connection to be used, a destination device, and/or a number of destination devices. A rule may be generally applicable or conditionally applicable (e.g., only applying for messages corresponding to a particular app, during a particular time of day, while a device is in a particular geographical region, when a usage of a local device resource exceeds a threshold, etc.). For example, a rule may identify a technique for selecting between a set of potential destination devices based on attributes of the set of potential destination devices as tracked by communication configure 1708. To illustrate, a device having a short response latency may be selected as a destination device. As another example, communications rules provider 1710 may maintain associations between various devices or systems and resources. Thus, messages corresponding to particular resources may be selectively transmitted to destinations having access to such resources.

A variety of applications 1712 may be configured to initiate message transmission, process incoming transmissions, facilitate permissions requests for access to protected data, facilitate automatic access to protected data, facilitate task work flow permission verification, and/or performing other functions. In the instance depicted in FIG. 17, application modules 1712 include a data viewer application 1714, a data analyzer application 1716, and/or a permission control application 1718. It will be appreciated that the application modules depicted in FIG. 17 are merely examples and other example application modules are include, but are not limited to, one that is associated with aspects of part or all of each of one or more actions, methods, and/or processes disclosed herein.

Data stores 1722 may store data for use by application modules 1712, as necessary, and may include, for example, generated data store 1724, account data store 1726, sparse indicator data store 1728, and reports data store 1730. Optionally, data store 1372 may be included in data stores 1722. It will be appreciated that fewer or more or different data stores than those illustrated in FIG. 17 may be included in data stores 1722, such as any one or more of data stores 1155, 1165, 1176, 1177, 1178, 1181, 1182, and 1183 depicted in FIG. 11.

One or more of data stores 1724, 1726, 1728, and 1730 may be a relational data store, such that elements in one data store may be referenced within another data store. For example, account data store 1726 may associate an identifier of a particular account with an identifier of a particular user or client. Additional information about the user may then be retrieved by looking up the account identifier in sparse indicator data store 1728, for example.

The components illustrated in FIG. 17 may be useful for establishing data communications and exchanging data between various other systems. For example, independent instances of device 1700 may represent the requestor device 1110 and the assessment system 1105 illustrated in FIGS. 11 and 12. Other examples are possible.

As an example, data analyzer application 1716 may perform alignment of data sets, request reference data, determine sparse indicators, determine scores, determine buckets, etc. Such actions may be performed in response to messages received by device 1700 from another instance of device 1700. If data that is unavailable locally in device 1700 is needed by an application module 1712, a request may be transmitted by device 1700, first by generating the request, forwarding the request to communications manager 1706, which then may process and modify the request as necessary for subsequent handling by message processor 1704. In turn, message processor 1704 may process and modify the request as necessary, such as by adding header and/or footer information, for subsequent handling by network interface 1702. Network interface 1702 may then perform further processing and modification of the request, such as by adding additional header and/or footer information, and then facilitate transmission of the request to a remote system, such as an external system that may possess the needed data.

Figure 18:
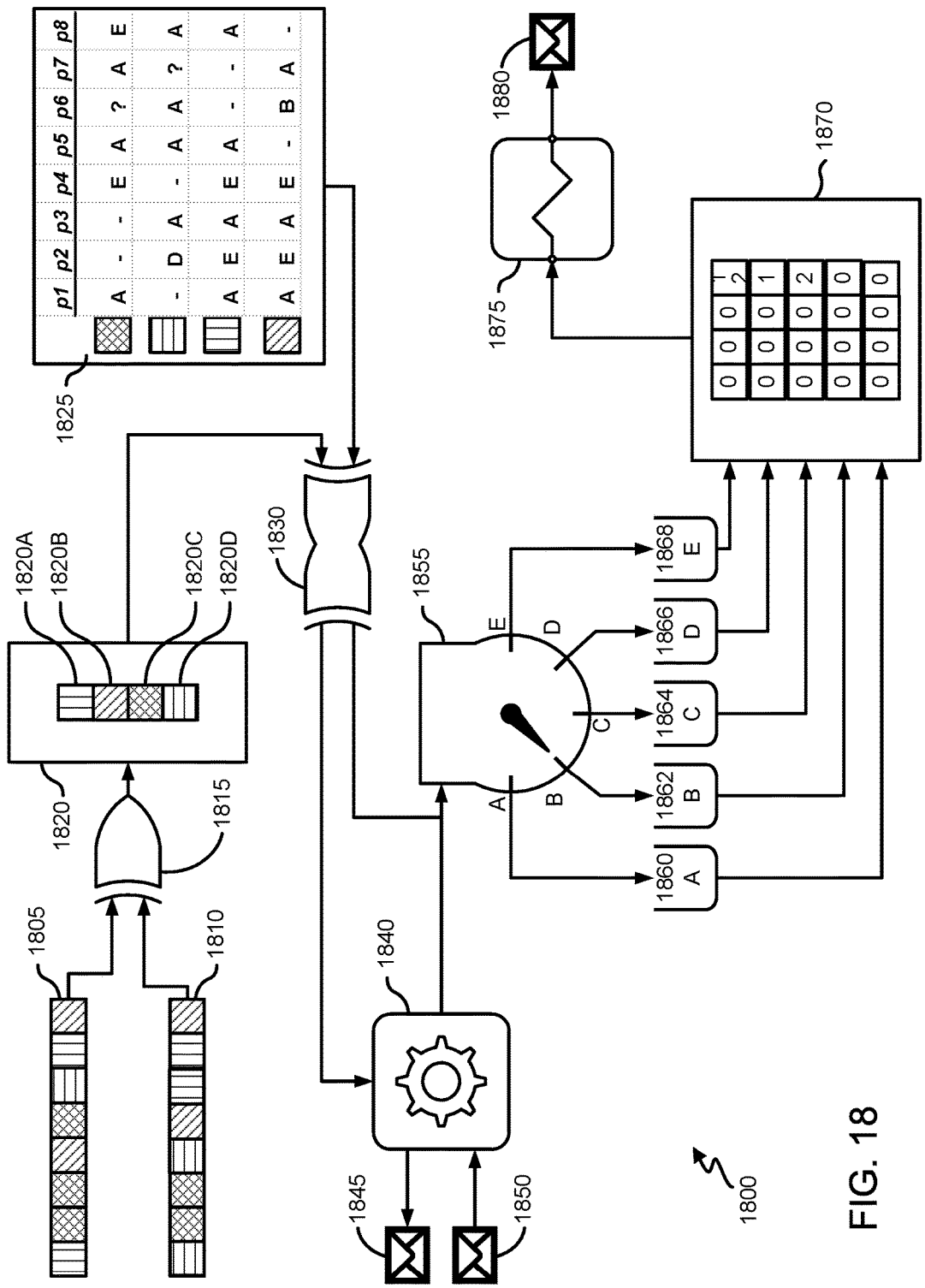
FIG. 18 shows a representation of a system for generating communications, in accordance with some embodiments.

Referring next to FIG. 18, a representation of a system 1800 for assigning sparse indicators to data buckets is shown, such as by performing a work flow iteration(s), performing automated processing for stage(s), generating stage result(s) from one or more stages of a work flow, and analyzing data buckets. System 1800 may represent portions of assessment system 1105 and may, for example, include portions of data generator 1140. System 1800 may be in data communication with one or more other components of assessment network 1100 or 1300, such as client device 1130 and data store 1372, for example.

System 1800 includes an assessment device 1815, which may be used to analyze and/or compare generated data 1805 with reference data 1810 to generate a data stream 1820, which may include one or more sparse indicators 1820A, 1820B, 1820C, 1820D, etc. Thus, it will be appreciated that data 1805 may include data aligned with a portion of a reference set, such that individual values of data 1805 may be compared to corresponding values in reference data 1810. In some embodiments, multiple individual data sets are obtained for a particular client and a compiled data set may be assembled from alignments of a plurality of the individual data sets. The compiled data set may be compared with one or more reference data sets or a compiled reference data set to identify sparse indicators associated with the compiled data set for the particular client. It will also be appreciated that generated data 1805 may include identifier data and coverage data that may be used by assessment device 1815 in generating data stream 1820, such as by comparing identifier data with reference data 1810 and using coverage data in tandem to determine a type, identity, value, and/or confidence metric associated with a sparse indicator in data stream 1820.

Different types of sparse indicators may be identified, such as a one-element sparse indicator representing a single data element different from a reference data set, or a clustered sparse indicator representing a set of consecutive data elements different from a reference data set. A clustered sparse indicator may be detected upon determining (for example) that a series of elements in a data set generally differ from those in a reference data set or that values in a coverage set change across the set so as to indicate that a portion of the reference data set is over- or underrepresented in the data set. Thus, in some instances, a reference set may include a reference coverage set. Although only four sparse indicators 1820A-1820D are depicted as part of data stream 1820, it will be appreciated that more or fewer sparse indicators may be identified for a particular set of generated data and that the four sparse indicators 1820A-1820D are merely examples.

System 1800 further includes a look-up engine 1830, which may determine whether each individual sparse indicator corresponds to bucket-assignment data in stored data 1825 (e.g., a look-up table). For example, a look-up table may include a set of entries, each of which corresponds to a sparse indicator. A sparse indicator may be identified (for example) by a position and identifier or by a range of positions and type of sparse identifier (e.g., type of structural sparse identifier and/or one or more corresponding position ranges in a reference data set). For example, FIG. 18 illustrates stored data 1825 arranged in a table or array, such that a value along a first dimension can represent an identifier detected in a client data set and a value along a second dimension can represent a position at which the identifier was detected. Elements that correspond to those in a reference data set need not have a value. Each of one or more other elements may include bucket-assignment data, which may identify a bucket to which the sparse indicator is to be assigned and, in some instances, a confidence of such assignment. In some instances, one or more elements indicate that bucket-assignment data is not yet available).

The depicted stored data 1825 may be useful for identifying bucket-assignment data for sparse indicators corresponding to differences between a client data set and reference data set at individual positions. It will be appreciated that additional stored data 1825 may identify bucket-assignment for other types of sparse indicators (e.g., structural sparse indicators), such as a sparse indicator that indicates that elements from Position X to Position Y are not present in a client data set.

If a look-up of a particular sparse indicator is successful, look-up engine 1830 may proceed to assign the sparse indicator in accordance with the bucket-assignment data. If a look-up of the particular sparse indicator is not successful or if a work flow calls for additional stages, the information associated with the sparse indicator and/or the result(s) from the look-up may be directed to data processor 1840.

Look-up engine 1830 may further allow for filtering of sparse indicators, such as to determine when a reviewer-assisted analysis of a particular sparse indicator is not needed or not to be performed. For example, some sparse indicators may be pre-assigned to particular data bucket(s) and look-up engine may identify these sparse indicators as such. In another example, some sparse indicators may not be suitable for an iterative analysis and/or may predetermined such that no resources are to be used in analyzing the sparse indicator. For example, some sparse indicators are associated with a position in a full data set for which analysis is determined to be unnecessary. Optionally, some sparse indicators are associated with a position in a full data set and value for which analysis is determined to be unnecessary.

System 1800 further includes a data processor 1840, which may perform iterative performance of automated processing for each of the sparse indicators in data stream 1820. It will be appreciated that more data processors 1840 may be included in system 1800, such as to allow parallel and/or sequential work flow performance. Data processor 1840 may perform fully automated processing of stages of a work flow and forward stage result(s) to bucketor 1855 for data bucket assignment.

In some embodiments of automated processing for one or more sparse indicators, data processor 1840 may encounter one or more stages having a stage-progression condition that is not satisfied or may determine that a reviewer-engagement condition is satisfied (e.g., due to a failure to identify a bucket for a sparse indicator in a look-up data store or due to determining that a bucket assignment for a sparse indicator is associated with a confidence metric that is below a predefined quantitative or qualitative threshold). Optionally, data processor 1840 may generate and transmit a query communication 1845 that includes one or more of a position associated with a sparse indicator, one or more values associated with the sparse indicator, and a result(s) from a previous stage of the work flow. The query communication 845 may be transmitted, for example, from system 1800 to an evaluation device 1170 to facilitate review and/or input by evaluator 1175. For example, evaluation device 1170 may receive the query communication 1845 and display the included information to allow the evaluator 1175 to provide response data to satisfy the stage-progression condition. Evaluation device 1170 may then generate a response communication 1850 that includes response data. Data processor 1840 may receive response communication 1850 and use the included response data to complete or augment the automated processing to generate stage result(s). Once the stages are completed according to the work flow, stage result(s) may be forward to bucketor 1855.

System 1800 further includes bucketor 1855, which may assign each sparse indicator to a bucket of a plurality of data buckets, such as by using stage result(s) from data processor 1840 and/or look-up result(s) from look-up engine 1830. Bucketor 1855 may then assign a particular data bucket for the particular sparse indicator being analyzed. It will be appreciated that more bucketors 1855 may be included in system 1800. In system 1800, five data buckets 1860, 1862, 1864, 1866, and 1868 are depicted, though it will be appreciated that more or fewer data buckets may be utilized. Some or all of data buckets 1860-1868 may, for example, span a range along a spectrum of a degree of likeliness that a client will transition into or experience a particular state. Upon full or partial completion of the assignment of the sparse indicators in data stream 1820 to data buckets, information may be passed to bucket assessor 1870. It will be appreciated that counts assigned to a set of buckets may be determined with respect to each of multiple position ranges (or units) or combinations thereof. For example, for a given data set, a count may be generated for each of a set of buckets and for each of a set of units that reflects a number of sparse indicators detected for the unit that correspond to the bucket.

System 1800 further includes bucket assessor 1870. Although bucket assessor 1870 is shown schematically as a separate component from bucketor 1855, it will be appreciated that bucket assessor 1870 and bucketor 1855 may be combined in a single component or process. Bucket assessor 1870 may identify a number of sparse indicators assigned to particular buckets 1860-1868 using one or more counters, for example. Bucket assessor 1870 may optionally determine whether one or more buckets include counts above a predetermined threshold (e.g., whether a count exceeds zero). The predetermined threshold may be (for example) defined by a user, generated based on machine learning, generated based on a virtual structural representor, and/or generated based on a population analysis. For example, in one instance, it may be determined whether a count in a given bucket or a total count across a combination of buckets (e.g., a bucket corresponding to a highest predicted likelihood, amongst the buckets, of transitioning into or being in a particular state or two buckets corresponding to the two highest predicted likelihoods) exceeds zero. It will be appreciated that predetermined thresholds for each data bucket may be independent of other predetermined thresholds. Bucket assessor 1870 may forward the counts corresponding to the buckets 1860-1868 to signal generator 1875.

A signal generator may use the counts and/or results of a threshold comparison, for example, to generate a communication 1880 indicative of whether a number of sparse indicators assigned to particular data buckets exceed the predetermined threshold(s). In some embodiments, different templates for communication 1880 may be used depending on which data bucket(s) exceed the predetermined threshold(s) and or by how much a threshold(s) is exceeded, for example. Communication 1880 may identify, for example, whether one or more sparse indicators are assigned to a bucket representing a highest probability, amongst the buckets, of transitioning into or being at a particular state. Communication 1880 may identify, for example, whether one or more sparse indicators are assigned to each of one or more other buckets.

Figure 19:
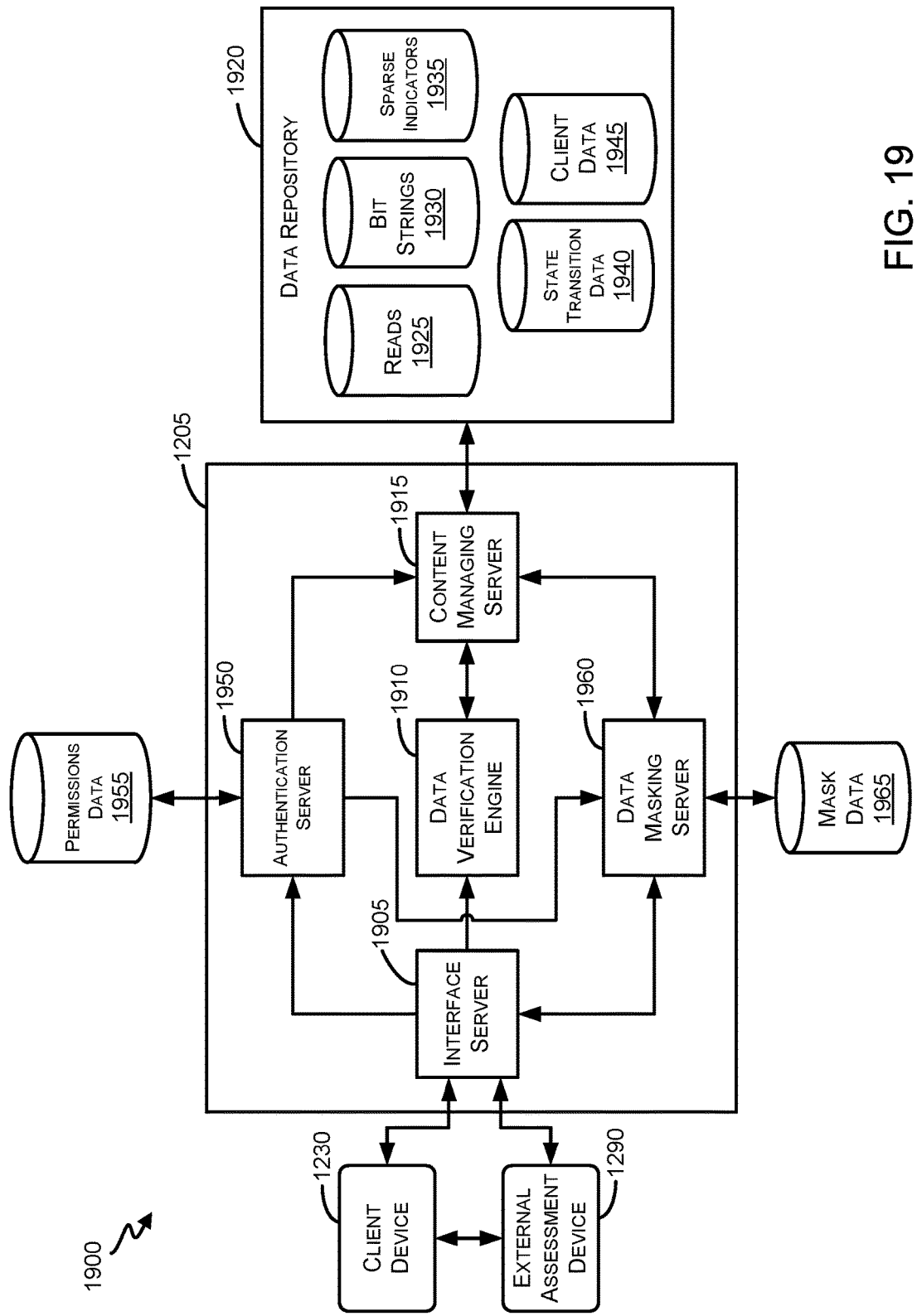
FIG. 19 shows a representation of a data management network, in accordance with some embodiments.

FIG. 19 shows a representation of a data management network 1900, in accordance with some embodiments. In some instances, data processing network 1100 includes part or all of data management network 1900. Generally, data management network 1900 includes assessment system 1105, which is in communication with each of client device 1130, external assessment device 1190 and various data stores.

Assessment system 1105 may receive one or more communications from client device 1130 that initiate or facilitate a process for generating a client data set and assessing the client data set so as to identify a result corresponding to a likelihood for transitioning to or being at a given state. Such communications may be received via an interface transmitted from assessment system 1105 to client device 1130 via an interface server 1905. The interface may include or be on presented (for example) via a webpage or app page.

Interface server 1905 may be configured to support an interface to request and/or receive client data (e.g., from a facility or access control device). A data verification engine 1910 can determine that a given client data corresponds a particular client and corresponds to one or more quality metrics that satisfy a data-acceptance condition. Upon such verification, a content managing server 1915 can store the client data in a data repository 1920. Data repository 1920 can include one or more data stores. While FIG. 19 shows data repository 1920 as including five data stores, it will be appreciated that the data stores need not be independent or separate and/or that data repository 1920 can include one or more other data stores. Data repository 1920 may include, in some instances, multiple storage elements that may be collocated or are remote from each other. In some instances, at least part (or all) of data repository 1920 is in the cloud. Further, one or more data processing servers (e.g., that are included within or external to assessment system 1105) may process the client data, and content managing server 1915 may store results of such processing at data repository 1920.

For example, a set of reads may be generated at a facility using a client sample. Interface server 1905 may receive the generated set of reads, and data verification engine 1910 may determine that it corresponds to a given client and is associated with an above-threshold quality metric. Content managing server 1915 may then store the set of reads (e.g., in association with an identifier of the client) at a read data store 1925 in data repository 1920.

Each read may be aligned to a portion of a reference data set. The aligned reads may then be used to generate one or more client bit strings or vectors. For example, a client bit string may represent a sequence for the client. The client bit string may thus include an identifier at each of a set of sequential positions. As another example, a client bit string may represent a coverage at each of a set of positions. The client bit string(s) can be stored (e.g., in association with an identifier of the client) in a bit string data store 1930.

The client bit string(s) can then be assessed to determine whether one or more sparse indicators are detected. The determination may include, for example, comparing a client bit string to a reference bit string or assessing changes of values of the bit string across position. Information pertaining to such determinations can be stored (e.g., in association with an identifier of the client) in a sparse indicator data store 1935. For example, the information may include, for each detected sparse indicator, one or more positions, types and/or bit-string values associated with the sparse indicators. Thus, the information may indicate how a given value or set of values in a client bit string differed from a corresponding value or set of values in a reference bit string or expected value or set of values. Each sparse indicator may be assigned to a bucket, and an indication as to which bucket the sparse indicator was assigned may be further stored in sparse indicator data store 1935 or another data store.

The sparse indicator data can be used to generate a predicted likelihood for transitioning into (or being at) a given state for a client. The predicted likelihood may be categorical, numeric or of another format and may be generated using a rule. For example, a rule may indicate that a given category is to be selected in response to detecting at least a threshold number of sparse indicators were assigned to a particular bucket. The predicted likelihood may be stored (e.g., in association with an identifier of the client) at a state transition data store 1940.

Data repository 1920 can also include a client data store 1945 that stores other data associated with a client. The other data may include, for example, identifying or contact information, such as a name, residential address, email address, phone number, age and/or alphanumeric identifier assigned to the client. The other data may include data provided via or generated based on one or more inputs detected at a client device. The other data may include activity data of the client, such as a time per day (e.g., average or median time per day) that the client spends in an active state as (for example) reported via input or received from an activity-monitoring device.

It will thus be appreciated that at least some data stored at data repository 1920 can include data (e.g., read data) received at assessment system 1105 from a facility or access control device. At least some data stored at data repository 1920 can include data (e.g., bit-string data, sparse-indicator data and/or state-transition data) generated at assessment system 1105, such as data generated based on read data. At least some data stored at data repository 1920 can include data (e.g., other client data) received from a client device or requestor device.

In some instances, at least some data stored at data repository 1920 can be received at assessment system 105 from external assessment device 1190. For example, external assessment device 1190 may be part of another assessment network that received a set of reads for a client, or external assessment device 1190 may have received a set of reads from a facility, data characterizer device or access control device. As another example, external assessment device 1190 may have generated data (e.g., bit-string data, sparse-indicator data or state-transition data) based on underlying data, such as data (e.g., read data, bit-string data or sparse-indicator data) received from assessment system 1105, another assessment system, a facility, a data characterizer device or access control device.

In instances where external assessment device 1190 transmits data to assessment system 1105, data verification engine 1910 may evaluate the data prior to storing it at data repository 1920. For example, data verification engine 1910 may evaluate data to determine a source for any provided data (and/or underlying data), a protocol for generating and/or processing data, a size of data and/or a quality metric of data. The evaluation may include (for example) determining whether a source is one of multiple verified sources or is of a credible source type. The evaluation may include determining whether the protocol conforms with a data-processing and/or data-generating rule. The evaluation may include determining whether a data size or quality metric exceeds a threshold. Data verification engine 1910 may further or alternatively assess a data confidence based on which external assessment device 1190 is providing the data. For example, higher confidence may be attributed to data provided by an external assessment device 1190 having provided high quantities of data previously, having had previously provided data verified by independent processing or generation techniques (e.g., performed at assessment system 1105 or at another system or device), being associated with a given type of entity (e.g., research institution), and so on.

External assessment device 1190 may also or alternatively request data. Interface server 1905 may transmit an interface to one or more external assessment devices 1190 that accept a data request. An interface may be provided (for example) via a webpage or app page. An interface may include one or more fields, each of which may accept a data specification. For example, one field may accept a specification of one or more units (e.g., by name or position range), one field may accept a specification of a type of data (e.g., whether reads, bit strings, sparse indicators, state transition data, and/or client data is being requested) and/or one field may accept a client specification (e.g., identifying a client by name or a client characteristic). To illustrate, an interface may be configured to accept a request for bit strings corresponding to three specified units and for client demographic data for each clients over the age of 50. In some instances, an interface may further include a field that accepts an identification of a type of processing to be performed using the requested data (e.g., a condition for which a state assessment is to be performed).

Interface server 1905 may further collect identifying data that identifies external assessment device 1190. For example, interface server 1905 may condition presentation of a data-request interface on a successful login; an interface (e.g., a data-request interface) may include a field that accepts (or requires) an identification of a login identifier or name associated with extern assessment device 1190; or interface server 1905 may automatically detect an IP address or other identifier associated with external assessment device 1190 based on a received communication.

In some instances, an authentication server 1950 queries a permission data store 1955 with identifying information (e.g., that includes a name of a developer, name of an entity associated with a developer, IP address, device identifier, and so on) corresponding to external assessment device 1190. A result of the query may indicate whether external assessment device 1190 is authorized to submit data requests, whether it is authorized to release (e.g., some or all) data to external assessment device, and/or for what types of data that release to external assessment device 1190 is authorized.

Permission data may be managed based on (for example) client inputs, communication exchanges between assessment system 1105 and external assessment device 1190 and/or one or more rules. For example, release of some or all data corresponding to a given client to an external assessment device 1190 may require that a communication have been received from a corresponding client device indicating that such release is to be permitted. The input may correspond to one or more specific external assessment devices or may apply generally. As another example, release of some or all data corresponding to a given client to an external assessment device 1190 may be permitted unless a communication has been received from a corresponding client device indicating that such release (e.g., to one or more specific external assessment devices or generally) is not authorized. Client-specific indications as to whether data release is authorized may be received (for example) during an initial intake process.

Permissions data store 1955 may then store indications as to which clients and/or for which external assessment systems release is authorized (or not authorized).

As another example, whether data release is authorized and/or which type of data release is authorized may depend on information or data having been received from a given external assessment device 1190. External assessment devices 1190 having provided client-specific data (e.g., of any type included in data repository 1920 or of one or more specific types) may be granted permission to access more data and/or to access data more frequently than other external assessment devices 1190. Alternatively or additionally, external assessment devices 190 having provided more information with regard to a type of processing to be performed using data and/or why particular data is being requested for the processing (e.g., via an identification of one or more scientific studies) may be granted permission to access more data and/or to access data more frequently than other external assessment devices 1190.

As yet another example, a rule may identify particular external assessment devices, particular types of external assessment devices, particular developers, particular types of developers, particular entities and/or particular types of entities that are to be granted permission to access more data and/or to access data more frequently than other external assessment devices 1190. To illustrate, expanded access may be authorized upon determining that a developer has authorized or submitted a payment for a particular data access, set of data accesses or period of time for data accesses.

In some instances, authentication server 1950 may determine that an external assessment device 1190 is authorized to receive some data corresponding to a request but not precision of data authorized for release differs from a data precision specified in the request. Authentication server 1950 may then modify the request to correspond to the authorized degree of precision. An indication that the modification is being performed may be transmitted to external assessment device 1190 and/or such modification may require an acceptance indication from external assessment device 1190.

Upon determining that an external assessment device 1190 is authorized with regard to processing of a request (or modified request), content managing server 1915 can query data repository 1920 (or one or more particular data stores therein) with one or more specifications of the request. In instances where data release is authorized (or not authorized) for particular clients, the query may be further configured so as to include corresponding client constraints, or a response to the query can be filtered to conform with the client constraint. It will be appreciated that, in some instances, processing a query includes querying multiple data stores. Data retrieved may be aggregated on a per-client basis using client identifiers and/or a client index.

In some instances, a data masking server 1960 processes and/or transforms data retrieved from data repository 1920 prior to transmitting it to external assessment device 1190. The processing and/or masking may include, for example, reducing a degree of data precision and/or replacing data. For example, client data that identifies an age of a client may be transformed to instead identify an age bracket for the client. As another example, client data that identifies a client name may be transformed to instead include a pseudonym or alphanumeric identifier. Thus, in some instances, a transformation includes masking first data with second data. The data mask (e.g., data substitution, which may include a substitution performed to de-identify data or reduce a degree of data precision) may be stored in a mask data store 1965. Whether a mask is to be applied and/or mask features may be determined based on a level of data access authorized for a given request. Thus, authentication server 1950 may transmit authentication information. In some instances, an indication as to which request(s), response(s) and/or external assessment device(s) is also stored at mask data store 1965.

Interface server 1905 may then transmit data (e.g., from or based on a query response, such as a transformed, processed and/or masked version thereof) to external assessment device 1190. The data may be, but need not be, transmitted over a same interface as used to accept a data request or a different interface. In some instances, the data is transmitted via (for example) download of one or more files, ftp, secure file transfer (e.g., using SSH) or other technique.

In some instances, external assessment device 1190 processes the data and identifies a result for each of one or more client. A result may include, for example, a detection or bucket assignment of each of one or more sparse indicators and/or a likelihood of transition to or experiencing a given state (e.g., condition). External assessment device 1190 may, in some instances, transmit the result(s) to data assessment system 1105, which may then store the result(s) and/or facilitate alerting one or more clients of the result(s). When the result(s) include one or more transformed client identifiers, data masking server 1960 may retrieve mask data to identify one or more original client identifiers to which the result(s) pertain. The result(s) can then be stored in association with client identifier(s) appropriately or transmitted to the appropriate client devices.

In some instances, external assessment device 1190 transmits a transformed client identifier to assessment system 1105, and a corresponding client address is transmitted from assessment system 1105 to external assessment device 1190 to enable external assessment device 1190 to directly alert the client of the result. In some instances, alert transmissions are more likely to be (or are only) facilitated and/or client addresses are more likely to be (or are only) provided may depend on a result when a result is of a particular character (e.g., identifying a high likelihood of experiencing a given state) and/or when a client permission is defined accordingly.

Figure 20:
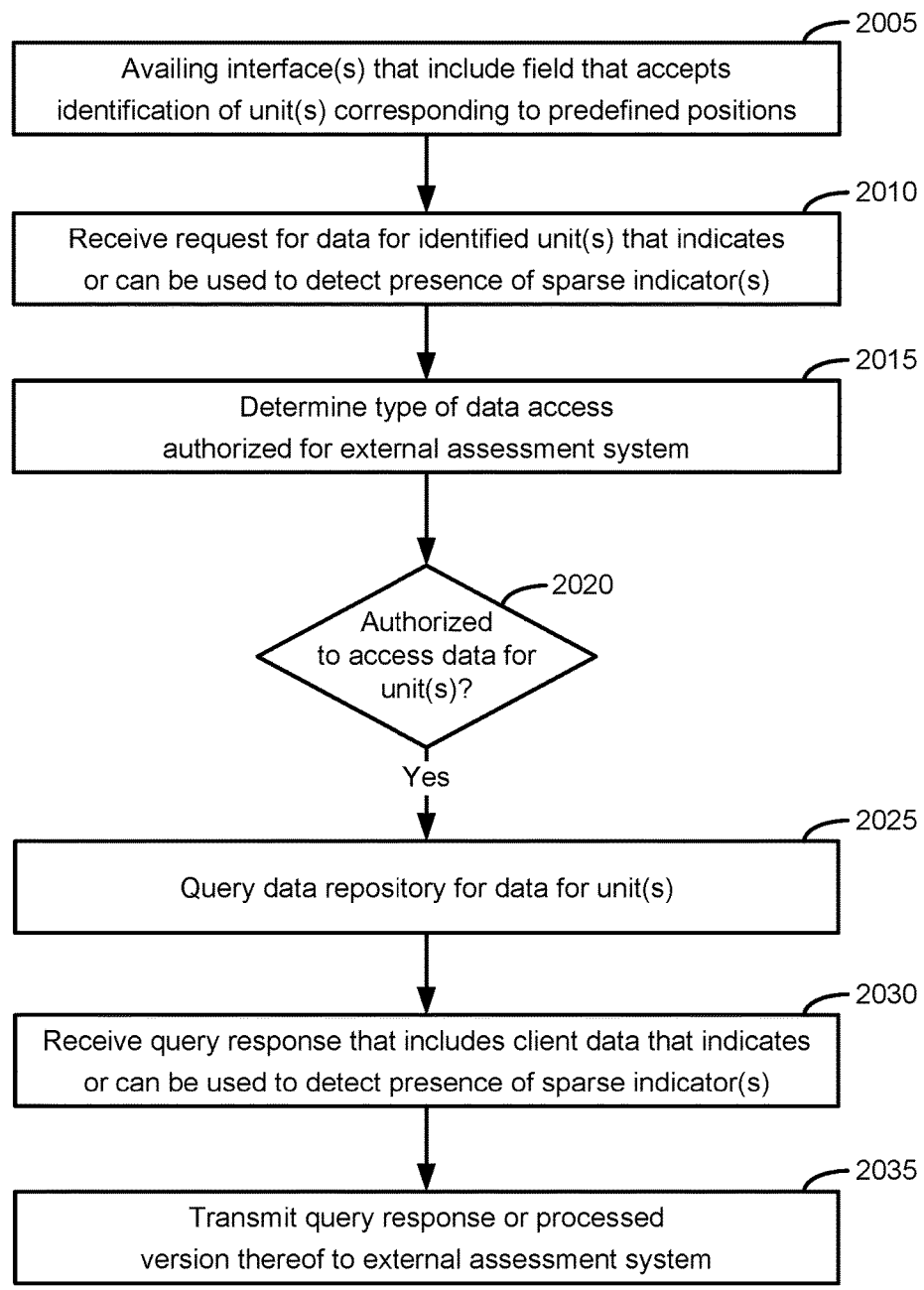
FIG. 20 illustrates a process for conditionally querying data repositories for data for specified units in response to receiving request communications over interfaces according to some embodiments.

FIG. 20 illustrates a process 2000 for conditionally querying data repositories for data for specified units in response to receiving request communications over interfaces according to some embodiments. Process 2000 may be performed, for example, in part or in its entirety by an assessment system, such as assessment system 1105. Process 2000 begins at block 2005 where one or more interfaces are availed. The one or more interfaces may be availed to each of a plurality of external assessment systems. For example, block 2005 may include hosting a webpage or app that includes the one or more interfaces. In some instances, the one or more interfaces include multiple interfaces, which may be availed to different types of external assessment systems (e.g., to conform with different device specifications) and/or which may be availed at different times (e.g., to collect different information).

The one or more interfaces may be configured to collect or accept information via one or more fields. A field may include an interface element that can receive input that corresponds to information. For example, a field may include a pull-down menu, radio-button list, and/or text box. Each field may be presented along with a field identifier that indicates what type of input is accepted at the field. A particular field may include on that accepts an identification of each of one or more units (e.g., one or more genes). Each unit may correspond to a set of predefined positions within a data structure.

At block 2010, a request communication is received. The request communication can be received from an external assessment system of the plurality of external assessment systems and over an interface of the one or more interfaces. The request communication can identify one or more units and can correspond to a request for data for the one or more units (e.g., by virtue of being received via the interface). The data being requested can be of a type that indicates or can be used to detect a presence of one or more sparse indicators. For example, the data being requested may include one or more sparse indicators, counts of sparse indicators assigned to each of one or more buckets on a per-client basis, one or more client data sets (e.g., bit strings) and/or one or more aligned reads. The request communication may, but need not, specifically identify a type of data (e.g., sparse indicators, counts, bit strings and/or reads). For example, in some instances, only one type of data is availed for request processing or a set of data types are provided in response to requests. As one illustration, a request communication may request a bit string that identifies particular bases aligned to each of five specified units for all clients for which such data is available. It will be appreciated that the request communication or another associated communication may include one or more additional constraints.

At block 2015, a type of data access authorized for the external assessment system is determined. Block 2015 may include identifying (for example) for which types of data, units, clients, and/or assessment types data access is authorized (or not authorized) and/or identifying degrees of data precision, client-identifying associations and/or mask features that are to be associated with data release (e.g., generally or for particular data types, units, clients and/or assessment types).

The type of data access may be determined (for example) using one or more rules, permission data, past data requests or data provisions (from or to) associated with the external assessment system, and/or profile data corresponding to the external assessment system (e.g., indicating whether the a fee, pertaining to a given request or more broadly applicable has been paid that grants enhanced data access and/or indicating a level of a membership associated with the external assessment system). In one instance, block 2015 includes identifying a set of clients that provided a data-release authorization or refusal (e.g., corresponding to a release of the data irrespective of whether it is associated with client-identifying information or corresponding to a release of data associated with client-identifying information) applicable to the request (e.g., that generally applies, that applies to a unit of the one or more units, that applies to the external assessment system and/or that applies to a type of assessment being performed by the external assessment system). In one instance, block 2015 includes determining what types of data are informative (e.g., based on a look-up table, content library and/or one or more studies) with regard to performing a type of assessment identified in the request or otherwise associated with the request.

At block 2020, it is determined whether the type of data access indicates that the external assessment system is authorized to access data for the one or more units. If it is determined that such data access is not authorized, a communication may be transmitted to the external assessment system indicating as such and/or the request may be modified (e.g., if possible) to correspond to a request for data that is authorized. For example, the request may be modified to pertain to fewer units than originally specified, the request may be modified to pertain to a different type of data than initially requested, the request may be modified to request data of a different degree of precision and/or the request may be modified to pertain to a different client group (e.g., a subset of clients corresponding to an initial request).

If it is determined that the type of data access indicates that the external assessment system is authorized to access data for the one or more units (or to access data associated with a modified request, process 2000 continues to block 2025 where a data repository is queried for the data for the one or more units. The query may be configured to include or otherwise abide by any of one or more other constraints.

It will be appreciated that the query or another query may further be performed for other client data. For example, a multi-constraint query may be for sparse indicators corresponding to a given unit and client location data. In various embodiments, the query may be configured to return results only for clients for which both types of data are available or for clients for which at least one type of data is available. When multiple types of data are requested, the query may be configured such that data is to be returned indicating which elements of one type of data correspond to other elements of another type of data with respect to client identity.

At block 2030, in response to the query, a query response is received that includes, for each client of a plurality of clients, client data of a type that indicates or can be used to detect a presence of one or more sparse indicators. For example, the client data may include an identification of each sparse indicator associated with the one or more units for the corresponding client. As another example, the client data may include a data set (e.g., bit string) that includes, for each of the one or more units, an identifier at each of a set of positions corresponding to the unit. The data set may then be compared to a reference data set to detect any sparse indicators. As yet another example, the client data can include, for each unit of the one or more units, a set of reads at least partly aligned with the unit. It will be appreciated that a query response may include other types of data, such as characteristics of clients and/or client-identifying data. When multiple types of data are returned, a query response may be configured so as to indicate which data elements correspond to each other with respect to client identity.

At block 2035, the query response or a processed version of the query response is transmitted to the external assessment system. The processed version may include (for example) a filtered version of the query response, such as one that filters out data corresponding to particular clients (e.g., that did not authorize data release). The processed version may include a version with transformed data, such as one that transforms individual client identifiers with other identifiers. The processed version may include a version conforming with a schema or format compatible with external assessment system and/or an interface.

The query response or processed version thereof may be transmitted over an interface, such as an interface connected to the one or more interfaces availed at block 2005. For example, a first webpage on a website may include an interface availed at block 2005, and a second webpage on the website may include an interface via which the query response or processed version thereof is transmitted. Transmitting the query response or processed version thereof may include, for example, transmitting a file via download, file transfer, message, and so on and/or providing data via a webpage, app page and/or message (e.g., email).

Figure 21:
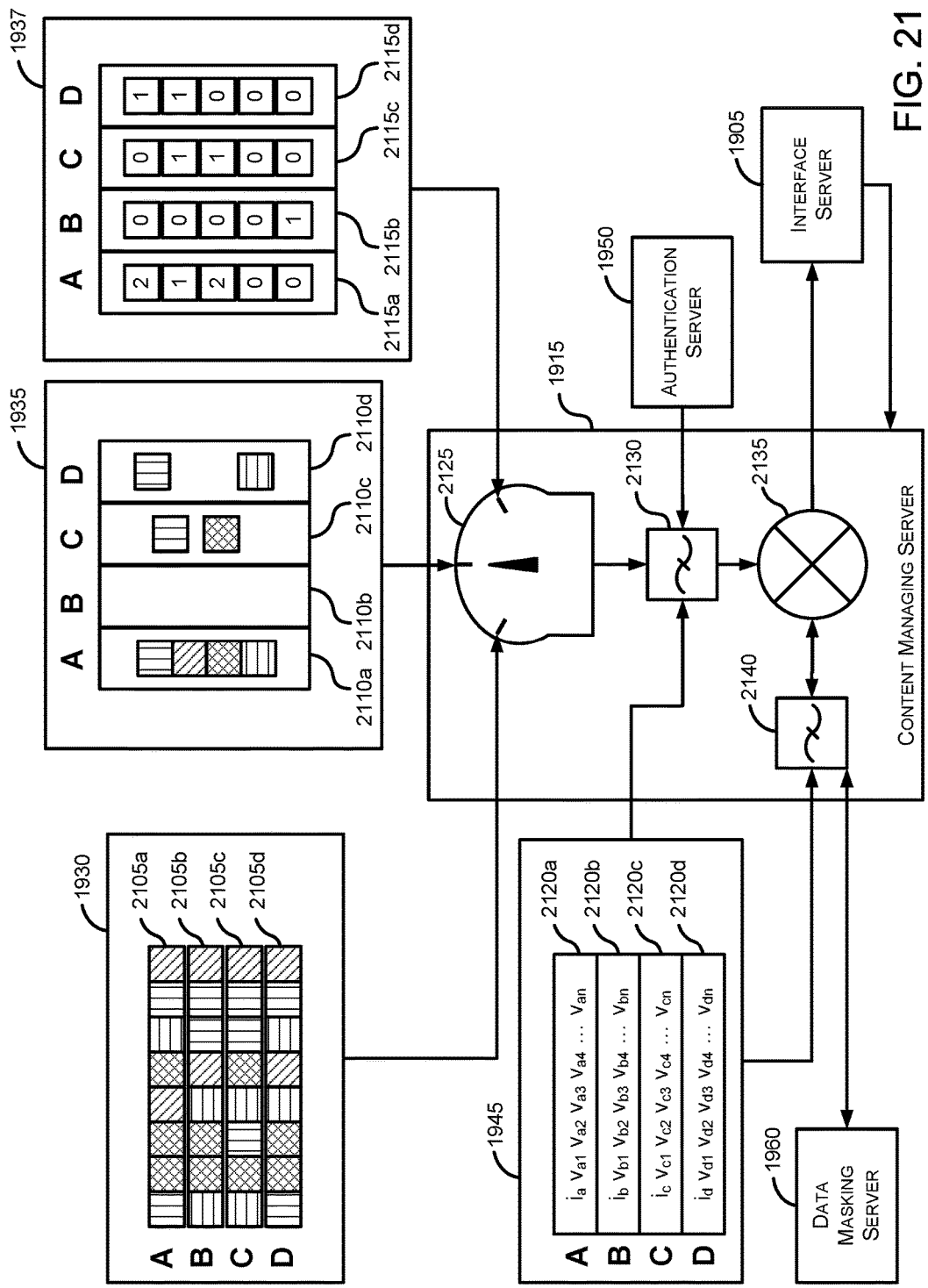
FIG. 21 shows a representation of a system for managing data distribution according to some embodiments.

FIG. 21 shows a representation of a system 2100 for managing data distribution according to some embodiments. Generally, FIG. 21 illustrates a flow via which content managing server 1915 can query a data repository during processing of a request. Four data stores are shown in FIG. 21, and each data-store representation is shown as including four data elements. Each of the data elements may correspond to a client. It will be appreciated that the depictions are illustrative and (for example) a data store may include more or fewer data elements and that various data stores need not include a same number of data elements.

In bit string data store 1930, each data element 2105$a$-$d$ corresponds to a string of identifiers. For example, a data element may include a string in which each value in the string is represented by a letter or a number. Each string may have been generated based on an assessment of a set of reads at least partly aligned with a series of positions corresponding to the string. In some instances, potential values at each position in the bit string are constrained. For example, bit strings may be defined such that an identifier at a given position is to correspond to one value of a set of four potential values.

In sparse indicator data store 1935, each data element 2110$a$-$d$ corresponds to an identification of each sparse indicator detected in a client-associated bit string (e.g., as determined based on identifying differences between the bit string and a reference bit string). Thus, for example, a data element 2110 may include an empty element if no sparse indicators are detected, a single data point or a set of data points, depending on a number of sparse indicators detected. Each data point may indicate one or more positions and one or more values or types of sparse indicators.

In a bucket-count data store 1937, each data element 2115$a$-$d$ may include a count of sparse indicators for a client assigned to each of one or more buckets. In the depicted instance, counts of each of five buckets are shown.

In client data store 1945, each data element 2120$a$-$d$ can include one or more client variables. A client variable can identify, for example, identifying information for a client and/or a characteristic of a client. It will be appreciated that one or more same types of variables may be included in multiple data elements corresponding to multiple clients and/or one or more types of variables may be represented in a data element for each of one or more first clients and not for each of one or more second clients.

Content managing server 1915 includes a data selector 2125 that identifies a type of data to retrieve for a given query. The identification can include identifying or can indicate from which data store to retrieve data. It will be appreciated that, in various instances, a single type of data or multiple types of data are retrieved. When multiple types of data are retrieved, the data may be retrieved concurrently (e.g., using different processes) or iteratively.

Data selector 2125 can select a type of data based (for example) partly or entirely on a rule that defines which types of data are authorized for release to a particular, to some or to all external assessment engines and/or that defines conditions for such release (e.g., pertaining to what constraints are specified in a request, what other data is requested, and/or a size of one or more data stores). For example, a rule may indicate that, for a particular external assessment system, any data from any of data stores 1930, 1935, or 1937 may be released so long as any constraints of a request are such to correspond to a number of data elements that exceed a threshold. This type of rule may inhibit an ability to define a request so precisely that it is possible to infer that one or more data elements correspond to a particular entity (e.g., person) with a confidence exceeding a confidence threshold.

Data selector 2125 can select a type of data based (for example) partly or entirely on a request. For example, a request may identify a type of data or a data store. As another example, a request may identify a protocol by which data is to be used. Data selector 2125 may then identify a (for example) type of data sufficient for use in the protocol. In instances where multiple types of data are sufficient for use in the protocol, a single type of data may (but need not) be selected based on precision and/or processing extent of the multiple types of data. To illustrate, a single type of data may be selected that would enable the protocol to start at a most advanced stage (e.g., being able to skip one or more initial processing steps).

Data selector 2125 may access a data store or portion of a data store that stores the select type of data. It will be appreciated that, in some instances, not all data of a given type is to be represented in a response to a request. Rather, a constraint implementor 2130 may effect one or more constraints.

A constraint may be defined based on a request. For example, a request may indicate that sparse-indicator data is being requested for one or more units. Thus, constraint implementor 2130 may identify data elements that correspond to the one or more units (e.g., via metadata) and/or may generate modified data elements that selectively pertain to the one or more units. As another example, a request may indicate that bucket-count data is being requested for female clients. Constraint implementor 2130 may then access client data store 1945 to determine which data elements from sparse indicator data store 1935 correspond to female clients. For example, constraint implementor 2130 may identify a list of client identifiers associated with female queries and then selectively retrieve data from sparse indicator data store 1935 for those identifiers, or constraint implementor 2130 may determine which data elements to filter out based on a looking up client identifiers associated with sparse indicator data elements in client data store 1945.

A constraint may be defined based on an authorization or permission. For example, authentication server 1950 may indicate that data release (e.g., generally or of a given type) is not authorized for one or more clients, and constraint implementor 2130 may filter out data elements for those clients. As another example, authentication server 1950 may indicate that data release is authorized only for one or more clients, and constraint implementor 2130 may selectively retrieve data elements for those clients. As yet another example, authentication server 1950 may indicate that data release to a particular external assessment system is only authorized for a set of units, and constraint implementor 2130 may selectively retrieve data elements (or portions thereof) corresponding to one or more units identified both via a request and for which data release is authorized. As still another example, authentication server 1950 may indicate that data release for a particular developer associated with a request is authorized only for clients included in a particular client network, and constraint implementor 2130 may filter out other client data.

It will be appreciated that a request response can include data of multiple types. In some instances, data is retrieved from each of multiple data stores or portions (e.g., partitions) of a data store (e.g., via individual queries), and a data aggregator 2135 then aggregates the data together. The data aggregation may be performed so as to associate individual data elements that correspond to a same client. In some instances, a data element of one type may be available for a client, while a data element of another type may not be. Data aggregator 2135 may respond by, for example, including the available data type (or processed version thereof) in a request response or by not including the available data type in a request response.

A second constraint implementor 2140 may filter or transform data elements retrieved from client data store 1945. Second constraint implementor 2140 may perform such filtering and/or transforming based on one or more factors described (for example) with respect to constraint implementor 2140, such as a factor based on a client data-release authorization or authorization associated with an external assessment system.

In some instances, a mask it to be applied to client data. Data masking server 1960 may apply a mask that (for example) changes a degree of data precision or replaces one or more variables with one or more others in a tractable manner (e.g., a client name or identifier with a pseuodo-randomly generated alphanumeric code. Content managing server 1915 can then avail the data (e.g., filtered, transformed and/or aggregated data) to interface server 1905, which can transmit the data to an external assessment system corresponding to a given request.

In some embodiments, a platform is offered to enable developers to request select genetic data for one or more clients (e.g., particularly identified, identified via a client characteristic or generally identified as any client). The platform may be configured to include a genetic app store that is managed by a central system and facilitates controlled provision of clients' data to developers and facilitating subsequent interactions between developers and clients (e.g., to convey results of developers' analyses to clients). Requests can be processed to determine whether a given developer is authorized to receive the requested data. Upon provision of data, a developer can analyze the data and provide results to the clients directly or to the managing system (e.g., to provide to clients).

In some embodiments, systems and methods relate to controlled distribution of client data. Various pre-approval steps may be implemented to determine what types of data distributions are authorized by a given client. For example, a client may specify that distribution of data pertaining to particular genes, for particular types of analyses (e.g., particular types of disease-risk of medication-efficacy analyses) is to be permitted (or conditionally permitted or not permitted). Permissions for performing medication analyses may specify what types of medications can be assessed (e.g., those in trials, approved, with specific journal-publication support) and/or how many medications can be assessed.

Pre-approvals may also include indications regarding to whom results will be released. Permissions may also specify or constrain how or whether raw data is stored (e.g., all of genome, sequences from select genes and/or just variants). Potentially, a permission indicates whether a client's data is permitted to be provided for research analyses. In various instances, pre-approvals may be configured to operate in accordance with an opt-in or opt-out protocol, so as to identify whether a default distribution decision is to allow or to deny data distribution to external entities.

Due to various requirements as to a need to release particular risk results, pre-approval pertaining to whether various types of variant detection may be particularly important (because detecting a variant may require disclosure, so it may need to be avoided initially). Permissions may extend to other types of data and/or data combinations. For example, a configuration may enable a client to specify that distribution of data identifying variant detection (e.g., variant type and location) is to be permitted but distribution data identifying a sequence is to be refused. Other types of data may include heart rates, lipid profiles, sensor data, health record info, etc.

In some embodiments, a central system may collect clients' data (e.g., to be used for local analyses and/or provided, in a restricted manner, to developers) from a variety of sources. Such data collection may include integrating with different platforms. The sources may include one or more devices associated with the central system or another device (e.g., associated with a developer, physician or patient). The data collection may include crowd-sourcing pertinent data. In response to receipt of data pertaining to a client from a data source, the central system may coordinate to provide the data source with payment information, other data pertaining to the same client or data pertaining to a different client. In various instances, upon receiving the data from a source, a central system may have full or limited control on the data. For example, a communication rule may indicate that the central system may use the data for local analyses but cannot distribute the raw data to other entities. In various instances, received data may be "owned" by a data source, the central system or a client. Different sources may be assigned different credibility.

In some embodiments, risk assessments and/or biological analyses may use primary data (e.g., assessments of a sample or from a physician) pertaining to a relative of a client (e.g., in addition to or as an alternative to primary data pertaining to the client). In some instances, use of relatives' data may be subject to access control and/or an authorization (e.g., opt-in) by the client and/or relative of the client. The relative may include one as identified via input or automatically detected from genetic analysis. This type of data analysis may be, in some instances, more informative than the data provided via inputs as to whether (for example) a relative has or is at risk for having a disease. In some instances, a weight placed on primary data pertaining to a relative decreases as additional primary data is received from a client. For example, an initial biological analysis may be performed based on primary data from one or more relatives and a client's input. Subsequently, primary data for the client may be received, and the analysis may be repeated so as to decrease the weight applied to or use of the primary data of the relative(s).

Various types of biological analyses and/or risk assessments may (but need not) be associated with a fee charged to a client. Clients may be charged differently based on how many genes or panels were ordered. There may be a threshold where a client would "own" his/her full genome data.

For example, in one instance, upon ordering at least a predefined number of assessments (e.g., risk assessments for a predefined number of conditions), one or more assessments pertaining to an evaluation of at least a predefined portion of the genome (e.g., number of genes and/or total sequence lengths), additional analyses may be provided for a reduced fee or no fee. In some instances, it may be required that the threshold be met with a single request, while in some instances, a cumulative assessment of multiple requests may be used to determine if the threshold is exceeded. When the threshold is met or exceeded, an assessment sequence (in some instances) may proceed to sequence an entire genome (or all portions of a genome relevant to any potential assessment). A model or algorithm may be used to predict which assessments a client is willing to subsequently request and prices may be adjusted accordingly. If advertisers and/or researchers are allowed to up-sell, client charges may be reduced.

Fess may (but need not) also be charged to a developer requesting data access. In some embodiments, developers can be charged differently based on how many genes' data is being requested, a type of data being requested (e.g., a raw sequence, an aligned sequence, variant-detection results, client inputs and/or personal health information data), and/or whether to developer is providing any data (e.g., for a same or different client).

In some embodiments, developers can submit queries to a managing system of the genomic app store. The queries may specify particular parts of the genome. The queries may request different or other types of data (e.g., blood sugar, lipid levels, activity patterns, health history, and/or sensor data, such as heart rate) and/or other types of data may be automatically identified as relevant. Queries can be evaluated based on authentication analyses and/or permissions. Quality control measures may be provided that corresponds to responsive data.

In some embodiments, clients' data may be partially or fully anonymized or de-identified. Data that is associated with client's identities and their data may be stored and managed by an app-store managing system. In some instances, a client may be provided with a key to reveal data correspondence. A client may also be provided with an opportunity to delete corresponding data, which may result in total deletion of the data and/or de-identification of data.

In some embodiments, one or more developers may perform analyses to detect one or more diseases and/or to generate predicted affinities or medication efficacies. Clients with above-threshold results may then be identified. External assessment devices of developers may transmit alerts to client devices directly that identify the risk or risk and/or the transmission may be sent to an app-store managing system (which may then alert the client devices). Alerts may also be based on analyses performed for relatives. Identities of client may, or may not, be hidden from developers. Post-hoc alerts may also relate to "fun", recreational and/or non-clinical predictions, such as an eye color of child if a client had a child with a particular celebrity. Post-hoc analyses that are likely to be ordered or likely to be of interest to a given client may influence whether a sample is stored or whether the analysis is performed in the short-term.

Techniques described herein can provide various advantages. For example, data can be transmitted in a controlled manner. To illustrate, what data is released, how the data is released and/or to which systems the data is released can be evaluated for individual requested based on (for example) rules, permissions and/or data security. As another example, transmitting data that indicates or can be used to detect sparse indicators can improve an efficiency of data transmission and can further improve data security. As yet another example, establishing a network in which assessment systems interact to share and process data can improve a network efficiency with regard to data generation and processing.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A system for processing requests for client data, the system comprising:
   one or more data processors; and
   a non-transitory computer readable storage medium containing instructions that, when executed by the one or more data processors, cause the one or more data processors to perform actions including:
      receiving, using the one or more data processors, requests from a plurality of client devices for assessing genetic risks associated with a first medical condition, wherein the plurality of client devices are respectively associated with a plurality of clients;
      determining, using the one or more data processors, genetic information for each of the plurality of clients, wherein genetic information for a client includes sequence information for a plurality of genes for the client;
      analyzing, using the one or more data processors, a first subset of the genetic information to obtain respective genetic risk assessment results for each of the plurality of clients, wherein the respective genetic risk assessment results are associated with the first medical condition;
      making, using the one or more data processors, the respective genetic risk assessment results available to the plurality of clients;
      determining, using the one or more data processors, a plurality of permissions, each permission corresponding to an authorization provided by a particular client for sharing the sequence information for the plurality of genes for the particular client with one or more external assessment systems, wherein an external assessment system corresponds to a remote system distinct from the one or more data processors, and wherein the external assessment system has independent access to a data store including analysis results generated by the external assessment system;
      after determining the plurality of permissions, receiving, using the one or more data processors, a data request from a particular external assessment system, wherein the data request corresponds to a request for sequence information for one or more genes for each of the plurality of clients for assessing genetic risks associated with a second medical condition different from the first medical condition, wherein the sequence information for the one or more genes corresponds to a second subset of the genetic information, and wherein the second subset of the genetic information is at least partially different from the first subset of the genetic information;
      determining, using the one or more data processors, that an access authorization level for the particular external assessment system is sufficient for accessing the second subset of the genetic information;
      determining, using the one or more data processors, that the plurality of permissions authorize sharing the second subset of the genetic information for each of the plurality of clients with external assessment systems;
      obtaining, using the one or more data processors, the second subset of the genetic information for each of the plurality of clients and contact information for each of the plurality of clients; and
      transmitting, using the one or more data processors, a response to the data request, wherein the response to the data request includes the second subset of the genetic information for each of the plurality of clients and the contact information for each of the plurality of clients, and wherein
         receiving the second subset of the genetic information for each of the plurality of clients at the particular external assessment system facilitates the particular external assessment system generating second respective genetic risk assessment results associated with the second medical condition using the second subset of the genetic information, and
         receiving the contact information for each of the plurality of clients at the particular external assessment system facilitates the particular external assessment system providing the second respective genetic risk assessment results to the plurality of client devices.

2. The system of claim 1, wherein the second subset of the genetic information for each of the plurality of clients included in the response identifies variants included in the sequence information for the one or more genes for each of the plurality of clients.

3. The system of claim 1, wherein the second subset of the genetic information for each of the plurality of clients included in the response includes a string of base identifiers and positions for the one or more genes for each of the plurality of clients.

4. The system of claim 1, wherein the data request identifies the second medical condition and wherein the actions further include:
   determining that a particular gene of the one or more genes has an association with development of the second medical condition below a predefined threshold; and
   inhibiting transmission of sequence information for the particular gene in the response to the data request.

5. The system of claim 1, wherein the data request further requests a non-genetic client characteristic, wherein obtaining includes obtaining the non-genetic client characteristic for each of the plurality of clients, and wherein the response to the data request further includes the non-genetic client characteristic for each of the plurality of clients.

6. The system of claim 1, wherein the data request specifies a particular client characteristic, and wherein obtaining includes determining that each of the plurality of clients is associated with the particular client characteristic.

7. The system of claim 1, wherein determining the genetic information for each of the plurality of clients includes, for each of the plurality of clients:

receiving a set of reads;

aligning each read of the set of reads to a portion of a reference sequence to generate a set of aligned reads; and generating the sequence information for the plurality of genes based on the set of aligned reads.

8. A computer implemented method for processing requests for client data, the method comprising:

receiving, using one or more data processors, requests from a plurality of client devices for assessing genetic risks associated with a first medical condition, wherein the plurality of client devices are respectively associated with a plurality of clients;

determining, using the one or more data processors, genetic information for each of the plurality of clients, wherein genetic information for a client includes sequence information for a plurality of genes for the client;

analyzing, using the one or more data processors, a first subset of the genetic information to obtain respective genetic risk assessment results for each of the plurality of clients, wherein the respective genetic risk assessment results are associated with the first medical condition;

making, using the one or more data processors, the respective genetic risk assessment results available to the plurality of clients;

determining, using the one or more data processors, a plurality of permissions, each permission corresponding to an authorization provided by a particular client for sharing the sequence information for the plurality of genes for the particular client with one or more external assessment systems, wherein an external assessment system corresponds to a remote system distinct from the one or more data processors, and wherein the external assessment system has independent access to a data store including analysis results generated by the external assessment system;

after determining the plurality of permissions, receiving, using the one or more data processors, a data request from a particular external assessment system, wherein the data request corresponds to a request for sequence information for one or more genes for each of the plurality of clients for assessing genetic risks associated with a second medical condition different from the first medical condition, wherein the sequence information for the one or more genes corresponds to a second subset of the genetic information, and wherein the second subset of the genetic information is at least partially different from the first subset of the genetic information;

determining, using the one or more data processors, that an access authorization level for the particular external assessment system is sufficient for accessing the second subset of the genetic information;

determining, using the one or more data processors, that the plurality of permissions authorize sharing the second subset of the genetic information for each of the plurality of clients with external assessment systems;

obtaining, using the one or more data processors, the second subset of the genetic information for each of the plurality of clients and contact information for each of the plurality of clients; and transmitting, using the one or more data processors, a response to the data request, wherein the response to the data request includes the second subset of the genetic information for each of the plurality of clients and the contact information for each of the plurality of clients, and wherein receiving the second subset of the genetic information for each of the plurality of clients at the particular external assessment system facilitates the particular external assessment system generating second respective genetic risk assessment results associated with the second medical condition using the second subset of the genetic information, and receiving the contact information for each of the plurality of clients at the particular external assessment system facilitates the particular external assessment system providing the second respective genetic risk assessment results to the plurality of client devices.

9. The method of claim 8, wherein the second subset of the genetic information for each of the plurality of clients included in the response identifies variants included in the sequence information for the one or more genes for each of the plurality of clients.

10. The method of claim 8, wherein the second subset of the genetic information for each of the plurality of clients included in the response includes a string of base identifiers and positions for the one or more genes for each of the plurality of clients.

11. The method of claim 8, wherein the data request identifies the second medical condition and wherein the method further comprises:

determining, using the one or more data processors, that a particular gene of the one or more genes has an association with development of the second medical condition below a predefined threshold; and inhibiting, using the one or more data processors, transmission of sequence information for the particular gene in the response to the data request.

12. The method of claim 8, wherein the data request further requests a non-genetic client characteristic, wherein obtaining includes obtaining the non-genetic client characteristic for each of the plurality of clients, and wherein the response to the data request further includes the non-genetic client characteristic for each of the plurality of clients.

13. The method of claim 8, wherein the data request specifies a particular client characteristic, and wherein obtaining includes determining that each of the plurality of clients is associated with the particular client characteristic.

14. The method of claim 8, wherein determining the genetic information for each of the plurality of clients includes, for each of the plurality of clients:

receiving a set of reads;

aligning each read of the set of reads to a portion of a reference sequence to generate a set of aligned reads; and generating the sequence information for the plurality of genes based on the set of aligned reads.

15. A computer-program product tangibly embodied in a non-transitory machine-readable storage medium, the non-transitory machine-readable storage medium comprising instructions that, when executed by one or more data processors, cause the one or more data processors to perform actions including:

receiving, using the one or more data processors, requests from a plurality of client devices for assessing genetic risks associated with a first medical condition, wherein the plurality of client devices are respectively associated with a plurality of clients;

determining, using the one or more data processors, genetic information for each of the plurality of clients, wherein genetic information for a client includes sequence information for a plurality of genes for the client;

analyzing, using the one or more data processors, a first subset of the genetic information to obtain respective genetic risk assessment results for each of the plurality of clients, wherein the respective genetic risk assessment results are associated with the first medical condition;

making, using the one or more data processors, the respective genetic risk assessment results available to the plurality of clients;

determining, using the one or more data processors, a plurality of permissions, each permission corresponding to an authorization provided by a particular client for sharing the sequence information for the plurality of genes for the particular client with one or more external assessment systems, wherein an external assessment system corresponds to a remote system distinct from the one or more data processors, and wherein the external assessment system has independent access to a data store including analysis results generated by the external assessment system;

after determining the plurality of permissions, receiving, using the one or more data processors, a data request from a particular external assessment system, wherein the data request corresponds to a request for sequence information for one or more genes for each of the plurality of clients for assessing genetic risks associated with a second medical condition different from the first medical condition, wherein the sequence information for the one or more genes corresponds to a second subset of the genetic information, and wherein the second subset of the genetic information is at least partially different from the first subset of the genetic information;

determining, using the one or more data processors, that an access authorization level for the particular external assessment system is sufficient for accessing the second subset of the genetic information;

determining, using the one or more data processors, that the plurality of permissions authorize sharing the second subset of the genetic information for each of the plurality of clients with external assessment systems;

obtaining, using the one or more data processors, the second subset of the genetic information for each of the plurality of clients and contact information for each of the plurality of clients; and transmitting, using the one or more data processors, a response to the data request, wherein the response to the data request includes the second subset of the genetic information for each of the plurality of clients and the contact information for each of the plurality of clients, and wherein receiving the second subset of the genetic information for each of the plurality of clients at the particular external assessment system facilitates the particular external assessment system generating second respective genetic risk assessment results associated with the second medical condition using the second subset of the genetic information, and receiving the contact information for each of the plurality of clients at the particular external assessment system facilitates the particular external assessment system providing the second respective genetic risk assessment results to the plurality of client devices.

16. The computer-program product of claim 15, wherein the second subset of the genetic information for each of the plurality of clients included in the response identifies variants included in the sequence information for the one or more genes for each of the plurality of clients.

17. The computer-program product of claim 15, wherein the second subset of the genetic information for each of the plurality of clients included in the response includes a string of base identifiers and positions for the one or more genes for each of the plurality of clients.

18. The computer-program product of claim 15, wherein the data request identifies the second medical condition and wherein the actions further include:

determining that a particular gene of the one or more genes has an association with development of the second medical condition below a predefined threshold; and inhibiting transmission of sequence information for the particular gene in the response to the data request.

19. The computer-program product of claim 15, wherein the data request further requests a non-genetic client characteristic, wherein obtaining includes obtaining the non-genetic client characteristic for each of the plurality of clients, and wherein the response to the data request further includes the non-genetic client characteristic for each of the plurality of clients.

20. The computer-program product of claim 15, wherein the data request specifies a particular client characteristic, and wherein obtaining includes determining that each of the plurality of clients is associated with the particular client characteristic.

21. The computer-program product of claim 15, wherein determining the genetic information for each of the plurality of clients includes, for each of the plurality of clients:

receiving a set of reads;

aligning each read of the set of reads to a portion of a reference sequence to generate a set of aligned reads; and generating the sequence information for the plurality of genes based on the set of aligned reads.

* * * * *